(12) United States Patent
Nishi et al.

(10) Patent No.: US 6,590,090 B1
(45) Date of Patent: Jul. 8, 2003

(54) FAS LIGAND-LIKE PROTEIN, ITS PRODUCTION AND USE

(75) Inventors: Kazunori Nishi, Tsukuba (JP); Yukiko Hikichi, Tsukuba (JP); Yasushi Shintani, Tsukuba (JP)

(73) Assignee: Takeda Chemical Industries, Ltd., Osaka (JP)

( * ) Notice: Subject to any disclaimer, the term of this patent is extended or adjusted under 35 U.S.C. 154(b) by 106 days.

(21) Appl. No.: 09/653,285

(22) Filed: Aug. 31, 2000

Related U.S. Application Data

(62) Division of application No. 08/913,014, filed on Sep. 4, 1997, now Pat. No. 6,235,878.

(30) Foreign Application Priority Data

| | | |
|---|---|---|
| Jul. 19, 1996 | (JP) | 8-191204 |
| Aug. 9, 1996 | (JP) | 8-211695 |
| Jan. 31, 1997 | (JP) | 9-019330 |
| Jul. 17, 1997 | (WO) | PCT/JP97/02480 |

(51) Int. Cl.[7] ............................................. C07A 21/04
(52) U.S. Cl. .................. 536/23.5; 424/184.1; 435/69.1; 536/23.1; 530/350
(58) Field of Search ...................... 530/350; 424/184.1; 435/69.1; 536/23.1, 23.5

(56) References Cited

U.S. PATENT DOCUMENTS 6,235,878 B1 * 5/2001 Nishi et al. ................. 530/350

* cited by examiner

*Primary Examiner*—James Housel
*Assistant Examiner*—Myron G. Hill
(74) *Attorney, Agent, or Firm*—David G. Conlin; Robert L. Buchanan; Edwards & Angell, LLP

(57) ABSTRACT

This invention relates to a Fas ligand-like protein having an apotosis-inducing actibvity, etc. or its salt, a partial peptide of the protein or its salt; a DNA coding for the protein; a recombinant vector; a transformant; a method for producing the protein, a pharmaceutical composition comprising the protein, the partial peptide or its salt; and an antibody to the protein or the partial peptide. The protein, the partial peptide or its salt, and the DNA are useful as a prophylactic or therapeutic agent for cancer, viral infection, *Helicobacter pylori* infection, invasive staphylococcia, hepatitis, nephritis, bone disease, atherosclerosis or pain. The antibody can be used in assay of the protein, the partial peptide or its salt. The protein, the partial peptide or its salt is useful as a reagent for the screening for candidate medical compounds.

8 Claims, 22 Drawing Sheets

FIG. 1

```
CCCACGCGTCCGCCCACGCGTCCGCTGAGGTTGAAGGACC    40
CAGGCGTGTCAGCCCTGCTCCAGACACCTTGGGCATGGAG    80
                                 MetGlu

GAGAGTGTCGTACGGCCCTCAGTGTTTGTGGTGGATGGAC   120
GluSerValValArgProSerValPheValValAspGlyG

AGACCGACATCCCATTCACGAGGCTGGGACGAAGCCACCG   160
lnThrAspIleProPheThrArgLeuGlyArgSerHisAr

GAGACAGTCGTGCAGTGTGGCCCGGGTGGTCTGGGTCTC    200
gArgGlnSerCysSerValAlaArgValGlyLeuGlyLeu

TTGCTGTTGCTGATGGGGGCTGGGCTGGCCGTCCAAGGCT   240
LeuLeuLeuLeuMetGlyAlaGlyLeuAlaValGlnGlyT

GGTTCCTCCTGCAGCTGCACTGGCGTCTAGGAGAGATGGT   280
rpPheLeuLeuGlnLeuHisTrpArgLeuGlyGluMetVa

CACCCGCCTGCCTGACGGACCTGCAGGCTCCTGGGAGCAG   320
lThrArgLeuProAspGlyProAlaGlySerTrpGluGln

CTGATACAAGAGCGAAGGTCTCACGAGGTCAACCCAGCAG   360
LeuIleGlnGluArgArgSerHisGluValAsnProAlaA

CGCATCTCACAGGGGCCAACTCCAGCTTGACCGGCAGCGG   400
laHisLeuThrGlyAlaAsnSerSerLeuThrGlySerGl
```

FIG. 1A

```
GGGGCCGCTGTTATGGGAGACTCAGCTGGGCCTGGCCTTC     440
yGlyProLeuLeuTrpGluThrGlnLeuGlyLeuAlaPhe

CTGAGGGGCCTCAGCTACCACGATGGGGCCCTTGTGGTCA     480
LeuArgGlyLeuSerTyrHisAspGlyAlaLeuValValT

CCAAAGCTGGCTACTACTACATCTACTCCAAGGTGCAGCT     520
hrLysAlaGlyTyrTyrTyrIleTyrSerLysValGlnLe

GGGCGGTGTGGCTGCCCGCTGGGCCTGGCCAGCACCATC      560
uGlyGlyValGlyCysProLeuGlyLeuAlaSerThrIle

ACCCACGGCCTCTACAAGCGCACACCCGCTACCCCGAGG      600
ThrHisGlyLeuTyrLysArgThrProArgTyrProGluG

AGCTGGAGCTGTTGGTCAGCCAGCAGTCACCCTGCGGACG     640
luLeuGluLeuLeuValSerGlnGlnSerProCysGlyAr

GGCCACCAGCAGCTCCCGGGTCTGGTGGACAGCAGCTTC      680
gAlaThrSerSerSerArgValTrpTrpAspSerSerPhe

CTGGGTGGTGTGGTACACCTGGAGGCTGGGGAGAAGGTGG     720
LeuGlyGlyValValHisLeuGluAlaGlyGluLysValV

TCGTCCGTGTGCTGGATGAACGCCTGGTTCGACTGCGTGA     760
alValArgValLeuAspGluArgLeuValArgLeuArgAs

TGGTACCCGGTCTTACTTCGGGCTTTCATGGTGTGAAGG      800
pGlyThrArgSerTyrPheGlyAlaPheMetVal
```

FIG. 1B

```
AAGGAGCGTGGTGCATTGGACATGGTCTGACACGTGGAG   840
AACTCAGAGGGTGCCTCAGGGAAAGAAAACTCACGAAGC   880
AGAGGCTGGGATTACAGGCGTGAGCCACTGTTCCCAGCAG  920
GAATTTCTTTTTTATAGTATTGGATAAAGTTTGGTGTTTT  960
TACAGAGGAGAAGCAATGGGTCTTAGCTCTTTCTCTATTA 1000
TGTTATCATCCTCCCTTTTTGTACAATATGTTGTTTACC  1040
TGAAAGGAAGGTTTCTATTCGTTGGTTGTGGACCTGGACA 1080
AAGTCCAAGTCTGTGGAACTTAAAACCTTGAAGGTCTGTC 1120
ATAGGACTCTGGACAATCTCACACCTTAGCTATTCCCAGG 1160
GAACCCCAGGGGCAACTGACATTGCTCCAAGATGTTCTC  1200
CTGATGTAGCTTGAGATATAAAGGAAAGGCCCTGCACAGG 1240
TGGCTGTTTCTTGTCTGTTATGTCAGAGGAACAGTCCTGT 1280
TCAGAAAGGGGCTCTTCTGAGCAGAAATGGCTAATAAACT 1320
TTGTGCTGATCTGGAAAAAAAAAAAAAAAAAAA        1353
```

```
CGAGACTCCATCTCAAAAACAAAACAAATAAACGAACAAA          40
AAAACCCACAACGTATTATTTTCTTGTTTACGAGGTTTCT          80
TGTCTCTCTGGCTCCACCAGAAGAGGAGCAGGGACCCTTC         120
TTGCTGTTGTTCATTGCTGCATCCCCACACCGAGAGCAG          160
AGCCTGGCATGGGCAGAAGTCCTCAGTCGATATTTGGTG          200
GCCCCAAGCGAATGAAGCATCCAAGAAGGGAAAGCTGGGG         240
GCTCCCCACTGCACTTGCCACCTGAGTCACATTTTCAGAA         280
GCCTCTGGAAAGTCGTGCACAGCCCAGGAGTGTTGAGCAA         320
TTTCGGTTTCCTCTGAGGTTGAAGGACCCAGGCGTGTCAG         360
CCCTGCTCCAGACACCTTGGCATGGAGGAGAGTGTCGTA          400
                      MetGluGluSerValVal

CGGCCCTCAGTGTTTGTGGTGGATGGACAGACCGACATCC          440
ArgProSerValPheValValAspGlyGlnThrAspIleP

CATTCACGAGGCTGGGACGAAGCCACCGGAGACAGTCGTG          480
roPheThrArgLeuGlyArgSerHisArgArgGlnSerCy

CAGTGTGGCCCGGGTGGGTCTGGGTCTCTTGCTGTTGCTG          520
sSerValAlaArgValGlyLeuGlyLeuLeuLeuLeuLeu

ATGGGGCTGGGCTGGCCGTCCAAGGCTGGTTCCTCCTGC          560
MetGlyAlaGlyLeuAlaValGlnGlyTrpPheLeuLeuG

AGCTGCACTGGCGTCTAGGAGAGATGGTCACCCGCCTGCC          600
lnLeuHisTrpArgLeuGlyGluMetValThrArgLeuPr

TGACGGACCTGCAGGCTCCTGGGAGCAGCTGATACAAGAG          640
oAspGlyProAlaGlySerTrpGluGlnLeuIleGlnGlu
```

FIG. 2A

```
CGAAGGTCTCACGAGGTCAACCCAGCAGCGCATCTCACAG      680
ArgArgSerHisGluValAsnProAlaAlaHisLeuThrG

GGGCCAACTCCAGCTTGACCGGCAGCGGGGGCCGCTGTT      720
lyAlaAsnSerSerLeuThrGlySerGlyGlyProLeuLe

ATGGAGACTCAGCTGGGCCTGGCCTTCCTGAGGGGCCTC      760
uTrpGluThrGlnLeuGlyLeuAlaPheLeuArgGlyLeu

AGCTACCACGATGGGGCCCTTGTGGTCACCAAAGCTGGCT     800
SerTyrHisAspGlyAlaLeuValValThrLysAlaGlyT

ACTACTACATCTACTCCAAGGTGCAGCTGGGCGGTGTGGG     840
yrTyrTyrIleTyrSerLysValGlnLeuGlyGlyValGl

CTGCCCGCTGGGCCTGGCCAGCACCATCACCCACGGCCTC     880
yCysProLeuGlyLeuAlaSerThrIleThrHisGlyLeu

TACAAGCGCACACCCCGCTACCCCGAGGAGCTGGAGCTGT     920
TyrLysArgThrProArgTyrProGluGluLeuGluLeuL

TGGTCAGCCAGCAGTCACCCTGCGGACGGGCCACCAGCAG     960
euValSerGlnGlnSerProCysGlyArgAlaThrSerSe

CTCCCGGGTCTGGTGGACAGCAGCTTCCTGGGTGGTGTG     1000
rSerArgValTrpTrpAspSerSerPheLeuGlyGlyVal

GTACACCTGGAGGCTGGGGAGAAGGTGGTCGTCCGTGTGC     1040
ValHisLeuGluAlaGlyGluLysValValValArgValL
```

FIG. 2B

```
TGGATGAACGCCTGGTTCGACTGCGTGATGGTACCCGGTC   1080
euAspGluArgLeuValArgLeuArgAspGlyThrArgSe

TTACTTCGGGCTTTCATGGTGTGAAGGAAGGAGCGTGGT    1120
rTyrPheGlyAlaPheMetVal

GCATTGGACATGGGTCTGACACGTGGAGAACTCAGAGGGT   1160
GCCTCAGGGAAAGAAAACTCACGAAGCAGAGGCTGGGCG    1200
TGGTGGCTCTCGCCTGTAATCCAGCACTTTGGGAGGCCA    1240
AGGCAGGCGGATCACCTGAGGTCAGGAGTTCGAGACCAGC   1280
CTGGCTAACATGGCAAAACCCCATCTCTACTAAAAATACA   1320
AAAATTAGCCGGACGTGGTGGTGCCTGCCTGTAATCCAGC   1360
TACTCAGGAGGCTGAGGCAGGATAATTTGCTTAAACCCG    1400
GGAGGCGGAGGTTGCAGTGAGCCGAGATCACACCACTGCA   1440
CTCCAACCTGGGAAACGCAGTGAGACTGTGCCTCAAAAAA   1480
AAAAAAAAAA   1491
```

FIG. 2C

| FIG. |
| 3A |

| FIG. |
| 3B |

FIG. 3

TCTGCTCTGGCATGGAGAGTGTGGTACAGCCTTCAGTGTT   40
        MetGluSerValValGlnProSerValPh

TGTGGTGGATGGACAGACGGACATCCCATTCAGGCGGCTG   80
eValValAspGlyGlnThrAspIleProPheArgArgLeu

GAACAGAACCACCGGAGACGGCGCTGTGGCACTGTCCAGG   120
GluGlnAsnHisArgArgArgArgCysGlyThrValGlnV

TCAGCCTGGCCCTGGTGCTGCTGCTAGGTGCTGGGCTGGC   160
alSerLeuAlaLeuValLeuLeuLeuGlyAlaGlyLeuAl

CACTCAGGGCTGGTTTCTCCTGAGACTGCATCAACGTCTT   200
aThrGlnGlyTrpPheLeuLeuArgLeuHisGlnArgLeu

GGAGACATAGTAGCTCATCTGCCAGATGGAGGCAAAGCCT   240
GlyAspIleValAlaHisLeuProAspGlyGlyLysGlyS

CCTGGGAGAAGCTGATACAAGATCAACGATCTCACCAGGC   280
erTrpGluLysLeuIleGlnAspGlnArgSerHisGlnAl

CAACCCAGCAGCACATCTTACAGGAGCCAACGCCAGCTTG   320
aAsnProAlaAlaHisLeuThrGlyAlaAsnAlaSerLeu

ATAGGTATTGGTGGACCTCTGTTATGGGAGACACGACTTG   360
IleGlyIleGlyGlyProLeuLeuTrpGluThrArgLeuG

GCCTGGCCTTCTTGAGGGGCTTGACGTATCATGATGGGGC   400
lyLeuAlaPheLeuArgGlyLeuThrTyrHisAspGlyAl

FIG. 3A

```
CCTGGTGACCATGGAGCCCGGTTACTACTATGTGTACTCC    440
aLeuValThrMetGluProGlyTyrTyrTyrValTyrSer

AAAGTGCAGCTGAGCGGCGTGGGCTGCCCCAGGGGCTGG     480
LysValGlnLeuSerGlyValGlyCysProGlnGlyLeuA

CCAATGGCCTCCCCATCACCCATGGACTATACAAGCGCAC    520
laAsnGlyLeuProIleThrHisGlyLeuTyrLysArgTh

ATCCCGCTACCCGAAGGAGTTAGAACTGCTGGTCAGTCGG    560
rSerArgTyrProLysGluLeuGluLeuLeuValSerArg

CGGTCACCCTGTGGCCGGCCAACAGCTCCCGAGTCTGGT     600
ArgSerProCysGlyArgAlaAsnSerSerArgValTrpT

GGGACAGCAGCTTCCTGGGCGGCGTGGTACATCTGGAGGC    640
rpAspSerSerPheLeuGlyGlyValValHisLeuGluAl

TGGGGAAGAGGTGGTGGTCCGCGTGCCTGGAAACCGCCTG    680
aGlyGluGluValValValArgValProGlyAsnArgLeu

GTCAGACCACGTGACGGCACCAGGTCCTATTTCGGAGCTT    720
ValArgProArgAspGlyThrArgSerTyrPheGlyAlaP

TCATGGTCTGAAGGCTGCGGTGACAATGTATTTTGTGGAG    760
heMetVal

GGACCTCTCCAGGACTCACCTCAAACCCAGCAATA         795
```

FIG. 3B

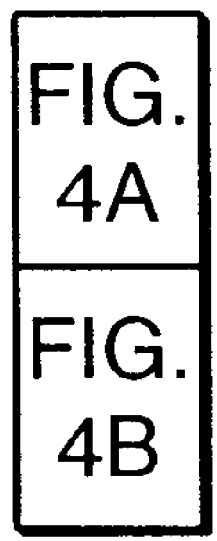
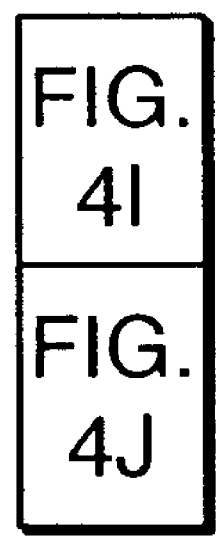
FIG. 4

```
TCTAGATTGCATTAACAGAGAAGACCCTGAGTATGCGT    40
GGAGTCATCTCAGGGCTGAGGTCCTGGGCTGAATGAAAAT  80
GACAGAGTGAGCAGAGCACCCGTGTTCTTTGGTTTCTGCT  120
ACCTCACTGTGGATTTGACATGACCAACTGCCTCGTGCTA  160
CCTCCCCTCTCCCACTTTGACTTCTCCACTGTGATAGAC   200
ACTTCTCACTATGAGCCAAGATTTTTCTTCCTCCCAGTCT  240
TAGTTGGGTTTCTACTGCTGTGCTAAACACCATGACCA    280
AAAGCAACTTGGAGAAGAGGGTTTATTTCAGTTACATT    320
TCCAGGTTATAGTTCATCACTGAATAAAATCAGGACAGGA  360
ATTCTAATTGTGCAGGATCCTGGAGGCAGTAGGTGACGCA  400
GAGGCCATGAGGATGCTGCTTGCTAGTTTGCTCCCCATGG  440
CTTGCTTGCTCAGCCTGCTTTCTTATAGAACCCAGGATCA  480
TCAGCCCAGGGGATGGTGCCATCCACAGTGGACTGGCCC   520
TTCCGCATCAATCACTAATGGAGAAATGCCCCACGGCT    560
TAAATGCATCCTGATCTTATGGAGGCATTTTTTTTTCAAC  600
TGAGGCTCCCTCCTCTCAGATGATTTTTGCTCGTGTCAAG  640
TTGACATAAAACTATCCAGCACCCTGTACCCTTTGTCATC  680
TTGACACACAAACACAACACTAGTAAGCCACAACCTTTCC  720
TTTCTTGTCATCTCCAAGATCAAACATTAATATCAACGTC  760
ACAACATAAAAACATTTGTGGGCTAGAGAGATGGCTTGG   800
AGGCTAAGAGCACTGGCTGTCCTTCAAGAAAATGAGCAAT  840
TCCCAGCACCCACACGGCAGCTCACAACTGTCTTTAATTC  880
ATTTTCCAGGGGATCCAAATCCCTCACACATGCAAGCAAA  920
ACACTAATGTACAGAAATAGAAATAAATAAATTTTTAAA   960
CATTTTGCAAACTTAAAAAAAAAAAAGTCCCACCACTTT   1000
ACAAATTCAAACAGGTTAAAATTTAGTGTCTTTAAAACTC  1040
CAAAGTTTAAAGTTGAAAAACCTTTAAAATCTAAAATATT  1080
TTAAAAGCTAGCCTCTCAGCTGTGGATCCTATAACATTG   1120
AAAACAAGCTTAATACTTCCTTATTTCAAGAGGGAAGAAC  1160
```

FIG. 4A

```
CACGGCACAGTCAACAACCTGAACAAGCAAAACCAAATAC  1200
CAGCTGTGTAAATAATTCGATTCCAGTGTCTGGATTCA   1240
AACATGATCTTCTGGCTCCTCCAAAGGTCCTGAGTGCCT  1280
TCTCTGGTGCTGCCCTATGCAGCCCTCACATCTTGTCTTC 1320
TAGGCTGGGCTGGCTCCACCCCAAGGCTGCTGCTGCTGC  1360
TGCTGCTGCTGGTGATCATCCAAGACACCAGCATCTTCA  1400
AAATACTGTGGTCTTCTGCTGCCACGGAGGCTGCACTTTC 1440
ACCAACAGCCTCTCCTGGTCCACACAGTGCCATGCCTCA  1480
GCTTCTCTCCATGGCCTCCTTATCCTTCCAAACCCAGCAT 1520
CATCTGAGGATAACCTTGTTCACCTTAACAGCACAGCTTC 1560
TGTGTACTGGTTCTCTCAGGAAACACTCCCCAGATTTCAC 1600
CTCAGTGATGCAGGTCTCTTCTAAATCACGGCCAGTTCTG 1640
CAGAACAAGCTAAGCAGAACTAAGAATCTCATTTCAAATA 1680
TCAAACATCCCCAATGCTCTCCTTGTTGTTGTTTTTGTTT 1720
TAAAATAGAATCCCTTTATAGTTCTTGCTCTCTTGGAACT 1760
CACTATGTAGAATAGGCTGGTTTTGATCTCACAGGAGATC 1800
CATCTGCCTCTGCCTCCCAAAGGTGTGTACTACCCTACCC 1840
AGGAAATCGTGGTGGTCTTTAAGAAACTCTCAAACTTCCC 1880
TCTGTAATTTCACAAGGCAGGCCTCCATCATCTGCCGTAT 1920
TCTCAGCATTTTGAACTTCCAAGCTCCACAGAACAGCCC  1960
ACTGAGCTCTGCATGGAACAGTTTCTCCAGTCCAAAGTTG 2000
AGAGGCCGTACAATCTTCTCAATACCATAGTCAGGTCTTT 2040
CCTATTCCTAACCCACACCTGATTCCAATTTGTGTCTTGG 2080
CTAGGATTTCTATTGCTGTCATAAACAGCATGATCAAAA  2120
GCAACCTCAGCTTACACTTTCACGTCACACCCCATCCACT 2160
GAGGGACGTCAGGACAGGAACCTGGAGACAGGAGCTGATG 2200
CAGAGACTATGGAAGAACACTGCTTACTGGCTTGTGTCCT 2240
ATGACTTGTTCAGCCTGCTTTCTTATAGAACTCAGGAATG 2280
CCAGTGCAGGGAAGGCCCAGTTTACAGTGAGCACGGCCTC 2320
```

FIG. 4B

```
CCACAAGCCAATCTGTTGGGCGTGTTTTCTCCATTGAAGT    2360
TTCCTCTTCCAAAATGAATGTAGCTTGTGTCAAATTGACA    2400
CTGGCCAGCACAGACCATGAGAGATTAGAGAACGCTTCCA    2440
GGCAGATCCTTTATGGAGTATCAGATACTCCGGCTGCTG     2480
AGTAATTTGCACAGTTCCAGGAATGGACCTGAGTTGGCA     2520
ACAGCAAAGAGATGAAGAAACGACAAACACAGACATCCAG    2560
GAATCCTGGGGTCATGTGATCTGGCCTTCTGCACACGAG     2600
TTCTCTTAGCACGTTATTATATAGAGTCGAGTGGAGAAGT    2640
GGGGTTATTGCCTACCACTGAAAAGGCAACTTATTACAT     2680
ACAGTTAAGCAAGGAGGCACGGTTTATATGCACAATGGA     2720
TGGGGAAGGCAGGTTCAGTTAGTCTCCATAAGAACTGTCC    2760
CTGGAAGGGAGCTATGTTCATGCGTCAGCACTCAAGGGG     2800
AGGATGGTGAACACATTCTACACACTGGCGACATGCAC      2840
ATCCATGCGTGGACCAGAAGAGAAGGCTATGTTTCCCTCT    2880
GGGTCTGAGGCTCTGGAGTTGTTGACAAGCTCATGTCAAC    2920
AGCACACATCCCTTCAGCACCTCACAGACCTGGCTTCCT     2960
CTGAAGGCTCTGTTGCTGAGGCAGGTGGATGGGTCGGTC     3000
CTGCAGGGGACAGGAGTCTCAGCAGTACTTTCCCCTGGA     3040
CCCTTGGTTAGAGAACCCATGAATCAGCAGCGTGGCAGAG    3080
CACTGGGGTTCTGTGGTCACAGCATCGCCAGCCCTGTGTC    3120
AAGACAAACACTACAGCATGGGGCCATTGACATTGAGAA     3160
GGGGCGCTGGTGATTCTTATAACTGAACCCCAAGTCTTC    3200
AGTATCTGGAGGGTGTCTGATGGGGTAAGCTCCAAGCT      3240
GAAGATTTGCGGACAAGGTGGTATCTGAAAATCTACCCCA    3280
GCACCGTCTCCAGTGGACACACATATGAACACATCTGAGG    3320
TTCATGTGTGCATGTGCTAATAGATGATAGACACTGTAGT    3360
GTGTGTGTGTGTGTGTGTCCATATATGGACCTGCACACAC    3400
ATCAGGAAATGCCTGTGTGCTTGTTCCAGCACTTGCAGAC    3440
ACATATCAGAACATCTACACCTGTGTGCACACATCCACGA    3480
```

FIG. 4C

```
ACCGTGCATCTGTACAAGCACCTGCACCCATATGCACAGA  3520
CTAAAGCAAACACAGAGGCCTCTGCTTGTCAGCGCGTGCA  3560
AATGCAGGTGCGGTGCAAGATGCTTGCATGGAACCCACAG  3600
AAGTTCTTTTGAGGGAAACAAAAGCCACCAAGTACATCGG  3640
AGCAGGGGCTGCCCCATCCATCCCACCTGAGTCACATTTT  3680
CTGGAAAGTGTGAGCTATGGTGGCCTCAGTGAGAGTGATC  3720
GACCGGGGCTGGCCTTCTGGGGCACAGGAAGAAGAGGA    3760
GGTACGTGAGGAAAGGGGAGGCACCAGACTTCAGCTTTAA  3800
AGTGAGTCCTAGGGGTGACAGGAACCTTTTGCAGTTTGCA  3840
CAGCCCGAGCGTGTTGGCAATTGTGGTTTCCTCCGGAGA   3880
GGAGGAACTCAGGCTTGCCAACCCTTTCCCCTGGCTTCG   3920
GAGCCTCAGCTGCTCTGGCATGGAGAGTGTGGTACAGCCT  3960
            MetGluSerValValGlnPro
```

```
TCAGTGTTTGTGGTGGATGGACAGACGGACATCCCATTCA  4000
SerValPheValValAspGlyGlnThrAspIleProPheA
```

```
GGCGGCTGGAACAGAACCACCGGAGACGGCGCTGTGGCAC  4040
rgArgLeuGluGlnAsnHisArgArgArgArgCysGlyTh
```

```
TGTCCAGGTCAGCCTGGCCCTGGTGCTGCTGCTAGGTGCT  4080
rValGlnValSerLeuAlaLeuValLeuLeuLeuGlyAla
```

```
GGGCTGGCCACTCAGGGCTGGTTTCTCCTGAGACTGCATC  4120
GlyLeuAlaThrGlnGlyTrpPheLeuLeuArgLeuHisG
```

```
AACGTCTTGGAGACATAGTAGCTCATCTGCCAGTAAGTGG  4160
lnArgLeuGlyAspIleValAlaHisLeuPro
```

FIG. 4D

```
GGCTTGGGAACCAGCGAGTCTTCTCCAGTACCTGTCCCT    4200
TTATCGTTGTGTATTGTGTGCTAGAACCCAGGGCTTCGT    4240
TAGCCTGTCTCTCTGACCCTCAGTCTTCTCATCTTTACAT   4280
GAGGATCTGATACACGTCCAGTGCCCGGCAGTTTCCTTGG   4320
GATTCACCTACTCGGTTGTTGTTTCCAGCCCAAACCTTTG   4360
TCCACCACTGGCTTCATGGTCACCCTGCTTCACTCGCAGC   4400
TCTCTCATGTGCTTGCTCTACTGTTTCCTTTCAGACAAGC   4440
CATGGGTGTGTCACAGTATGCTCCCGAGTCTTTGCCTATA   4480
TTTTCTTTTTAAGTTTTTTTTTTTAATTACATTTACTTAT   4520
TTAGTGTGTAGACATGAAAAGTATGCATGTCCGCAGCA     4560
TGTATGTGGAACACCTCTATGGAATCACTTCTCTGTGCCT   4600
TCCTTTGTGGAGGGTCCTAGGGACTGAACTCAGGTAGCCA   4640
GGCTTGGCAGCAAGCACTTTTACCGCCTGAGCCCTCTCAC   4680
CGGCCCTCAACTATCCAAAAACCTCGAAACAGTTCCGAA    4720
ACAATTCTAGTCTCAAGCATTTCAGACACTCGACTTGACT   4760
AGTTAATTCCTCATCCCAGCACTTGGGCAGGGAGGCAGA    4800
AGACTGAGGGAGTTCAAGGTCATCCTAGGCTATTTAGCAA   4840
GTCTGAGGCCAGACTGGGCTACATGAGAGCCTATCTTGA    4880
AATACAACAGATCTAATTAGGTGTGTGCCCCTCCCCCTGC   4920
ATCTGTGTGTATGTATGTGATATGTCATGTGTGGCTCTG    4960
CATACATGTCCATGGGTGGTGTCTGTGGCCATGGCCAGAC   5000
AGTCTCATCACCACATACCAGTGAGACTCGGAGCGGCATG   5040
TCCTTACCAAACATCCCTGTCTGCATTTCAGGATGGAGGC   5080
                                  AspGlyGly

AAAGGCTCCTGGAGAAGCTGATACAAGGTGAGTTTGCGC    5120
LysGlySerTrpGluLysLeuIleGlnA

CCCAGTCCCTTTGAAGCAGGTGGAATGGTTTCCGTTCAGC   5160
```

FIG. 4E

```
ACCTCCCCACACCAACTCTGGGTCATCACCCAGTGTCACA      5200
TTGTAGGCCTCGCAGGTGCCCCTCCCCAGGGCCAGAGAA       5240
GCAGAAATCTGGGTCCAAAAGGACAGAGCCTGACACAGG       5280
TAGCCTCAATTGATGTGTGAGAAACTTCGGGTACACACAC      5320
ACTGAGACATGCGTGCACACACACATACACACACAC          5360
ACACACACAATCCTCTTTTTGTCTCTAACCTTTGACTC        5400
TCTTCCTCAGATCAACGATCTCACCAGGCAACCCAGCAG       5440
        spGlnArgSerHisGlnAlaAsnProAlaA

CACATCTTACAGGTGAGAGGACCCCAGATCTTCACACGG       5480
laHisLeuThrG

AATGGGGTTTAGCATGTCCTCGGAGACTCAGATCTTTATA      5520
AGTTAGAGCACTCGTTTATGCATTCATTTAGTGTGTCTTT      5560
AAATTTTTTTTGACATTTACTTCTTTTTATTCATTTATTA      5600
TTGCACATGTCCATGCCATAGTGTAGAGGTCAGAAAACTC      5640
TCAGGGAACGATTCTTTCCTTCCACCTTTTGGCCTCCGT       5680
GTACTGATCTCAGCCATCAGGCTTGCTCTAAGTACCTTT       5720
ACTCTCTGCGCCATCTTGCCGGTCACTTTTTTTTTTCTCA      5760
GTGTTTACTAAAAACAGCCCAGAGAAGAGCCACAGGGAG       5800
CCATGTAAAGTCAACTCTTCACCCTGCTAGTCATGGGAC       5840
ACATCCCAAGGTCCTTGGAGGCCTCAGAAGATGTTGGAC       5880
TCAGACCTACCACAGTTTATATTTGTTTGTTTGTTTGGTT      5920
GGTTGGTTGGTTGGTTGGTTGGTTGATTGGTTCGTT          5960
GGTTTTGGTTTTGGAGACAGGGTCTCTCTGTGTAGCTTGG      6000
GCTGCCTGGGTAGACCTGCCTCTGTCCTGAGTACTGGAAT      6040
TAACAGGAATTAACGACGTGGCCACTACACCCAGCTGTA       6080
TATACTGGTTTTTCTTTTGGCATAGACAGTTTAATTTATA      6120
ATTTAACAAGTAAGAAACTAACAAGAATACACATAAAGTA      6160
```

FIG. 4F

```
TGCTGTAATTAAAAACTATTTTTGAAACATGATGTGGAG      6200
ATAGGGAGGTGGCTCCATGTGCAAATTGCTAGCCACTTTT     6240
GACTCAACATCTGAGCCAAAAGCCAAACACACACTCCCGT     6280
GACAGTTACAGAGGCAGATTCAGACAGACACACTCCTG       6320
TGACAGTCATGGAGACAGAGACAGGCAGAGAGGTCCCTAG     6360
GACCTGCTGTCCAGCAGCCTTGACAAACAGGGACTTCCA      6400
GGGTCAATAAGAGACTCTGCCTCAAAACTAAGGTGGACAG     6440
AGGTTGAAACTGAGGAAGTTGCCTGGTTTTGACTTCTGGG     6480
CACACACACACACACACACACATATATATAACACATAC       6520
ATCACACACATATACACAAACATACAGTCACACACTTT       6560
TTGAGATAGAGTCTCATGTAGCCTAAACCGGCCTTGAACT     6600
CTTGATCCTCCAGACTCGACGTCCAAGATCTGGATGTCA      6640
CCACTACACCTGATTTATTTCGTACTCGGGCTGGAATGTA     6680
CAGCCTTCGGCATGCTGGCGAGTGTTCCACCTCCTAAAT      6720
CCTAACCCCATTTAAAAAAATTTTTTTGACATTTCACTA      6760
GGAAGCTTCAATACCTTGTGCCTCAGTTTCTTCTTTGTA      6800
TTCAAGTGACTTTGCTCCTCAGTGCTTCAGTGTCTACCCT     6840
TGCAGAAGGAGATGGAATGAACGGAGTTAAGACACAACC      6880
ACCAAATTACTTTGCTTGCTTTCCTGTATCTCAGTTTCTT     6920
CCCCCTGCAAGATAGGAATGGGCTGAGTCAACCCAGACAA     6960
GCAGCCTACTATGGTGGTGAAACCAGAGGAACTAGCATA      7000
AGGTCACACAGAAAGGGTGGGCACAATGCTAACCGTGCTG     7040
ACGGGTTATCTTTCTCTCTCCTTTCCTCCCAGGAGCCAAC     7080
                                lyAlaAsn

GCCAGCTTGATAGGTATTGGTGGACCTCTGTTATGGAGA      7120
AlaSerLeuIleGlyIleGlyGlyProLeuLeuTrpGluT
```

FIG. 4G

```
CACGACTTGGCCTGGCCTTCTTGAGGGGCTTGACGTATCA        7160
hrArgLeuGlyLeuAlaPheLeuArgGlyLeuThrTyrHi

TGATGGGCCCTGGTGACCATGGAGCCCGGTTACTACTAT         7200
sAspGlyAlaLeuValThrMetGluProGlyTyrTyrTyr

GTGTACTCCAAAGTGCAGCTGAGCGGCGTGGGCTGCCCCC        7240
ValTyrSerLysValGlnLeuSerGlyValGlyCysProG

AGGGGCTGGCCAATGGCCTCCCCATCACCCATGGACTATA        7280
lnGlyLeuAlaAsnGlyLeuProIleThrHisGlyLeuTy

CAAGCGCACATCCCGCTACCCGAAGGAGTTAGAACTGCTG        7320
rLysArgThrSerArgTyrProLysGluLeuGluLeuLeu

GTCAGTCGGCGGTCACCCTGTGGCCGGCCAACAGCTCCC         7360
ValSerArgArgSerProCysGlyArgAlaAsnSerSerA

GAGTCTGGTGGACAGCAGCTTCCTGGCGGCGTGGTACA          7400
rgValTrpTrpAspSerSerPheLeuGlyGlyValValHi

TCTGGAGGCTGGGGAAGAGGTGGTGGTCCGCGTGCCTGGA        7440
sLeuGluAlaGlyGluGluValValValArgValProGly

AACCGCCTGGTCAGACCACGTGACGGCACCAGGTCCTATT        7480
AsnArgLeuValArgProArgAspGlyThrArgSerTyrP

TCGGAGCTTTCATGGTCTGAAGGCTGCGGTGACAATGTAT        7520
heGlyAlaPheMetVal
```

FIG. 4H

```
TTTGTGGAGGGACCTCTCCAGGACTCACCTCAAACCCAGC  7560
AATAGGGTTTGAAGTCCTCCCTTTAAGGAGCCCTGAACTC  7600
TGCAGTGCTCGGGCGGTGTTCACTGCTGACCTGCTTTGG   7640
GCAATCTTCAAATCAGAGACCTGGAGACTTGGGCGTGGA   7680
GCCCAGGAGCGAGGGTCAGCTCATTTGCCTGATATTCAG   7720
GAAGAAAGAATCAAGCTGGGGTATTTATGCTTCTGATGCA  7760
AACACTGAGATTTCGGCTTTCTGGGTTTTGAGCTGGAGGC  7800
AAGAAACCTTCCCAGAGTGTCATCAGGACCATGTTGGCAG  7840
GACTTGGGCTCCAGACTTGCCACCACACTCTGCCTCTC    7880
CCATCCATCCGCTGCATTGGTTTCCAGCCACCAAAACAGC  7920
ACTGGCCCCCTGGCTGCAACTGGCCAGGTACGAGCTTCTG  7960
AGCACCTACATTCCTCAGGACATCTTGATGAGATCTCAG   8000
TACTCAGTCCAATGCGCAGCAGCGACAGACATGCCAGGAA  8040
TGGTTGGTCAGAAGGGAAGGGAGGAAAGGGAGGAAAGAAC  8080
GGAATGCACAAGAGAAGCGGGGAAAACAAGACCAAAACAA  8120
AACAGCAACAACAAAGCGGCAGGGAAGAAGTTGACACCCT  8160
TGGGGATACTTTAGTCAACACACTTAGAACAGATTGTGCC  8200
AGCCTGTTGGATTCCTGGAGTTGATGGATCGTGGGAAG    8240
GCACAATGGGGAGCAAGTGGGCTTCGGTTATGGCTCAGTG  8280
GGTAAAGTGCAATTATGGGATCTGAGTTTGAATCCCTGG   8320
TACCCATATAAAGACACAGATGCGGTGATGGGCACTTGTG  8360
ACAATGAGATCATCAATAGGGAATGGAGACAGGAGGACC   8400
TCTGGGGTTCACTGGCCAGGCAGTCTAGCTGAATCAAAGA  8440
GCTCCAAGTTCAGTCGATAGCTCCTGAAGATGACAACTGA  8480
GGCTATTCTCCAAACCCCACACGCAGGACACATGCGTAA   8520
TAAATAAAATTTTAAAAATATTAAATAATAGTGTTTGAGA  8560
GGCACTTTATATGTTCTAATCATTTGTGCTTTTGTTTATT  8600
TGTTCAGGTTTGTTTGTTTGTTTGTTGGAAGACAGGGTC   8640
TCAAGTAGCCCAGGCTAGCTTTGAACTATATATTTCATAT  8680
```

FIG. 41

```
ATTTTGAGGCAGTCTTATGCCTTTTATCTAGGTTTTCTTG   8720
GCATCTAAAGCTATAGCTGTGTGTTACTCCAATGGAACAT   8760
CTGGGCAGTTACCCAGCACCTTCAAATGCAGAGCCCACAC   8800
CTGATAGGGTCGGGCTCGCCCTGCTCAGGGTCGCTGCTA    8840
GTCCAAGCCAGTCCAAGCGGACTTCCCGCGTCCTGTCCTT   8880
GCAACCCTGGTGGGAGGTGGAAAAGCCCCCAAATACCCAG   8920
TCTCACCCTCCATCGGAGTTTCCTTTATGCTTATCACGGC   8960
CTGTTTCCGTGTCTTTGATGAGACCAAGGTGTGGGACAG    9000
TATATTTATAAAAGCCACCAGCAGTTTCCGCTGTAAGGA    9040
AAAAAAAATCACTCTAGA   9058
```

| FIG. 6A |
| FIG. 6B |

```
CCTGACCCTGGGCTTCTGAGCCTCAGCTGCTCTGGCATGG    40
                                       MetG

AGAGTGTGGTACAGCCTTCAGTGTTTGTGGTGGATGGACA    80
luSerValValGlnProSerValPheValValAspGlyGl

GACAGACATCCCATTCAGGCGGCTGGACAGAACCACAGG    120
nThrAspIleProPheArgArgLeuGlyGlnAsnHisArg

AGACGGCACTGCGGCACTGTCCAGGTCAGCCTGGCCCTGC    160
ArgArgHisCysGlyThrValGlnValSerLeuAlaLeuL

TGCTGCTGCTGGGTGCTGGGCTGGCCACTGAGGGCTGGTT    200
euLeuLeuLeuGlyAlaGlyLeuAlaThrGluGlyTrpPh

TCTCCTGAGACTGCATCAGCGTCTTGGGACATAGTAGCT    240
eLeuLeuArgLeuHisGlnArgLeuGlyAspIleValAla

CATCTGCCAGATGGAGGCAAAGGCTCCTGGGAGAAGCTGA    280
HisLeuProAspGlyGlyLysGlySerTrpGluLysLeuI

TACAAGATCAACGATCTCACCAGCCCAACCCAGCAGCACA    320
leGlnAspGlnArgSerHisGlnProAsnProAlaAlaHi

TCTCACAGGAGCTAACGCCAGCTTGATAGGCATTGGTGGA    360
sLeuThrGlyAlaAsnAlaSerLeuIleGlyIleGlyGly

CCTCTGTTATGGAGACACAACTTGGCCTGGCCTTCCTGA    400
ProLeuLeuTrpGluThrGlnLeuGlyLeuAlaPheLeuA
```

FIG. 6A

```
GGGGCCTGACGTATCATGATGGGCCCTGGTGACCACCGA    440
rgGlyLeuThrTyrHisAspGlyAlaLeuValThrThrGl

GGCTGGCTACTACTACGTGTACTCCAAAGTGCAGTTGAGT    480
uAlaGlyTyrTyrTyrValTyrSerLysValGlnLeuSer

GGTGTGGGCTGCCCCCAGGGGCTGGCCAATGGCCTCCCCA    520
GlyValGlyCysProGlnGlyLeuAlaAsnGlyLeuProI

TCACCCACGGGCTGTACAAGCGCACATCCCGATACCCCAA    560
leThrHisGlyLeuTyrLysArgThrSerArgTyrProLy

GGAGTTAGAACTGCTGGTCAGCCGGCGGTCACCTTGTGGC    600
sGluLeuGluLeuLeuValSerArgArgSerProCysGly

CGGGCCAACAGCTCCCGAGTCTGGTGGACAGTAGTTTCC    640
ArgAlaAsnSerSerArgValTrpTrpAspSerSerPheL

TCGGCGGAGTGGTACATCTGGAGGCCGGAGAAGAGGTGGT    680
euGlyGlyValValHisLeuGluAlaGlyGluGluValVa

GGTCCGCGTGCCTGGAAACCGCCTGGTCAGACCACGTGAT    720
lValArgValProGlyAsnArgLeuValArgProArgAsp

GGCACGAGGTCCTATTTCGGAGCTTTCATGATCTGAAGGC    760
GlyThrArgSerTyrPheGlyAlaPheMetIle

TATGACGACAATGGATTTTGTGGA    784
```

FIG. 6B

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
        (A) LENGTH: 240
        (B) TYPE: Amino acid
        (D) TOPOLOGY: Linear (ii) MOLECULE TYPE: Protein (xi) SEQUENCE DESCRIPTION: SEQ ID NO: 1:

```
Met Glu Ser Val Val Arg Pro Ser Val Phe Val Val Asp Gly Gln
 1               5                  10                  15

Thr Asp Ile Pro Phe Thr Arg Leu Gly Arg Ser His Arg Arg Gln Ser
                20                  25                  30

Cys Ser Val Ala Arg Val Gly Leu Gly Leu Leu Leu Leu Leu Met Gly
                35                  40                  45

Ala Gly Leu Ala Val Gln Gly Trp Phe Leu Leu Gln Leu His Trp Arg
        50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
                100                 105                 110

Leu Trp Glu Thr Gln Leu Gly Leu Ala Phe Leu Arg Gly Leu Ser Tyr
            115                 120                 125

His Asp Gly Ala Leu Val Val Thr Lys Ala Gly Tyr Tyr Tyr Ile Tyr
        130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Lys Val Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240
```

(2) INFORMATION FOR SEQ ID NO: 2:

(i) SEQUENCE CHARACTERISTICS:

(A) LENGTH: 239
        (B) TYPE: Amino acid
        (D) TOPOLOGY: Linear (ii) MOLECULE TYPE: Protein (xi) SEQUENCE DESCRIPTION: SEQ ID NO: 2:

Met Glu Ser Val Val Gln Pro Ser Val Phe Val Val Asp Gly Gln Thr
1               5                   10                  15

Asp Ile Pro Phe Arg Arg Leu Glu Gln Asn His Arg Arg Arg Arg Cys
                20                  25                  30

Gly Thr Val Gln Val Ser Leu Ala Leu Val Leu Leu Leu Gly Ala Gly
            35                  40                  45

Leu Ala Thr Gln Gly Trp Phe Leu Leu Arg Leu His Gln Arg Leu Gly
        50                  55                  60

Asp Ile Val Ala His Leu Pro Asp Gly Gly Lys Gly Ser Trp Glu Lys
65                  70                  75                  80

Leu Ile Gln Asp Gln Arg Ser His Gln Ala Asn Pro Ala Ala His Leu
                85                  90                  95

Thr Gly Ala Asn Ala Ser Leu Ile Gly Ile Gly Gly Pro Leu Leu Trp
            100                 105                 110

Glu Thr Arg Leu Gly Leu Ala Phe Leu Arg Gly Leu Thr Tyr His Asp
        115                 120                 125

Gly Ala Leu Val Thr Met Glu Pro Gly Tyr Tyr Tyr Val Tyr Ser Lys
    130                 135                 140

Val Gln Leu Ser Gly Val Gly Cys Pro Gln Gly Leu Ala Asn Gly Leu
145                 150                 155                 160

Pro Ile Thr His Gly Leu Tyr Lys Arg Thr Ser Arg Tyr Pro Lys Glu
                165                 170                 175

Leu Glu Leu Leu Val Ser Arg Arg Ser Pro Cys Gly Arg Ala Asn Ser
            180                 185                 190

Ser Arg Val Trp Trp Asp Ser Ser Phe Leu Gly Gly Val Val His Leu
        195                 200                 205

Glu Ala Gly Glu Glu Val Val Val Arg Val Pro Gly Asn Arg Leu Val
    210                 215                 220

Arg Pro Arg Asp Gly Thr Arg Ser Tyr Phe Gly Ala Phe Met Val
225                 230                 235

(2) INFORMATION FOR SEQ ID NO: 3:

(i) SEQUENCE CHARACTERISTICS:
        (A) LENGTH: 239
        (B) TYPE: Amino acid
        (D) TOPOLOGY: Linear (ii) MOLECULE TYPE: Protein (xi) SEQUENCE DESCRIPTION: SEQ ID NO: 3:

Met Glu Ser Val Val Gln Pro Ser Val Phe Val Val Asp Gly Gln Thr
1               5                   10                  15

Asp Ile Pro Phe Arg Arg Leu Gly Gln Asn His Arg Arg Arg His Cys
                20                  25                  30

Gly Thr Val Gln Val Ser Leu Ala Leu Leu Leu Leu Leu Gly Ala Gly
            35                  40                  45

Leu Ala Thr Glu Gly Trp Phe Leu Leu Arg Leu His Gln Arg Leu Gly
        50                  55                  60

Asp Ile Val Ala His Leu Pro Asp Gly Gly Lys Gly Ser Trp Glu Lys
65                  70                  75                  80

```
Leu Ile Gln Asp Gln Arg Ser His Gln Pro Asn Pro Ala Ala His Leu
                85                  90                  95

Thr Gly Ala Asn Ala Ser Leu Ile Gly Ile Gly Gly Pro Leu Leu Trp
            100                 105                 110

Glu Thr Gln Leu Gly Leu Ala Phe Leu Arg Gly Leu Thr Tyr His Asp
        115                 120                 125

Gly Ala Leu Val Thr Thr Glu Ala Gly Tyr Tyr Val Tyr Ser Lys
    130                 135                 140

Val Gln Leu Ser Gly Val Gly Cys Pro Gln Gly Leu Ala Asn Gly Leu
145                 150                 155                 160

Pro Ile Thr His Gly Leu Tyr Lys Arg Thr Ser Arg Tyr Pro Lys Glu
                165                 170                 175

Leu Glu Leu Leu Val Ser Arg Arg Ser Pro Cys Gly Arg Ala Asn Ser
            180                 185                 190

Ser Arg Val Trp Trp Asp Ser Ser Phe Leu Gly Gly Val Val His Leu
        195                 200                 205

Glu Ala Gly Glu Glu Val Val Val Arg Val Pro Gly Asn Arg Leu Val
    210                 215                 220

Arg Pro Arg Asp Gly Thr Arg Ser Tyr Phe Gly Ala Phe Met Ile
225                 230                 235

(2) INFORMATION FOR SEQ ID NO: 4:

(i) SEQUENCE CHARACTERISTICS:
        (A) LENGTH: 720 base pairs
        (B) TYPE: Nucleic acid
        (C) STRANDEDNESS: Double
        (D) TOPOLOGY: Linear (ii) MOLECULE TYPE: cDNA (xi) SEQUENCE DESCRIPTION: SEQ ID NO: 4:

ATGGAGGAGA GTGTCGTACG GCCCTCAGTG TTTGTGGTGG ATGGACAGAC CGACATCCCA      60

TTCACGAGGC TGGGACGAAG CCACCGGAGA CAGTCGTGCA GTGTGGCCCG GGTGGGTCTG     120

GGTCTCTTGC TGTTGCTGAT GGGGGCTGGG CTGGCCGTCC AAGGCTGGTT CCTCCTGCAG     180

CTGCACTGGC GTCTAGGAGA GATGGTCACC CGCCTGCCTG ACGGACCTGC AGGCTCCTGG     240

GAGCAGCTGA TACAAGAGCG AAGGTCTCAC GAGGTCAACC CAGCAGCGCA TCTCACAGGG     300

GCCAACTCCA GCTTGACCGG CAGCGGGGGG CCGCTGTTAT GGGAGACTCA GCTGGGCCTG     360

GCCTTCCTGA GGGGCCTCAG CTACCACGAT GGGGCCCTTG TGGTCACCAA AGCTGGCTAC     420

TACTACATCT ACTCCAAGGT GCAGCTGGGC GGTGTGGGCT GCCCGCTGGG CCTGGCCAGC     480

ACCATCACCC ACGGCCTCTA CAAGCGCACA CCCCGCTACC CCGAGGAGCT GGAGCTGTTG     540

GTCAGCCAGC AGTCACCCTG CGGACGGGCC ACCAGCAGCT CCCGGGTCTG GTGGGACAGC     600

AGCTTCCTGG GTGGTGTGGT ACACCTGGAG GCTGGGGAGA AGGTGGTCGT CCGTGTGCTG     660

GATGAACGCC TGGTTCGACT GCGTGATGGT ACCCGGTCTT ACTTCGGGGC TTTCATGGTG     720

(2) INFORMATION FOR SEQ ID NO: 5:

(i) SEQUENCE CHARACTERISTICS:
        (A) LENGTH: 1491
        (B) TYPE: Nucleic acid
        (C) STRANDEDNESS: Double
        (D) TOPOLOGY: Linear (ii) MOLECULE TYPE: cDNA
```

(xi) SEQUENCE DESCRIPTION: SEQ ID NO: 5:

```
CGAGACTCCA TCTCAAAAAC AAAACAAATA AACGAACAAA AAAACCCACA ACGTATTATT      60

TTCTTGTTTA CGAGGTTTCT TGTCTCTCTG GCTCCACCAG AAGAGGAGCA GGGACCCTTC     120

TTGCTGTTGT TCATTGCTGC ATCCCCCACA CCGAGAGCAG AGCCTGGCAT GGGCAGAAAG     180

TCCTCAGTCG ATATTTGGTG GCCCCAAGCG AATGAAGCAT CCAAGAAGGG AAAGCTGGGG     240

GCTCCCCACT GCACTTGCCA CCTGAGTCAC ATTTTCAGAA GCCTCTGGAA AGTCGTGCAC     300

AGCCCAGGAG TGTTGAGCAA TTTCGGTTTC CTCTGAGGTT GAAGGACCCA GGCGTGTCAG     360

CCCTGCTCCA GACACCTTGG GCATGGAGGA GAGTGTCGTA CGGCCCTCAG TGTTTGTGGT     420

GGATGGACAG ACCGACATCC CATTCACGAG GCTGGGACGA AGCCACCGGA GACAGTCGTG     480

CAGTGTGGCC CGGGTGGGTC TGGGTCTCTT GCTGTTGCTG ATGGGGCTG GGCTGGCCGT      540

CCAAGGCTGG TTCCTCCTGC AGCTGCACTG GCGTCTAGGA GAGATGGTCA CCCGCCTGCC     600

TGACGGACCT GCAGGCTCCT GGGAGCAGCT GATACAAGAG CGAAGGTCTC ACGAGGTCAA     660

CCCAGCAGCG CATCTCACAG GGGCCAACTC CAGCTTGACC GGCAGCGGGG GGCCGCTGTT     720

ATGGGAGACT CAGCTGGGCC TGGCCTTCCT GAGGGGCCTC AGCTACCACG ATGGGGCCCT     780

TGTGGTCACC AAAGCTGGCT ACTACTACAT CTACTCCAAG GTGCAGCTGG GCGGTGTGGG     840

CTGCCCGCTG GGCCTGGCCA GCACCATCAC CCACGGCCTC TACAAGCGCA CACCCCGCTA     900

CCCCGAGGAG CTGGAGCTGT TGGTCAGCCA GCAGTCACCC TGCGGACGGG CCACCAGCAG     960

CTCCCGGGTC TGGTGGGACA GCAGCTTCCT GGGTGGTGTG GTACACCTGG AGGCTGGGGA    1020

GAAGGTGGTC GTCCGTGTGC TGGATGAACG CCTGGTTCGA CTGCGTGATG GTACCCGGTC    1080

TTACTTCGGG GCTTTCATGG TGTGAAGGAA GGAGCGTGGT GCATTGGACA TGGGTCTGAC    1140

ACGTGGAGAA CTCAGAGGGT GCCTCAGGGG AAAGAAAACT CACGAAGCAG AGGCTGGGCG    1200

TGGTGGCTCT CGCCTGTAAT CCCAGCACTT TGGGAGGCCA AGGCAGGCGG ATCACCTGAG    1260

GTCAGGAGTT CGAGACCAGC CTGGCTAACA TGGCAAAACC CCATCTCTAC TAAAAATACA    1320

AAAATTAGCC GGACGTGGTG GTGCCTGCCT GTAATCCAGC TACTCAGGAG CTGAGGCAG     1380

GATAATTTTG CTTAAACCCG GGAGGCGGAG GTTGCAGTGA GCCGAGATCA CCACTGCA      1440

CTCCAACCTG GGAAACGCAG TGAGACTGTG CCTCAAAAAA AAAAAAAAA A              1491
```

(2) INFORMATION FOR SEQ ID NO: 6:

(i) SEQUENCE CHARACTERISTICS:
        (A) LENGTH: 1353
        (B) TYPE: Nucleic acid
        (C) STRANDEDNESS: Double
        (D) TOPOLOGY: Linear (ii) MOLECULE TYPE: cDNA (xi) SEQUENCE DESCRIPTION: SEQ ID NO: 6:

```
CCCACGCGTC CGCCCACGCG TCCGCTGAGG TTGAAGGACC CAGGCGTGTC AGCCCTGCTC      60

CAGACACCTT GGGCATGGAG GAGAGTGTCG TACGGCCCTC AGTGTTTGTG GTGGATGGAC     120

AGACCGACAT CCCATTCACG AGGCTGGGAC GAAGCCACCG AGACAGTCG TGCAGTGTGG      180

CCCGGGTGGG TCTGGGTCTC TTGCTGTTGC TGATGGGGGC TGGGCTGGCC GTCCAAGGCT     240

GGTTCCTCCT GCAGCTGCAC TGGCGTCTAG GAGAGATGGT CACCCGCCTG CCTGACGGAC     300

CTGCAGGCTC CTGGGAGCAG CTGATACAAG AGCGAAGGTC TCACGAGGTC AACCCAGCAG     360

CGCATCTCAC AGGGGCCAAC TCCAGCTTGA CCGGCAGCGG GGGCCGCTG TTATGGGAGA      420
```

```
CTCAGCTGGG CCTGGCCTTC CTGAGGGGCC TCAGCTACCA CGATGGGGCC CTTGTGGTCA      480

CCAAAGCTGG CTACTACTAC ATCTACTCCA AGGTGCAGCT GGGCGGTGTG GGCTGCCCGC      540

TGGGCCTGGC CAGCACCATC ACCCACGGCC TCTACAAGCG CACACCCCGC TACCCCGAGG      600

AGCTGGAGCT GTTGGTCAGC CAGCAGTCAC CCTGCGGACG GGCCACCAGC AGCTCCCGGG      660

TCTGGTGGGA CAGCAGCTTC CTGGGTGGTG TGGTACACCT GGAGGCTGGG GAGAAGGTGG      720

TCGTCCGTGT GCTGGATGAA CGCCTGGTTC GACTGCGTGA TGGTACCCGG TCTTACTTCG      780

GGGCTTTCAT GGTGTGAAGG AAGGAGCGTG GTGCATTGGA CATGGGTCTG ACACGTGGAG      840

AACTCAGAGG GTGCCTCAGG GGAAAGAAAA CTCACGAAGC AGAGGCTGGG ATTACAGGCG      900

TGAGCCACTG TTCCCAGCAG GAATTTCTTT TTTATAGTAT TGGATAAAGT TTGGTGTTTT      960

TACAGAGGAG AAGCAATGGG TCTTAGCTCT TTCTCTATTA TGTTATCATC CTCCCTTTTT     1020

TGTACAATAT GTTGTTTACC TGAAAGGAAG GTTTCTATTC GTTGGTTGTG GACCTGGACA     1080

AAGTCCAAGT CTGTGGAACT TAAAACCTTG AAGGTCTGTC ATAGGACTCT GGACAATCTC     1140

ACACCTTAGC TATTCCCAGG GAACCCCAGG GGGCAACTGA CATTGCTCCA AGATGTTCTC     1200

CTGATGTAGC TTGAGATATA AAGGAAAGGC CCTGCACAGG TGGCTGTTTC TTGTCTGTTA     1260

TGTCAGAGGA ACAGTCCTGT TCAGAAAGGG GCTCTTCTGA GCAGAAATGG CTAATAAACT     1320

TTGTGCTGAT CTGGAAAAAA AAAAAAAAA AAA                                   1353

(2) INFORMATION FOR SEQ ID NO: 7:

(i) SEQUENCE CHARACTERISTICS:
        (A) LENGTH: 717
        (B) TYPE: Nucleic acid
        (C) STRANDEDNESS: Double
        (D) TOPOLOGY: Linear (ii) MOLECULE TYPE: cDNA (xi) SEQUENCE DESCRIPTION: SEQ ID NO: 7:

ATGGAGAGTG TGGTACAGCC TTCAGTGTTT GTGGTGGATG GACAGACGGA CATCCCATTC       60

AGGCGGCTGG AACAGAACCA CCGGAGACGG CGCTGTGGCA CTGTCCAGGT CAGCCTGGCC      120

CTGGTGCTGC TGCTAGGTGC TGGGCTGGCC ACTCAGGGCT GGTTTCTCCT GAGACTGCAT      180

CAACGTCTTG GAGACATAGT AGCTCATCTG CCAGATGGAG GCAAAGGCTC CTGGGAGAAG      240

CTGATACAAG ATCAACGATC TCACCAGGCC AACCCAGCAG CACATCTTAC AGGAGCCAAC      300

GCCAGCTTGA TAGGTATTGG TGGACCTCTG TTATGGGAGA CACGACTTGG CCTGGCCTTC      360

TTGAGGGGCT TGACGTATCA TGATGGGGCC CTGGTGACCA TGGAGCCCGG TTACTACTAT      420

GTGTACTCCA AAGTGCAGCT GAGCGGCGTG GGCTGCCCCC AGGGGCTGGC CAATGGCCTC      480

CCCATCACCC ATGGACTATA CAAGCGCACA TCCCGCTACC CGAAGGAGTT AGAACTGCTG      540

GTCAGTCGGC GGTCACCCTG TGGCCGGGCC AACAGCTCCC GAGTCTGGTG GGACAGCAGC      600

TTCCTGGGCG GCGTGGTACA TCTGGAGGCT GGGGAAGAGG TGGTGGTCCG CGTGCCTGGA      660

AACCGCCTGG TCAGACCACG TGACGGCACC AGGTCCTATT TCGGAGCTTT CATGGTC        717

(2) INFORMATION FOR SEQ ID NO: 8:

(i) SEQUENCE CHARACTERISTICS:
        (A) LENGTH: 795
        (B) TYPE: Nucleic acid
        (C) STRANDEDNESS: Double
        (D) TOPOLOGY: Linear (ii) MOLECULE TYPE: cDNA
```

(xi) SEQUENCE DESCRIPTION: SEQ ID NO: 8:

```
TCTGCTCTGG CATGGAGAGT GTGGTACAGC CTTCAGTGTT TGTGGTGGAT GGACAGACGG      60
ACATCCCATT CAGGCGGCTG GAACAGAACC ACCGGAGACG GCGCTGTGGC ACTGTCCAGG     120
TCAGCCTGGC CCTGGTGCTG CTGCTAGGTG CTGGGCTGGC CACTCAGGGC TGGTTTCTCC     180
TGAGACTGCA TCAACGTCTT GGAGACATAG TAGCTCATCT GCCAGATGGA GGCAAAGGCT     240
CCTGGGAGAA GCTGATACAA GATCAACGAT CTCACCAGGC CAACCCAGCA GCACATCTTA     300
CAGGAGCCAA CGCCAGCTTG ATAGGTATTG GTGGACCTCT GTTATGGGAG ACACGACTTG     360
GCCTGGCCTT CTTGAGGGGC TTGACGTATC ATGATGGGGC CCTGGTGACC ATGGAGCCCG     420
GTTACTACTA TGTGTACTCC AAAGTGCAGC TGAGCGGCGT GGGCTGCCCC CAGGGGCTGG     480
CCAATGGCCT CCCCATCACC CATGGACTAT ACAAGCGCAC ATCCCGCTAC CCGAAGGAGT     540
TAGAACTGCT GGTCAGTCGG CGGTCACCCT GTGGCCGGGC CAACAGCTCC CGAGTCTGGT     600
GGGACAGCAG CTTCCTGGGC GGCGTGGTAC ATCTGGAGGC TGGGGAAGAG GTGGTGGTCC     660
GCGTGCCTGG AAACCGCCTG GTCAGACCAC GTGACGGCAC CAGGTCCTAT TTCGGAGCTT     720
TCATGGTCTG AAGGCTGCGG TGACAATGTA TTTTGTGGAG GGACCTCTCC AGGACTCACC     780
TCAAACCCAG CAATA                                                     795
```

(2) INFORMATION FOR SEQ ID NO: 9:

(i) SEQUENCE CHARACTERISTICS:
        (A) LENGTH: 9058
        (B) TYPE: Nucleic acid
        (C) STRANDEDNESS: Double
        (D) TOPOLOGY: Linear (ii) MOLECULE TYPE: genomic DNA (xi) SEQUENCE DESCRIPTION: SEQ ID NO: 9:

```
TCTAGATTGC ATTAACAGAG AGAAGACCCT GAGTATGGGT GGAGTCATCT CAGGGCTGAG      60
GTCCTGGGCT GAATGAAAAT GACAGAGTGA GCAGAGCACC CGTGTTCTTT GGTTTCTGCT     120
ACCTCACTGT GGATTTGACA TGACCAACTG CCTCGTGCTA CCTCCCCTCT CCCCACTTTG     180
ACTTCTCCAC TGTGATAGAC ACTTCTCACT ATGAGCAAG ATTTTTCTTC CTCCCAGTCT      240
TAGTTGGGGT TTCTACTGCT GTGCTAAAAC ACCATGACCA AAAGCAACTT GGAGAGAAGA     300
GGGTTTATTT CAGTTACATT TCCAGGTTAT AGTTCATCAC TGAATAAAAT CAGGACAGGA     360
ATTCTAATTG TGCAGGATCC TGGAGGCAGT AGGTGACGCA GAGGCCATGA GGATGCTGCT     420
TGCTAGTTTG CTCCCCATGG CTTGCTTGCT CAGCCTGCTT TCTTATAGAA CCCAGGATCA     480
TCAGCCCAGG GGATGGTGCC ATCCACAGTG GACTGGGCCC TTCCGCATCA ATCACTAATG     540
GAGAAAATGC CCCACGGGCT TAAATGCATC CTGATCTTAT GGAGGCATTT TTTTTTCAAC     600
TGAGGCTCCC TCCTCTCAGA TGATTTTTGC TCGTGTCAAG TTGACATAAA ACTATCCAGC     660
ACCCTGTACC CTTTGTCATC TTGACACACA AACACAACAC TAGTAAGCCA CAACCTTTCC     720
TTTCTTGTCA TCTCCAAGAT CAAACATTAA TATCAACGTC ACAACATAAA AACATTTTGT     780
GGGCTAGAGA GATGGCTTGG AGGCTAAGAG CACTGGCTGT CCTTCAAGAA AATGAGCAAT     840
TCCCAGCACC CACACGGCAG CTCACAACTG TCTTTAATTC ATTTTCCAGG GGATCCAAAT     900
CCCTCACACA TGCAAGCAAA ACACTAATGT ACAGAAAATA GAAATAAATA AATTTTTAAA     960
CATTTTGCAA ACTTAAAAAA AAAAAAGTC CCACCACTTT ACAAATTCAA ACAGGTTAAA     1020
ATTTAGTGTC TTTAAAACTC CAAAGTTTAA AGTTGAAAAA CCTTTAAAAT CTAAAATATT    1080
```

```
TTAAAAGCTA GCCTCTCAGC TGTGGGATCC TATAACATTG AAAACAAGCT TAATACTTCC    1140

TTATTTCAAG AGGGAAGAAC CACGGCACAG TCAACAACCT GAACAAGCAA AACCAAATAC    1200

CAGCTGTGTA AATAATTCGA TTTCCAGTGT CTGGGATTCA AACATGATCT TCTGGGCTCC    1260

TCCAAAGGTC CTGAGTGCCT TCTCTGGTGC TGCCCTATGC AGCCCTCACA TCTTGTCTTC    1320

TAGGCTGGGG CTGGCTCCAC CCCAAGGCTG CTGCTGCTGC TGCTGCTGCT GGTGATCATC    1380

CCAAGCACC AGCATCTTCA AAATACTGTG GTCTTCTGCT GCCACGGAGG CTGCACTTTC     1440

ACCAACAGCC TCTCCTGGTC CCACACAGTG CCATGCCTCA GCTTCTCTCC ATGGCCTCCT    1500

TATCCTTCCA AACCCAGCAT CATCTGAGGA TAACCTTGTT CACCTTAACA GCACAGCTTC    1560

TGTGTACTGG TTCTCTCAGG AAACACTCCC CAGATTTCAC CTCAGTGATG CAGGTCTCTT    1620

CTAAATCACG GCCAGTTCTG CAGAACAAGC TAAGCAGAAC TAAGAATCTC ATTTCAAATA    1680

TCAAACATCC CCAATGCTCT CCTTGTTGTT GTTTTTGTTT TAAAATAGAA TCCCTTTATA    1740

GTTCTTGCTC TCTTGGAACT CACTATGTAG AATAGGCTGG TTTTGATCTC ACAGGAGATC    1800

CATCTGCCTC TGCCTCCCAA AGGTGTGTAC TACCCTACCC AGGAAATCGT GGTGGTCTTT    1860

AAGAAACTCT CAAACTTCCC TCTGTAATTT CACAAGGCAG GCCTCCATCA TCTGCCGTAT    1920

TCTCAGCATT TTGAACTTCC AAGCTCCCAC AGAACAGCCC ACTGAGCTCT GCATGGAACA    1980

GTTTCTCCAG TCCAAAGTTG AGAGGCCGTA CAATCTTCTC AATACCATAG TCAGGTCTTT    2040

CCTATTCCTA ACCCACACCT GATTCCAATT TGTGTCTTGG CTAGGATTTC TATTGCTGTC    2100

ATAAAACAGC ATGATCAAAA GCAACCTCAG CTTACACTTT CAGGTCACAC CCCATCCACT    2160

GAGGGAGGTC AGGACAGGAA CCTGGAGACA GGAGCTGATG CAGAGACTAT GGAAGAACAC    2220

TGCTTACTGG CTTGTGTCCT ATGACTTGTT CAGCCTGCTT TCTTATAGAA CTCAGGAATG    2280

CCAGTGCAGG GAAGGCCCAG TTTACAGTGA GCACGGCCTC CCACAAGCCA ATCTGTTGGG    2340

GGTGTTTTCT CCATTGAAGT TTCCTCTTCC AAAATGAATG TAGCTTGTGT CAAATTGACA    2400

CTGGCCAGCA CAGACCATGA GAGATTAGAG AACGCTTCCA GGCAGATCCT TTATGGAGTA    2460

TCAGATACTC CGGGCTGCTG AGTAATTTGC ACAGTTCCAG GAATGGACCT GAGTTGGGCA    2520

ACAGCAAAGA GATGAAGAAA CGACAAACAC AGACATCCAG GAATCCTGGG GTCATGTGAT    2580

CTGGGCCTTC TGCACACGAG TTCTCTTAGC ACGTTATTAT ATAGAGTCGA GTGGAGAAGT    2640

GGGGTTATTG CCTACCACTG AAAAAGGCAA CTTATTACAT ACAGTTAAGC AAGGAGGCAG    2700

GGTTTATATG CACAATGGGA TGGGAAGGC AGGTTGAGTT AGTCTCCATA AGAACTGTCC     2760

CTGGAAGGGA GCTATGTTCA TGCGTCAGCA CTCAAGGGGG AGGATGGTGA ACACATTCTA    2820

CACACACTGG CGACATGCAC ATCCATGCGT GGACCAGAAG AGAAGGCTAT GTTTCCCTCT    2880

GGGTCTGAGG CTCTGGAGTT GTTGACAAGC TCATGTCAAC AGCACACATC CCTTCAGCAC    2940

CTCACAGACC TGGGCTTCCT CTGAAGGGCT CTGTTGCTGA GGCAGGTGGA TGGGTGGGTC    3000

CTGCAGGGGG ACAGGAGTCT CAGCAGTACT TTCCCCTGGA CCCTTGGTTA GAGAACCCAT    3060

GAATCAGCAG CGTGGCAGAG CACTGGGGTT CTGTGGTCAC AGCATCGCCA GCCCTGTGTC    3120

AAGACAAACA CTACAGCATG GGGCCATTG ACATTGAGAA GGGCGCTGG TGATTCTTAT      3180

AACTGAACCC CCAAGTCTTC AGTATCTGGG AGGGTGTCTG ATGGGGGTAA GCTCCAAGCT    3240

GAAGATTTGG GGACAAGGTG GTATCTGAAA ATCTACCCCA GCACCGTCTC CAGTGGACAC    3300

ACATATGAAC ACATCTGAGG TTCATGTGTG CATGTGCTAA TAGATGATAG ACACTGTAGT    3360

GTGTGTGTGT GTGTGTGTCC ATATATGGAC CTGCACACAC ATCAGGAAAT GCCTGTGTGC    3420
```

```
TTGTTCCAGC ACTTGCAGAC ACATATCAGA ACATCTACAC CTGTGTGCAC ACATCCACGA      3480

ACCGTGCATC TGTACAAGCA CCTGCACCCA TATGCACAGA CTAAAGCAAA CACAGAGGCC      3540

TCTGCTTGTC AGCGCGTGCA AATGCAGGTG CGGTGCAAGA TGCTTGCATG GAACCCACAG      3600

AAGTTCTTTT GAGGGAAACA AAAGCCACCA AGTACATCGG AGCAGGGGCT GCCCCATCCA      3660

TCCCACCTGA GTCACATTTT CTGGAAAGTG TGAGCTATGG TGGCCTCAGT GAGAGTGATC      3720

GACCGGGGGC TGGCCTTCTG GGGGCACAGG AAGAAGAGGA GGTACGTGAG GAAAGGGGAG      3780

GCACCAGACT TCAGCTTTAA AGTGAGTCCT AGGGGTGACA GGAACCTTTT GCAGTTTGCA      3840

CAGCCCGAGC GTGTTGGGCA ATTGTGGTTT CCTCCGGAGA GGAGGAACTC AGGCTTGCCA      3900

ACCCTTTCCC CTGGGCTTCG GAGCCTCAGC TGCTCTGGCA TGGAGAGTGT GGTACAGCCT      3960

TCAGTGTTTG TGGTGGATGG ACAGACGGAC ATCCCATTCA GGCGGCTGGA ACAGAACCAC      4020

CGGAGACGGC GCTGTGGCAC TGTCCAGGTC AGCCTGGCCC TGGTGCTGCT GCTAGGTGCT      4080

GGGCTGGCCA CTCAGGGCTG GTTTCTCCTG AGACTGCATC AACGTCTTGG AGACATAGTA      4140

GCTCATCTGC CAGTAAGTGG GGCTTGGGGA ACCAGCGAGT CTTCTCCAGT ACCTGTCCCT      4200

TTATGGTTGT GTATTGTGTG CTAGAACCCA GGGCTTCGGT TAGCCTGTCT CTCTGACCCT      4260

CAGTCTTCTC ATCTTTACAT GAGGATCTGA TACACGTGCA GTGCCCGGCA GTTTCCTTGG      4320

GATTCACCTA CTCGGTTGTT GTTTCCAGCC CAAACCTTTG TCCACCACTG GCTTCATGGT      4380

CACCCTGCTT CACTCGCAGC TCTCTCATGT GCTTGCTCTA CTGTTTCCTT TCAGACAAGC      4440

CATGGGTGTG TCACAGTATG CTCCCGAGTC TTTGCCTATA TTTTCTTTTT AAGTTTTTTT      4500

TTTTAATTAC ATTTACTTAT TTAGTGTGTA GACATGAAAA AGTATGCATG TGCCGCAGCA      4560

TGTATGTGGA ACACCTCTAT GGAATCACTT CTCTGTGCCT TCCTTTGTGG AGGGTCCTAG      4620

GGACTGAACT CAGGTAGCCA GGCTTGGCAG CAAGCACTTT TACCGCCTGA GCCCTCTCAC      4680

CGGCCCTCAA CTATCCAAAA ACCTCGAAAA CAGTTCCGAA ACAATTCTAG TCTCAAGCAT      4740

TTCAGACACT CGACTTGACT AGTTAATTCC TCATCCCAGC ACTTGGGCAG GGGAGGCAGA      4800

AGACTGAGGG AGTTCAAGGT CATCCTAGGC TATTTAGCAA GTCTGAGGCC AGACTGGGCT      4860

ACATGAGAGC CTATCTTGGA AATACAACAG ATCTAATTAG GTGTGTGCCC CTCCCCCTGC      4920

ATCTGTGTGT ATGTATGTGA TATGTGCATG TGTGGCTCTG CATACATGTC CATGGGTGGT      4980

GTCTGTGGCC ATGGCCAGAC AGTCTCATCA CCACATACCA GTGAGACTCG GAGCGGCATG      5040

TCCTTACCAA ACATCCCTGT CTGCATTTCA GGATGGAGGC AAAGGCTCCT GGGAGAAGCT      5100

GATACAAGGT GAGTTTGGGC CCCAGTCCCT TTGAAGCAGG TGGAATGGTT TCCGTTCAGC      5160

ACCTCCCCAC ACCAACTCTG GGTCATCACC CAGTGTCACA TTGTAGGCCT CGCAGGTGCC      5220

CCTCCCCCAG GGCCAGAGAA GCAGAAATCT GGGTCCAAAA GGGACAGAGC CTGACACAGG      5280

TAGCCTCAAT TGATGTGTGA GAAACTTCGG GTACACACAC ACTGAGACAT GCGTGCACAC      5340

ACACACATAC ACACACACAC ACACACACAC AATCCTCTTT TTGTCTCTAA CCTTTGACTC      5400

TCTTCCTCAG ATCAACGATC TCACCAGGCC AACCCAGCAG CACATCTTAC AGGTGAGAGG      5460

GACCCCAGAT CTTCACACGG AATGGGGTTT AGCATGTCCT GGGAGACTCA GATCTTTATA      5520

AGTTAGAGCA CTCGTTTATG CATTCATTTA GTGTGTCTTT AAATTTTTTT TGACATTTAC      5580

TTCTTTTTAT TCATTTATTA TTGCACATGT GCATGCCATA GTGTAGAGGT CAGAAAACTC      5640

TCAGGGGAAC GATTCTTTCC TTCCACCTTT TGGCCTCCGT GTACTGATCT CAGCCATCAG      5700

GCTTGGCTCT AAGTACCTTT ACTCTCTGCG CCATCTTGCC GGTCACTTTT TTTTTTCTCA      5760

GTGTTTACTA AAAACAGCC CAGAGAAGAG CCACAGGGAG CCATGTAAAG TCAACTCTTC      5820
```

-continued

```
ACCCTGCTAG TCATGGGGAC ACATCCCAAG GTCCTTGGAG GCCTCAGAAG ATGTTGGGAC    5880

TCAGACCTAC CACAGTTTAT ATTTGTTTGT TTGTTTGGTT GGTTGGTTGG TTGGTTGGTT    5940

GGTTGGTTGA TTGGTTGGTT GGTTTTGGTT TTGGAGACAG GGTCTCTCTG TGTAGCTTGG    6000

GCTGCCTGGG TAGACCTGCC TCTGTCCTGA GTACTGGAAT TAACAGGAAT TAACGACGTG    6060

GGCCACTACA CCCAGCTGTA TATACTGGTT TTTCTTTTGG CATAGACAGT TTAATTTATA    6120

ATTTAACAAG TAAGAAACTA ACAAGAATAC ACATAAAGTA TGCTGTAATT AAAAACTATT    6180

TTTGAAACAT GATGTGGGAG ATAGGGAGGT GGCTCCATGT GCAAATTGCT AGCCACTTTT    6240

GACTCAACAT CTGAGCCAAA AGCCAAACAC ACACTCCCGT GACAGTTACA GAGGCAGATT    6300

CAGACAGACA CACACTCCTG TGACAGTCAT GGAGACAGAG ACAGGCAGAG AGGTCCCTAG    6360

GACCTGCTGT CCAGCAGCCT TGACAAACAG GGGACTTCCA GGGTCAATAA GAGACTCTGC    6420

CTCAAAACTA AGGTGGACAG AGGTTGAAAC TGAGGAAGTT GCCTGGTTTT GACTTCTGGG    6480

CACACACACA CACACACACA CACATATATA TAACACATAC ATCACACACA TATACACAAA    6540

CATACAGTCA CACACACTTT TTGAGATAGA GTCTCATGTA GCCTAAACCG GCCTTGAACT    6600

CTTGATCCTC CAGACTCGAC GTCCCAAGAT CTGGATGTCA CCACTACACC TGATTTATTT    6660

GGTACTGGGG CTGGAATGTA CAGCCTTCGG CATGCTGGGC GAGTGTTCCA CCTCCTAAAT    6720

CCTAACCCCA TTTAAAAAAA ATTTTTTTGA CATTTCACTA GGAAGCTTCA ATACCTTGTG    6780

CCTCAGTTTC TTCTTTGGTA TTCAAGTGAC TTTGCTCCTC AGTGCTTCAG TGTCTACCCT    6840

TGCAGAAGGA GATGGGAATG AACGGAGTTA AGACACAACC ACCAAATTAC TTTGCTTGCT    6900

TTCCTGTATC TCAGTTTCTT CCCCCTGCAA GATAGGAATG GGCTGAGTCA ACCCAGACAA    6960

GCAGCCTACT ATGGTGGTGA AACCAGAGGG AACTAGCATA AGGTCACACA GAAAGGGTGG    7020

GCACAATGCT AACCGTGCTG ACGGGTTATC TTTCTCTCTC CTTTCCTCCC AGGAGCCAAC    7080

GCCAGCTTGA TAGGTATTGG TGGACCTCTG TTATGGAGA CACGACTTGG CCTGGCCTTC    7140

TTGAGGGGCT TGACGTATCA TGATGGGGCC CTGGTGACCA TGGAGCCCGG TTACTACTAT    7200

GTGTACTCCA AAGTGCAGCT GAGCGGCGTG GGCTGCCCCC AGGGGCTGGC CAATGGCCTC    7260

CCCATCACCC ATGGACTATA CAAGCGCACA TCCCGCTACC CGAAGGAGTT AGAACTGCTG    7320

GTCAGTCGGC GGTCACCCTG TGGCCGGGCC AACAGCTCCC GAGTCTGGTG GGACAGCAGC    7380

TTCCTGGGCG GCGTGGTACA TCTGGAGGCT GGGGAAGAGG TGGTGGTCCG CGTGCCTGGA    7440

AACCGCCTGG TCAGACCACG TGACGGCACC AGGTCCTATT TCGGAGCTTT CATGGTCTGA    7500

AGGCTGCGGT GACAATGTAT TTTGTGGAGG GACCTCTCCA GGACTCACCT CAAACCCAGC    7560

AATAGGGTTT GAAGTCCTCC CTTTAAGGAG CCCTGAACTC TGCAGTGCTC GGGGCGGTGT    7620

TCACTGCTGA CCTGCTTTGG GCAATCTTCA AATCAGAGAC CTGGAGACTT GGGGCGTGGA    7680

GCCCAGGAGC GAGGGGTCAG CTCATTTGCC TGATATTCAG GAAGAAAGAA TCAAGCTGGG    7740

GTATTTATGC TTCTGATGCA AACACTGAGA TTTCGGCTTT CTGGGTTTTG AGCTGGAGGC    7800

AAGAAACCTT CCCAGAGTGT CATCAGGACC ATGTTGGCAG GACTTGGGC TCCAGACTTG    7860

CCACCACACT CTGGCCTCTC CCATCCATCC GCTGCATTGG TTTCCAGCCA CCAAAACAGC    7920

ACTGGCCCCC TGGCTGCAAC TGGCCAGGTA CGAGCTTCTG AGCACCTACA TTCCTCAGGG    7980

ACATCTTGAT GAGATCTCAG TACTCAGTCC AATGCGCAGC AGCGACAGAC ATGCCAGGAA    8040

TGGTTGGTCA GAAGGGAAGG GAGGAAAGGG AGGAAAGAAC GGAATGCACA AGAGAAGGGG    8100

GGAAAACAAG ACCAAAACAA AACAGCAACA ACAAAGCGGC AGGGAAGAAG TTGACACCCT    8160
```

| | | |
|---|---|---|
| TGGGGATACT TTAGTCAACA CACTTAGAAC AGATTGTGCC AGGCCTGTTG GATTCCTGGA | 8220 |
| GTTGATGGGA TCGTGGGAAG GCACAATGGG GAGCAAGTGG GCTTGGGTTA TGGCTCAGTG | 8280 |
| GGTAAAGTGC AATTATGGGG ATCTGAGTTT GAATCCCTGG TACCCATATA AAGACACAGA | 8340 |
| TGCGGTGATG GGCACTTGTG ACAATGAGAT CATCAATAGG GAATGGAGAC AGGAGGGACC | 8400 |
| TCTGGGGTTC ACTGGCCAGG CAGTCTAGCT GAATCAAAGA GCTCCAAGTT CAGTCGATAG | 8460 |
| CTCCTGAAGA TGACAACTGA GGCTATTCTC CAAACCCCAC ACGCAGGGAC ACATGCGTAA | 8520 |
| TAAATAAAAT TTTAAAAATA TTAAATAATA GTGTTTGAGA GGCACTTTAT ATGTTCTAAT | 8580 |
| CATTTGTGCT TTTGTTTATT TGTTCAGGTT TGTTTGTTTG TTTGTTGGAA GACAGGGGTC | 8640 |
| TCAAGTAGCC CAGGCTAGCT TTGAACTATA TATTTCATAT ATTTTGAGGC AGTCTTATGC | 8700 |
| CTTTTATCTA GGTTTTCTTG GCATCTAAAG CTATAGCTGT GTGTTACTCC AATGGAACAT | 8760 |
| CTGGGCAGTT ACCCAGCACC TTCAAATGCA GAGCCCACAC CTGATAGGGT CGGGCTCGCC | 8820 |
| CTGCTCAGGG GTCGCTGCTA GTCCAAGCCA GTCCAAGCGG ACTTCCCGCG TCCTGTCCTT | 8880 |
| GCAACCCTGG TGGGAGGTGG AAAAGCCCCC AAATACCCAG TCTCACCCTC CATCGGAGTT | 8940 |
| TCCTTTATGC TTATCACGGC CTGTTTCCGT GTCTTTGATG AGACCAAGGT GTGGGACAG | 9000 |
| TATATTTATA AAAAGCCACC AGCAGTTTCC GCTGTAAGGA AAAAAAAATC ACTCTAGA | 9058 |

(2) INFORMATION FOR SEQ ID NO: 10:

(i) SEQUENCE CHARACTERISTICS:
        (A) LENGTH: 717
        (B) TYPE: Nucleic acid
        (C) STRANDEDNESS: Double
        (D) TOPOLOGY: Linear (ii) MOLECULE TYPE: cDNA (xi) SEQUENCE DESCRIPTION: SEQ ID NO: 10:

| | | |
|---|---|---|
| ATGGAGAGTG TGGTACAGCC TTCAGTGTTT GTGGTGGATG GACAGACAGA CATCCCATTC | 60 |
| AGGCGGCTGG GACAGAACCA CAGGAGACGG CACTGCGGCA CTGTCCAGGT CAGCCTGGCC | 120 |
| CTGCTGCTGC TGCTGGGTGC TGGGCTGGCC ACTGAGGGCT GGTTTCTCCT GAGACTGCAT | 180 |
| CAGCGTCTTG GGGACATAGT AGCTCATCTG CCAGATGGAG GCAAAGGCTC CTGGGAGAAG | 240 |
| CTGATACAAG ATCAACGATC TCACCAGCCC AACCCAGCAG CACATCTCAC AGGAGCTAAC | 300 |
| GCCAGCTTGA TAGGCATTGG TGGACCTCTG TTATGGGAGA CACAACTTGG CCTGGCCTTC | 360 |
| CTGAGGGGCC TGACGTATCA TGATGGGCC CTGGTGACCA CCGAGGCTGG CTACTACTAC | 420 |
| GTGTACTCCA AAGTGCAGTT GAGTGGTGTG GGCTGCCCCC AGGGGCTGGC CAATGGCCTC | 480 |
| CCCATCACCC ACGGGCTGTA CAAGCGCACA TCCCGATACC CCAAGGAGTT AGAACTGCTG | 540 |
| GTCAGCCGGC GGTCACCTTG TGGCCGGGCC AACAGCTCCC GAGTCTGGTG GGACAGTAGT | 600 |
| TTCCTCGGCG GAGTGGTACA TCTGGAGGCC GGAGAAGAGG TGGTGGTCCG CGTGCCTGGA | 660 |
| AACCGCCTGG TCAGACCACG TGATGGCACG AGGTCCTATT TCGGAGCTTT CATGATC | 717 |

(2) INFORMATION FOR SEQ ID NO: 11:

(i) SEQUENCE CHARACTERISTICS:
        (A) LENGTH: 24
        (B) TYPE: Nucleic acid
        (C) STRANDEDNESS: Single
        (D) TOPOLOGY: Linear (ii) MOLECULE TYPE: Synthetic DNA (xi) SEQUENCE DESCRIPTION: SEQ ID NO: 11:

AGGTCAACCC AGCAGCGCAT CTCA          24

(2) INFORMATION FOR SEQ ID NO: 12:

(i) SEQUENCE CHARACTERISTICS:
        (A) LENGTH: 28
        (B) TYPE: Nucleic acid
        (C) STRANDEDNESS: Single
        (D) TOPOLOGY: Linear (ii) MOLECULE TYPE: Synthetic DNA (xi) SEQUENCE DESCRIPTION: SEQ ID NO: 12:

AGGTCAACCC AGCAGCGCAT CTCACAGG          28

(2) INFORMATION FOR SEQ ID NO: 13:

(i) SEQUENCE CHARACTERISTICS:
        (A) LENGTH: 30
        (B) TYPE: Nucleic acid
        (C) STRANDEDNESS: Single
        (D) TOPOLOGY: Linear (ii) MOLECULE TYPE: Synthetic DNA (xi) SEQUENCE DESCRIPTION: SEQ ID NO: 13:

CAAATTAAAC CGGGTACCAT CACGCAGTCG          30

(2) INFORMATION FOR SEQ ID NO: 14:

(i) SEQUENCE CHARACTERISTICS:
        (A) LENGTH: 25
        (B) TYPE: Nucleic acid
        (C) STRANDEDNESS: Single
        (D) TOPOLOGY: Linear (ii) MOLECULE TYPE: Synthetic DNA (xi) SEQUENCE DESCRIPTION: SEQ ID NO: 14:

TCTGCTCTGG CATGGAGAGT GTGGT          25

(2) INFORMATION FOR SEQ ID NO: 15:

(i) SEQUENCE CHARACTERISTICS:
        (A) LENGTH: 24
        (B) TYPE: Nucleic acid
        (C) STRANDEDNESS: Single
        (D) TOPOLOGY: Linear (ii) MOLECULE TYPE: Synthetic DNA (xi) SEQUENCE DESCRIPTION: SEQ ID NO: 15:

CTATTGCTGG GTTTGAGGTG AGTC          24

(2) INFORMATION FOR SEQ ID NO: 16:

(i) SEQUENCE CHARACTERISTICS:
        (A) LENGTH: 22
        (B) TYPE: Nucleic acid
        (C) STRANDEDNESS: Single
        (D) TOPOLOGY: Linear (ii) MOLECULE TYPE: Synthetic DNA (xi) SEQUENCE DESCRIPTION: SEQ ID NO: 16:

GTAATACGAC TCACTATAGG GC          22

```
(2) INFORMATION FOR SEQ ID NO: 17:

(i) SEQUENCE CHARACTERISTICS:
        (A) LENGTH: 19
        (B) TYPE: Nucleic acid
        (C) STRANDEDNESS: Single
        (D) TOPOLOGY: Linear (ii) MOLECULE TYPE: Synthetic DNA (xi) SEQUENCE DESCRIPTION: SEQ ID NO: 17:

ACTATAGGGC ACGCGTGGT                                               19

(2) INFORMATION FOR SEQ ID NO: 18:

(i) SEQUENCE CHARACTERISTICS:
        (A) LENGTH: 48
        (B) TYPE: Nucleic acid
        (C) STRANDEDNESS: Single
        (D) TOPOLOGY: Linear (ii) MOLECULE TYPE: Synthetic DNA (xi) SEQUENCE DESCRIPTION: SEQ ID NO: 18:

GTAATACGAC TCACTATAGG GCACGCGTGG TCGACGGCCC GGGCTGGT               48

(2) INFORMATION FOR SEQ ID NO: 19:

(i) SEQUENCE CHARACTERISTICS:
        (A) LENGTH: 27
        (B) TYPE: Nucleic acid
        (C) STRANDEDNESS: Single
        (D) TOPOLOGY: Linear (ii) MOLECULE TYPE: Synthetic DNA (xi) SEQUENCE DESCRIPTION: SEQ ID NO: 19:

CAGCCCAGCA CCTAGCAGCA GCACCAG                                      27

(2) INFORMATION FOR SEQ ID NO: 20:

(i) SEQUENCE CHARACTERISTICS:
        (A) LENGTH: 27
        (B) TYPE: Nucleic acid
        (C) STRANDEDNESS: Single
        (D) TOPOLOGY: Linear (ii) MOLECULE TYPE: Synthetic DNA (xi) SEQUENCE DESCRIPTION: SEQ ID NO: 20:

GCCGCCTGAA TGGGATGTCC GTCTGTC                                      27

(2) INFORMATION FOR SEQ ID NO: 21:

(i) SEQUENCE CHARACTERISTICS:
        (A) LENGTH: 32
        (B) TYPE: Nucleic acid
        (C) STRANDEDNESS: Single
        (D) TOPOLOGY: Linear (ii) MOLECULE TYPE: Synthetic DNA (xi) SEQUENCE DESCRIPTION: SEQ ID NO: 21:

ACGAATTCCA AGAGCGAAGG TCTCACGAGG TC                                32

(2) INFORMATION FOR SEQ ID NO: 22:

(i) SEQUENCE CHARACTERISTICS:
        (A) LENGTH: 35
```

(B) TYPE: Nucleic acid
    (C) STRANDEDNESS: Single
    (D) TOPOLOGY: Linear (ii) MOLECULE TYPE: Synthetic DNA (xi) SEQUENCE DESCRIPTION: SEQ ID NO: 22:

AGTCTAGACT CCTTCCTTCA CACCATGAAA GCCCC                                35

(2) INFORMATION FOR SEQ ID NO: 23:

(i) SEQUENCE CHARACTERISTICS:
       (A) LENGTH: 24
       (B) TYPE: Nucleic acid
       (C) STRANDEDNESS: Single
       (D) TOPOLOGY: Linear (ii) MOLECULE TYPE: Synthetic DNA (xi) SEQUENCE DESCRIPTION: SEQ ID NO: 23:

CCTGACCCTG GGCTTCTGAG CCTC                                            24

(2) INFORMATION FOR SEQ ID NO: 24:

(i) SEQUENCE CHARACTERISTICS:
       (A) LENGTH: 27
       (B) TYPE: Nucleic acid
       (C) STRANDEDNESS: Single
       (D) TOPOLOGY: Linear (ii) MOLECULE TYPE: Synthetic DNA (xi) SEQUENCE DESCRIPTION: SEQ ID NO: 24:

TCCACAAAAT CCATTGTCGT CATAGCC                                         27

(2) INFORMATION FOR SEQ ID NO: 25:

(i) SEQUENCE CHARACTERISTICS:
       (A) LENGTH: 242
       (B) TYPE: Amino acid
       (D) TOPOLOGY: Linear (ii) MOLECULE TYPE: Protein (xi) SEQUENCE DESCRIPTION: SEQ ID NO: 25:

Met Glu Xaa Ser Val Val Xaa Pro Ser Val Phe Val Val Asp Gly Gln
 1               5                  10                  15

Thr Asp Ile Pro Phe Xaa Arg Leu Xaa Xaa Xaa His Arg Arg Xaa Xaa
                20                  25                  30

Cys Xaa Xaa Xaa Xaa Val Xaa Leu Xaa Leu Xaa Leu Leu Leu Xaa Gly
            35                  40                  45

Ala Gly Leu Ala Xaa Gln Gly Trp Phe Leu Leu Xaa Leu His Xaa Arg
        50                  55                  60

Leu Gly Xaa Xaa Val Xaa Xaa Leu Pro Asp Gly Xaa Xaa Gly Ser Trp
 65                  70                  75                  80

Glu Xaa Leu Ile Gln Xaa Xaa Arg Ser His Xaa Xaa Asn Pro Ala Ala
                85                  90                  95

His Leu Thr Gly Ala Asn Xaa Ser Leu Xaa Gly Xaa Gly Pro Leu
                100                 105                 110

Leu Trp Glu Thr Xaa Leu Gly Leu Ala Phe Leu Arg Gly Leu Xaa Tyr
            115                 120                 125

His Asp Gly Ala Leu Val Xaa Xaa Xaa Xaa Gly Tyr Tyr Tyr Xaa Tyr
        130                 135                 140

-continued

```
Ser Lys Val Gln Leu Xaa Gly Val Gly Cys Pro Xaa Gly Leu Ala Xaa
145                 150                 155                 160

Xaa Xaa Xaa Ile Thr His Gly Leu Tyr Lys Arg Thr Xaa Arg Tyr Pro
            165                 170                 175

Glu Xaa Leu Glu Leu Leu Val Ser Xaa Xaa Ser Pro Cys Gly Arg Ala
        180                 185                 190

Xaa Xaa Ser Ser Arg Val Trp Trp Asp Ser Ser Phe Leu Gly Gly Val
        195                 200                 205

Val His Leu Glu Ala Gly Glu Xaa Val Val Val Arg Val Xaa Xaa Xaa
        210                 215                 220

Arg Leu Val Arg Xaa Arg Asp Gly Thr Arg Ser Tyr Phe Gly Ala Phe
225                 230                 235                 240

Met Val
```

FAS LIGAND-LIKE PROTEIN, ITS PRODUCTION AND USE

This application is a divisional of 08/913,014, filed Sep. 4, 1997, now U.S. Pat. No. 6,235,878.

TECHNICAL FIELD

The present invention relates to a novel fas ligand-like protein having an apotosis-inducing activity, etc. and a DNA coding for the protein.

BACKGROUND ART

A multicellular organism maintains its homeostasis ingeniously by controlling the proliferation and death of its cells. In the course of ontogenesis, many cells are eliminated through apotosis, and even in a mature organism the cells constituting its tissues maintain their functional integrity balancing proliferation against death. Cell death in this context is generally termed "programmed cell death", which is known to occur through the process of apoptosis which is morphologically distinguished from that of necrosis, the accidental cell death caused by physical and chemical factors. Apoptotic cell death is characterized by blebbing of the cell membrane, chromatin condensation and DNA fragmentation, with the affected cells being eventually removed by phagocytic cells such as macrophages for reutilization (International Review of Cytology, 68, 251–306, 1980).

Many physiological and pathological events related to apotosis have been identified until now and many attempts made to diagnose, prevent, or treat various diseases through induction or inhibition of the process of apoptosis (Science, 267, 1456–1462, 1995). Apotosis is one of the vital phenomena which are attracting more than usual attention in the pharmaceutical industries.

While apotosis is induced in a variety of physiological stimuli, Fas antigen (CD95, APO-1), in particular, is gathering a considerable attention of scientists as a molecule triggering death of immune cells (Science, 267, 1449–1456, 1995). Fas antigen is a 45 kDa type I membrane protein belonging to the TNF (tumor necrosis factor) receptor family and induces cell death by coupling itself to Fas ligand. Whereas Fas antigen is expressed in various blood cells and in many tissues and cells of the liver, heart, and small intestine, expression of Fas ligand, which is a type II membrane protein with a molecular mass of 40 kDa, is confined to activated T lymphocytes, natural killer (NK) cells, macrophages, and certain tissues such as the testis and cornea. Recently, genetic analyses in mice have revealed that the Fas antigen gene has found to be the lpr (lymphoproliferation) structural gene which is mutated in mice with autoimmune disease, i.e. lpr mice, and that, in gld (generalized-lymphoproliferative disease) mice presenting with symptoms similar to those of lpr mice, a mutations of Fas ligand is present. In humans, too, mutations of the Fas antigen gene have been reported in some patients with autoimmune disease, suggesting strongly that disfunction of the Fas/Fas ligand system induces autoimmune diseases (Science, 268, 1347–1349, 1995).

Moreover, it has been found that the human Fas ligand could be cleaved by matrix metalloproteinase and released as the soluble Fas ligand, suggesting that the Fas ligand not only regulates cell-to-cell interactions due to mutual contact but more broadly modulates immune responses (Journal of Experimental Medicine, 182, 1777–1783, 1995).

Among proteins of the TNF family which have various biological activities, TNF-α, lymphotoxin-α (LT-α) and lymphotoxin-β (LT-β), have apotosis-inducing activity as well as Fas ligand (The New England Journal of Medicine, 334, 1717–1725, 1996). TNF-α was first discovered in 1975 as a factor having tumor necrosis-inducing activity but today more importance is attached to TNF-α as an immunopotentiating factor mediating inflammatory reactions and as a defensive factor against various invasions such as viral and bacterial infections. LT-α was initially reported as a cytotoxic factor produced by lymphocytes. Like TNF-α, LT-α forms a homotrimer, binds to the two TNF receptors of 55 kDa and 75 kDa, and although differing in the potency of activity, shows a biological profile similar to that of TNF except for the stimulatory activity of B cell proliferation. LT-β is a 33 kDa membrane-binding protein having high homology with LT-α; it forms a heterotrimer with LT-α, binds the newly identified LT-β receptor which is different from said two TNF receptors, and has a biological function, i.e. formation of lymph nodes, which is not found in said TNF and LT-α. More recently, a protein molecule (Apo-2L/TRAIL) having an apotosis-inducing activity and showing high homology with the Fas ligand has been identified for the first time and shown to bind another receptor, termed DR4, different from TNF receptors and Fas antigen to exhibit cytotoxicity (The Journal of Biological Chemistry, 271, 12687–12690, 1996; Science, 276, 111–113, 1997). Therefore, it is supposed that such TNF and TNF receptor family proteins varying in the ligand and receptor expression specificity may have a physiologically different apotosis-inducing function each other.

Recently, it has been reported the relationship of apotosis with diseases (Japanese Journal of Clinical Medicine, 54, No. 7, Jul. 1, 1996). According to this literature, the disease caused by an insufficient apotosis process includes cancer (e.g. mammary cancer, prostatic cancer, ovarian cancer, follicular lymphocytoma, cancer associated with p53 mutation), viral infection (e.g. herpes virus infection, adenovirus infection, poxvirus infection), autoimmune disease (e.g. systemic lupus erythematosus, immune complex glomerulonephritis), etc. On the other hand, the disease caused by an increased apotosis process includes AIDS (acquired immunodeficiency syndrome), neurodegenerative disease (e.g. Alzheimer's disease, Parkinson's disease, amyotrophic lateral sclerosis, pigmentary retinitis, cerebellar degeneration), diseases due to osteomyelodysplasia (e.g. aplastic anemia), ischemic disease (e.g. myocardial infarction, stroke), toxic liver disease (e.g. alcoholism), etc.

The present invention has for its object to provide a novel Fas ligand-like protein or a partial peptide thereof, or a salt thereof; a DNA coding for the protein; a recombinant gene vector; a transformant which is transformed with said vector; a method of producing the protein; a medicinal composition comprising the protein or DNA; an antibody to the protein, a method of screening for a receptor agonist/antagonist and a kit for the screening; a receptor agonist/antagonist as obtained by the screening and a pharmaceutical composition thereof; a method of screening a compound which promotes or inhibits proteinase having an activity to convert the protein and a kit for the screening; a compound as obtained by the screening and a pharmaceutical composition thereof; a method of screening for a compound which enhances or inhibits a intracellular signal transduction and a kit for the screening; a compound as obtained by the screening and a pharmaceutical composition thereof, and so on.

Isolation of a novel Fas ligand-like protein would cast light on a hitherto-hidden pathway of TNF family/TNF receptor family-mediated apotosis and, should it be expressed with organ- or cell-specificity, would permit a more sophisticated exploration of the relationship of diseases, by organ, with apotosis and lead to development of a novel drug having either an antagonistic action or an agonistic action on the new Fas ligand-like protein and consequently contributing to the prevention and treatment of diseases.

The inventors of the present invention succeeded, after much research, in cloning a cDNA having a novel nucleotide sequence from each of the human liver-, murine embryo- and rat liver-derived cDNA libraries. The inventors further found that the protein encoded by the cloned cDNAs are useful Fas ligand-like proteins. The present invention has been completed on the basis of the above finding and subsequent research.

DISCLOSURE OF INVENTION

The present invention, provides:

(1) A protein comprising an amino acid sequence represented by SEQ ID NO:1, SEQ ID NO:2 or SEQ ID NO:3 or a substantial equivalent thereto, or a salt thereof;

(2) The protein according to (1) wherein the amino acid sequence substantially equivalent to the amino acid sequence represented by SEQ ID NO:1, SEQ ID NO:2 or SEQ ID NO:3 contains amino acid sequences of the 8th–21st residues, 55th–59th residues, 93rd–102th residues, 109th–116th residues, 118th–126th residues, 128th–134th residues, 144th–149th residues, 162nd–170th residues, 176th–182nd residues, 184th–189th residues, 193rd–213rd residues, 215th–219th residues and 228th–239th residues of the amino acid sequence represented by SEQ ID NO:1;

(3) The protein according to (1) wherein the amino acid sequence substantially equivalent to the amino acid sequence represented by SEQ ID NO:1 or SEQ ID NO:2 contains amino acid sequences of the 8th–21st residues, 54th–59th residues, 93rd–102th residues, 109th–116th residues, 118th–126th residues, 128th–134th residues, 144th–149th residues, 162nd–170th residues, 176th–182nd residues, 184th–189th residues, 193rd–213rd residues, 215th–219th residues and 228th–240th residues of the amino acid sequence represented by SEQ ID NO:1;

(4) The protein according to any one of (1) to (2) which is a protein having an apotosis-inducing activity;

(5) A partial peptide of the protein according to (1) or a salt thereof;

(6) A isolated DNA comprising a DNA having a nucleotide sequence coding for the protein according to (1);

(7). The DNA according to (6) which has a nucleotide sequence represented by any one of SEQ ID NO:4 to SEQ ID NO:10;

(8) A recombinant vector comprising the DNA according to (6);

(9) A transformant which is transformed with the recombinant vector according to (8);

(10) A method for producing the protein or salt according to (1) which comprises culturing the transformant according to (9) under conditions suitable to express and secrete and accumulate the protein according to (1) and collecting the same;

(11) A pharmaceutical composition comprising the protein according to (1), the partial peptide according to (5) or a salt thereof;

(12) The pharmaceutical composition according to (11), which is a therapeutic or prophylactic agent for cancer, viral infection, *Helicobacter pylori* infection, invasive staphylococcia, hepatitis, nephritis, bone disease, atherosclerosis or pain;

(13) A pharmaceutical composition comprising the DNA according to (6);

(14) The pharmaceutical composition according to (13) which is a therapeutic prophylactic agent for cancer, viral infection, *Helicobacter pylori* infection, invasive staphylococcia, hepatitis, nephritis, bone disease, atherosclerosis or pain;

(15) An antibody against the protein according to (1) or the partial peptide according to (5) or a salt thereof;

(16) A method for screening for a compound, or a salt thereof, capable of changing a binding activity of the protein according to (1), the partial peptide according to (5) or a salt thereof with a receptor to which the protein according to (1) can bind, which comprises measuring and comparing an amount of binding of the protein according to (1), the partial peptide according to (5) or a salt thereof with the receptor, in cases that (i) the protein according to (1), the partial peptide according to (5) or a salt thereof is contacted with the receptor or a partial peptide thereof and (ii) the protein according to (1), the partial peptide according to (5) or a salt thereof and a test compound are contacted with the receptor or a partial peptide thereof;

(17) A method for screening for a compound, or a salt thereof, capable of changing a binding activity of the protein according to (1), the partial peptide according to (5) or a salt thereof with a receptor to which the protein according to (1) can bind, which comprises measuring and comparing an amount of binding of the protein according to (1), the partial peptide according to (5) or a salt thereof with a cell containing the receptor or a cell membrane fraction thereof, in cases that (i) the protein according to (1), the partial peptide according to (5) or a salt thereof is contacted with the cell or the cell membrane fraction and (ii) the protein according to (1), the partial peptide according to (5) or a salt thereof and a test compound are contacted with the cell or the cell membrane fraction;

(18) A method for screening for a compound, or a salt thereof, capable of changing a binding activity of the protein according to (1), the partial peptide according to (5) or a salt thereof with a receptor to which the protein according to (1) can bind, which comprises measuring and comparing an apotosis-inducing activity or cytotoxic activity in the cells containing the receptor, in cases that (i) a cell containing the protein according to (1) is contacted with a cell containing the receptor and (ii) a cell containing the protein according to (1) and a test compound are contacted with a cell containing the receptor;

(19) A kit for screening for a compound, or a salt thereof, capable of changing a binding activity of the protein according to (1), the partial peptide according to (5) or a salt thereof with a receptor to which the protein according to (1) can bind, which comprises the protein according to (1), the partial peptide according to (5) or a salt thereof;

(20) A compound capable of changing a binding activity of the protein according to (1), the partial peptide according to (5) or a salt thereof with a receptor to which the protein according to (1) can bind, or a salt thereof, which is obtained by using the screening method according to any one of (16) to (18) or the screening kit according to (19);

(21) A pharmaceutical composition which comprises a receptor agonist to a receptor to which the protein according to (1) can bind, which is obtained by using the screening method according to any one of (16) to (18) or the screening kit according to (19);

(22) The pharmaceutical composition according to (21), which is a therapeutic or prophylactic for cancer, viral infection, *Helicobacter pylori* infection, invasive staphylococcia, hepatitis, nephritis, bone disease, atherosclerosis or pain;

(23) A pharmaceutical composition which comprises a receptor antagonist to a receptor to which the protein according to (1) can bind, which is obtained by using the screening method according to any one of (16) to (18) or the screening kit according to (19);

(24) The pharmaceutical composition according to (23), which is a therapeutic or prophylactic agent for acquired immunodeficiency syndrome, inflammation, neurodegenerative disease due to osteomyelodysplasia, ischemic disease, destruction of joint tissues in rheumatism, hepatitis, autoimmune disease, cardiomyopathy, diabetes, diabetic complications, influenza, glomerulonephritis or uncerative colitis;

(25) A method for screening for a compound which promotes or inhibits an activity of a proteinase having an activity to convert the protein according to (1), or a salt thereof, which comprises measuring and comparing
    (a) a receptor-mediated cell stimulating activity or
    (b) an apotosis-inducing activity or cytotoxic activity in a cell containing a receptor to which the protein according to (1) can bind, in cases that (i) a cell containing the protein according to (1) is contacted with a culture supernatant obtained by culture of a cell containing the protein according to (1) in presence of the proteinase (where the cell containing the protein according to (1) produces and secretes an extracellular proteinase having an activity to convert the protein according to (1), it may be the extracellular proteinase which the cell produces and secretes) and (ii) a cell containing the protein according to (1) is contacted with a culture supernatant obtained by culture of a cell containing the protein according to (1) in presence of the proteinase (where the cell containing the protein according to (1) produces and secretes an extracellular proteinase having an activity to convert the protein according to (1), it may be the extracellular proteinase which the cell produces and secretes) and a test compound;

(26) A kit for screening for a compound which promotes or inhibits an activity of a proteinase having an activity to convert the protein according to (1), or a salt thereof, which comprises the protein according to (1), the partial peptide according to (5) or a salt thereof;

(27) A compound which promotes or inhibits an activity of a proteinase having an activity to convert the protein according to (1) or a salt thereof, which is obtained by using the screening method according to (25) or the screening kit according to (26);

(28) A pharmaceutical composition which comprises a compound which promotes an activity of a proteinase having an activity to convert the protein according to (1) or a salt thereof, which is obtained by using the screening method according to (25) or the screening kit according to (26);

(29) The pharmaceutical composition according to (28) which is a therapeutic or prophylactic agent for cancer, viral infection, *Helicobacter pylori* infection, invasive staphylococcia, hepatitis, nephritis, bone disease, atherosclerosis or pain.

(30) A pharmaceutical composition which comprises a compound which inhibits an activity of a proteinase having an activity to convert the protein according to (1) or a salt thereof, which is obtained by using the screening method according to (25) or the screening kit according to (26);

(31) The pharmaceutical composition according to (30) which is a therapeutic or prophylactic agent for destruction of acquired immunodeficiency syndrome, joint tissues in rheumatism, inflammation, hepatitis or autoimmune disease;

(32) A method for screening for a compound, or a salt thereof, which enhances or inhibits a intracellular signal transduction following the binding of the protein according to (1), the partial peptide according to (5) or a salt thereof with a receptor to which the protein according to (1) can bind, which comprises measuring and comparing a intracellular signal transduction following the binding of the protein according to (1), the partial peptide according to (5) or a salt thereof with the receptor, in cases that (i) the protein according to (1), the partial peptide according to (5) or a salt thereof is contacted with a cell containing the receptor and (ii) the protein according to (1), the partial peptide according to (5) or a salt thereof and a test compound are contacted with a cell containing the receptor;

(33) A method for screening for a compound, or a salt thereof, which enhances or inhibits a intracellular signal transduction following the binding of the protein according to (1), the partial peptide according to (5) or a salt thereof with a receptor to which the protein according to (1) can bind, which comprises measuring and comparing a intracellular signal transduction following the binding of the protein according to (1), the partial peptide according to (5) or a salt thereof with the receptor, in cases that (i) a cell containing the protein according to (1), the partial peptide according to (5) or a salt thereof is contacted with a cell containing the receptor and (ii) a cell containing the protein according to (1), the partial peptide according to (5) or a salt thereof and a test compound are contacted with a cell containing the receptor;

(34) A kit for screening for a compound, or a salt thereof, which enhances or inhibits a intracellular signal transduction following the binding of the protein according to (1), the partial peptide according to (5) or a salt thereof with a receptor to which the protein according to (1) can bind, which comprises the protein according to (1), the partial peptide according to (5) or a salt thereof;

(35) A compound, or a salt thereof, which enhances or inhibits a intracellular signal transduction following the binding of the protein according to (1), the partial peptide according to (5) or a salt thereof with a receptor to which the protein according to (1) can bind, which is obtained by using the screening method according to (32) or (33) or the screening kit according to (34);

(36) A pharmaceutical composition which comprises a compound, or a salt thereof, which enhances a intracellular signal transduction following the binding of the protein according to (1), the partial peptide according to (5) or a salt thereof with a receptor to which the protein according to (1) can bind, which is obtained by using the screening method according to any one of (32) or (33) or the screening kit according to (34);

(37) The pharmaceutical composition according to (36) which is a therapeutic or prophylactic agent for cancer, viral infection, *Helicobacter pylori* infection, invasive staphylococcia, hepatitis, nephritis, bone disease, atherosclerosis or pain;

(38) A pharmaceutical composition which comprises a compound, or a salt thereof, which inhibits a intracellular signal transduction following the binding of the protein according to (1), the partial peptide according to (5) or a salt thereof with a receptor to which the protein according to (1) can bind, which is obtained by using the screening method according to any one of (32) or (33) or the screening kit according to (34);

(39) The pharmaceutical composition according to (38) which is a therapeutic or prophylactic composition for acquired immunodeficiency syndrome, inflammation, neurodegenerative disease due to osteomyelodysplasia, ischemic disease, destruction of joint tissues in rheumatism, hepatitis, autoimmune disease, cardiomyopathy, diabetes, diabetic complications, influenza, glomerulonephritis or uncerative colitis;

(40) A method for treating or preventing cancer, viral infection, *Helicobacter pylori* infection, invasive staphylococcia, hepatitis, nephritis, bone disease, atherosclerosis or pain in human or a mammal, which comprises administering an effective amount of the protein according to (1), the partial peptide according to (5) or a salt thereof to human or the mammal;

(41) A method for treating or preventing cancer, viral infection, *Helicobacter pylori* infection, invasive staphylococcia, hepatitis, nephritis, bone disease, atherosclerosis or pain in human or a mammal, which comprises administering an effective amount of the the DNA according to (6);

(42) Use of the protein according to (1), the partial peptide according to (5) or a salt thereof for manufacture of a therapeutic or prophylactic agent for cancer, viral infection, *Helicobacter pylori* infection, invasive staphylococcia, hepatitis, nephritis, bone disease, atherosclerosis or pain;

(43) Use of the DNA according to (6) for manufacture of a therapeutic or prophylactic agent for cancer, viral infection, *Helicobacter pylori* infection, invasive staphylococcia, hepatitis, nephritis, bone disease, atherosclerosis or pain;

(44) A non-human mammal, harboring a foreign DNA according to (6) or a foreign mutant DNA thereof;

(45) The non-human mammal according to (44), which is a rodent;

(46) The non-human mammal according to (45), wherein the rodent is mouse;

(47) The non-human mammal according to (44), the DNA is a DNA having a nucleotide sequence represented by SEQ ID NO:9;

(48) A recombinant vector containing the foreign DNA according to (6) or a foreign mutant DNA thereof and capable of being expressed in a mammal;

(49) The non-human mammal according to (48), the DNA is a DNA having a nucleotide sequence represented by SEQ ID NO:9;

(50) A non-human mammalian embryonic stem cell wherein the DNA according to (6) is inactivated;

(51) The non-human mammalian embryonic stem cell according to (50), wherein the DNA is inactivated by introduction of a reporter gene;

(52) The non-human mammalian embryonic stem cell according to (50), which is neomycin-resistant;

(53) The non-human mammalian embryonic stem cell according to (50), wherein the non-human mammalian is a rodent;

(54) The non-human mammalian embryonic stem cell according to (53), wherein the rodent is mouse;

(55) The non-human mammalian embryonic stem cell according to (54), wherein the DNA is a DNA having a nucleotide sequence represented by SEQ ID NO:9;

(56) A non-human mammal deficient in expression of the DNA according to (6), wherein the DNA is inactivated;

(57) The non-human mammal according to (56), wherein the DNA is inactivated by introducion of a reporter gene and the reporter gene can be expressed under the control of the promoter against the DNA according to (6);

(58) The non-human mammal according to (56), which is a rodent;

(59) The non-human mammal according to (58), wherein the rodent is mouse;

(60) The non-human mammal according to (59), wherein the DNA is a DNA having a nucleotide sequence represented by SEQ ID NO:9;

(61) A method for screening for a compound which enhances or inhibits an activity of promoter against the DNA according to (6), or a salt thereof, which comprises administering a test compound to the non-human mammal according to (57) and detecting an expression of the reporter gene;

(62) A compound which enhances an activity of promoter against the DNA according to (6), or a salt thereof, which is obtained by using the screening method according to (61);

(63) A pharmaceutical composition which comprises a compound which enhances an activity of promoter against the DNA according to (6), or a salt thereof which is obtained by using the screening method according to (61);

(64) The pharmaceutical composition according to (63) which is a therapeutic or prophylactic agent for cancer, viral infection, *Helicobacter pylori* infection, invasive staphylococcia, hepatitis, nephritis, bone disease, atherosclerosis or pain;

(65) A compound which inhibits an activity of promoter against the DNA according to (6) or a salt thereof, which is obtained by using the screening method according to (61);

(66) A pharmaceutical composition which comprises a compound which inhibits an activity of promoter against the DNA according to (6), or a salt thereof which is obtained by using the screening method according to (58); and

(67) The pharmaceutical composition according to (66) which is a therapeutic or prophylactic agent for acquired immunodeficiency syndrome, inflammation, neurodegenerative disease due to osteomyelodysplasia, ischemic disease, destruction of joint tissues in rheumatism, hepatitis, autoimmune disease, cardiomyopathy, diabetes, diabetic complications, influenza, glomerulonephritis or uncerative colitis.

Moreover, the present invention provides: (68) The protein according to (1), which comprises an amino acid sequence represented by the formula:

```
Met Glu Xaa Ser Val Val Xaa Pro Ser Val Phe Val Val Asp
 1           5                   10
Gly Gln Thr Asp Ile Pro Phe Xaa Arg Leu Xaa Xaa Xaa His
 15                  20                  25
Arg Arg Xaa Xaa Cys Xaa Xaa Xaa Xaa Val Xaa Leu Xaa Leu
     30              35                  40
Xaa Leu Leu Leu Xaa Gly Ala Gly Leu Ala Xaa Gln Gly Trp
         45              50                  55
Phe Leu Leu Xaa Leu His Xaa Arg Leu Gly Xaa Xaa Vla Xaa
             60              65                      70
Xaa Leu Pro Asp Gly Xaa Xaa Gly Ser Trp Glu Xaa Leu Ile
                 75              80
Gln Xaa Xaa Arg Ser His Xaa Xaa Asn Pro Ala Ala His Leu
 85                  90              95
Thr Gly Ala Asn Xaa Ser Leu Xaa Gly Xaa Gly Gly Pro Leu
     100             105             110
Leu Trp Glu Thr Xaa Leu Gly Leu Ala Phe Leu Arg Gly Leu
         115             120                 125
Xaa Tyr His Asp gly Ala Leu Val Xaa Xaa Xaa Xaa Gly Tyr
             130             135                 140
Tyr Tyr Xaa Tyr Ser Lys Val Gln Leu Xaa Gly Val Gly Cys
                 145             150
Pro Xaa Gly Leu Ala Xaa Xaa Xaa Xaa Ile Thr His Gly Leu
155                 160                 165
Tyr Lys Arg Thr Xaa Arg Tyr Pro Glu Xaa Leu Glu Leu Leu
    170                 175                 180
Val Ser Xaa Xaa Ser Pro Cys Gly Arg Ala Xaa Xaa Ser Ser
         185                 190                 195
Arg Val Trp Trp Asp Ser Ser Phe Leu Gly Gly Val Val His
             200                 205                 210
Leu Glu Ala Gly Glu Xaa Val Val Val Arg Val Xaa Xaa Xaa
                 215                 220
Arg Leu Val Arg Xaa Arg Asp Gly Thr Arg Ser Tyr Phe Gly
225                 230                 235
Ala Phe Met Val (I),
240
``` wherein Xaa represents an amino acid residues, and Xaa may be deleted.);

(69) The partial peptide according to (5), which comprises at least one amino acid sequence selected from the group consisting of amino acid sequences of the 8th–21st residues, 55th–59th residues, 93rd–102th residues, 109th–116th residues, 118th–126th residues, 128th–134th residues, 144th–149th residues, 162nd–170th residues, 176th–182nd residues, 184th–189th residues, 193rd–213rd residues, 215th–219th residues and 228th–239th residues of the amino acid sequence represented by SEQ ID NO:1;

(70) The partial peptide according to (5), which comprises at least one amino acid sequence selected from the group consisting of amino acid sequences of the 8th–21st residues, 54th–59th residues, 93rd–102th residues, 109th–116th residues, 118th–126th residues, 128th–134th residues, 144th–149th residues, 162nd–170th residues, 176th–182nd residues, 184th–189th residues, 193rd–213rd residues, 215th–219th residues and 228th–240th residues of the amino acid sequence represented by SEQ ID NO:1;

(71) The partial peptide according to (5), which comprises an amino acid sequence of the 83rd–240th residues of the amino acid sequence represented by SEQ ID NO:1 or the 81st–239th residues of the amino acid sequence represented by SEQ ID NO:2;

(72) An isolated DNA comprising a DNA having a nucleotide sequence which hybridizes under high stringent condition to a nucleotide sequence represented by any one of SEQ ID NO:4 to SEQ ID NO:10;

(73) A recombinant vector comprising the DNA according to (72);

(74) A transformant which is transformed with the recombinant vector according to (69);

(75) A process for producing a protein which is encoded by the DNA according to (72) or a salt thereof, which comprises culturing the transformant according to (74) under conditions suitable to express and accumulate the protein according to (1) and collect the same;

(76) A protein encoded by the DNA according to (75) which is produced by the process according to (71) or a salt thereof;

(77) The screening method according to any one of (16) to (18), wherein the receptor to which the protein according to (1) can bind is a receptor belonging to the TNF receptor family (e.g. TNF receptors, lymphotoxin-β receptor, Fas, CD27, CD30, CD40, OX40, DR4, DR3/WSL-1 or TR2) or a receptor against the protein according to (1);

(78) A screening kit according to (19), wherein the receptor to which the protein according to (1) can bind is a receptor, belonging to the TNF receptor family (e.g. TNF receptors, lymphotoxin-β receptor, Fas, CD27, CD30, CD40, OX40, DR4, DR3/WSL-1 or TR2) or a receptor against the protein according to (1).

(79) A method of quantitative determination of the protein according to (1), the partial peptide according to (5) or a salt thereof in a test liquid sample, which comprises
(a) competitively reacting the test liquid sample and a labeled protein according to (1) or partial peptide according to (5) with the antibody according to (15), and
(b) measuring the ratio of the labeled protein according to (1) or partial peptide according to (5) which binds to the antibody;

(80) A method of quantitative determination of the protein according to (1), the partial peptide according to (5) or a salt thereof in a test liquid sample, which comprises
(a) reacting the test liquid sample with the antibody according to (15) immobilized on an insoluble carrier and another antibody which is labeled according to (15) simultaneously or continuously, and
(b) measuring the activity of the labeling agent on the insoluble carrier.

(81) A pharmaceutical composition which comprises the antibody according to (15) (preferably, the antibody according to (15) which inhibits an activity of the protein according to (1));

(82) The pharmaceutical composition according to (81), which is a therapeutic or prophylactic agent for acquired immunodeficiency syndrome, inflammation, neurodegenerative disease due to osteomyelodysplasia, ischemic disease, destruction of joint tissues in rheumatism, hepatitis, autoimmune disease, cardiomyopathy, diabetes, diabetic complications, influenza, glomerulonephritis or uncerative colitis;

(83) An antisense DNA having a nucleotide sequence complementary or substantially complementary to the DNA according to (6) or (72), and capable of suppressing expression of the same DNA;

(84) The antisense DNA according to (83), wherein the nucleotide sequence substantially complementary to the DNA according to (6) or (72) is a nucleotide sequence having an identity of not less than about 40% (preferably not less than about 60%, more preferably not less than about 80%, further preferably not less than about 90%, for still better results, not less than about 95%) to the total nucleotide sequence or partial nucleotide sequence of the nucleotide sequence complementary to the DNA according to (6) or (72);

(85) A pharmaceutical composition which comprises the antisense DNA according to (83); and

(86) The pharmaceutical composition according to (85) which is a therapeutic or prophylactic agent for acquired immunodeficiency syndrome, inflammation neurodegenerative disease due to osteomyelodysplasia, ischemic disease, destruction of joint tissues in rheumatism, hepatitis, autoimmune disease, cardiomyopathy, diabetes, diabetic complications, influenza, glomerulonephritis or uncerative colitis.

The protein of the present invention has an amino acid sequence represented by SEQ ID NO:1, SEQ ID NO:2 or SEQ ID NO:3, or a substantial equivalent thereto.

The protein of the present invention may be a protein derived from cells of any kind (e.g. splenocytes, neurons, glia cells, pancreatic β cells, myelocytes, mesangial cells, Langerhan's cells, epidermal cells, epithelial cells, endothelial cells, fibroblasts, fibrous cells, muscle cells, fat cells, immune cells (e.g. macrophages, T cells, B cells, natural killer cells, mast cells, neutrophils, basophils, eosinophils, monocytes), megakaryocytes synovial cells, chondrocytes, osteocytes, osteoblasts, osteoclasts, mammary cells, hepatocytes, interstitial cells, progenitor cells of said cells, stem cells, cancer cells, etc.) of human or other warm-blooded animals (e.g. guinea pig, rat, mouse, chicken, rabbit, swine, sheep, bovine, equine, monkey, etc.) and all tissues in which such cells are present, such as brain, various parts of brain (e.g. olfactory bulb, amygdaloid nucleus, cerebral basal nucleus, hippocampus, thalamus, hypothalamus, cerebral cortex, medulla oblongata, cerebellum), spinal cord, pituitary gland, stomach, spleen, kidney, liver, gonad, thyroid, gall-bladder, bone marrow, adrenal gland, skin, muscle, lung, gastrointestinal tract (e.g. large intestine, small intestine, duodenum), blood vessels, heart, thymus, spleen, submandibular gland, peripheral blood, prostate, testis, ovary, placenta, uterus, bone, joint, skeletal muscle, etc. It may be a synthetic protein as well.

Examples of the amino acid sequence which is substantially equivalent to the amino acid sequence represented by SEQ ID NO:1, SEQ ID NO:2 or SEQ ID NO:3 are an amino acid sequence which is not less than about 40%, preferably not less than about 60%, more preferably not less than about 80%, still more preferably not less than about 90%, and most preferably not less than about 95% identity to the amino acid sequence represented by SEQ ID NO:1, SEQ ID NO:2 or SEQ ID NO:3, and so on. Particularly preferable examples are an amino acid sequences having a identity of not less than about 40%, preferably not less than about 60%, more preferably not less than about 80%, and still more preferably not less than about 90% to the amino acid sequence of the 83rd–240th residues of the amino acid sequence represented by SEQ ID NO:1, the 81st–239th residues of the amino acid sequence represented by SEQ ID NO:2 or the 81st–239th residues of the amino acid sequence represented by SEQ ID NO:3.

And, as an amino acid sequence substantially equivalent to the amino acid sequence represented by SEQ ID NO:1, SEQ ID NO:2 or SEQ ID NO:3, an amino acid sequence containing the amino acid sequence of the 8th–21st residues, 55th–59th residues, 93rd–102nd residues, 109th–116th residues, 118th–126th residues, 128th–134th residues, 144th–149th residues, 162nd–170th residues, 176th–182nd residues, 184th–189th residues, 193rd–213rd residues, 215th–219th residues and 228th–239th residues, respectively, of the amino acid sequence represented by SEQ ID NO:1, and so on are also preferred. These amino acid sequences are common amino acid sequences between the amino acid sequence represented by SEQ ID NO:1, the amino acid sequence represented by SEQ ID NO:2 and the amino acid sequence represented by SEQ ID NO:3.

And, as an amino acid sequence substantially equivalent to the amino acid sequence represented by SEQ ID NO:1 or SEQ ID NO:2, an amino acid sequence containing the amino acid sequence of the 8th–21st residues, 54th–59th residues, 93rd–102nd residues, 109th–116th residues, 118th–126th residues, 128th–134th residues, 144th–149th residues, 162nd–170th residues, 176th–182nd residues, 184th–189th residues, 193rd–213rd residues, 215th–219th residues and 228th–240th residues, respectively, of the amino acid sequence represented by SEQ ID NO:1, and so on are also preferred.

The above amino acid sequences correspond to the 6th–20th residues, 52nd–57th residues, 91st–100th residues, 107th–114th residues, 116th–124th residues, 126th–132nd residues, 142nd–147th residues, 162nd–170th residues, 176th–182nd residues, 184th–189th residues, 192nd–212nd residues, 214th–218th residues and 227th–239th residues, respectively, of the amino acid sequence represented by SEQ ID NO:2, and are common amino acid sequences between the amino acid sequence represented by SEQ ID NO:1 and the amino acid sequence represented by SEQ ID NO:2.

Examples of the protein of the present invention which comprises an amino acid sequence substantially equivalent to the amino acid sequence represented by SEQ ID NO:1, SEQ ID NO:2 or SEQ ID NO:3 are a protein having an amino acid sequence substantially equivalent to the amino acid sequence represented by SEQ ID NO:1, SEQ ID NO:2 or SEQ ID NO:3 and having a qualitatively equivalent activity to the protein having the amino acid sequence represented by SEQ ID NO:1, SEQ ID NO:2 or SEQ ID NO:3.

The term "qualitatively equivalent activity" is used herein to mean substantial equivalence in qualitative terms such as an apotosis-inducing activity, a cytotoxic activity against virus-infected cells, etc. Therefore, the degree of equivalence may range, for example, from about 0.01 to about 20 times (preferably about 0.2 to 5, more preferably 0.5 to 2 times). However, differences in quantitative terms such as the potency of activity and the molecular mass of protein are immaterial.

Activities such as an apotosis-inducing activity, a cytotoxic activity against virus-infected cells and so on may be measured by a per se known method or its analogue method. For example, the activities may be measured by the method for screening as mentioned below.

And, the protein of the present invention includes the socalled muteins, for example, proteins comprising (1) an amino acid sequence wherein one or more amino acid residues (for example 1 to 80, preferably 1 to 20, more preferably about 1 to 9, and still more preferably a few (1 to 5) amino acid residues) are deleted from the amino acid sequence represented by SEQ ID NO:1, SEQ ID NO:2 or SEQ ID NO:3, (2) an amino acid sequence wherein one or more amino acid residues (for example, 1 to 80, preferably about 1 to 20, more preferably about 1 to 9, and still more preferably a few (1 to 5) amino acid residues) are added to the amino acid sequence represented by SEQ ID NO:1, SEQ ID NO:2 or SEQ ID NO:3, (3) an amino acid sequence wherein one or more other amino acid residues in the amino acid sequence represented by SEQ ID NO:1, SEQ ID NO:2 or SEQ ID NO:3 are substituted with 1 or more amino acid residues (for example 1 to 80, preferably about 1 to 20, more preferably about 1 to 9, and still more preferably a few (1 to 5) amino acid residues), or (4) combinations thereof.

In the above-mentioned deletion, substitution, or addition, examples of the positions of deletion, substitution or addition are not so critical but are preferably positions other than (1) the 8th–21st residues, 55th–59th residues (or 54th–59th residues), 93rd–102nd residues, 109th–126th residues, 118th–126th residues, 128th–134th residues, 144th–149th residues, 162nd–170th residues, 176th–182nd residues, 184th–189th residues, 193rd–213rd residues, 215th–219th residues, or 228th–239th residues (or 228th–240th residues) of the amino acid sequence represented by SEQ ID NO:1, preferably positions other than the 93rd–102nd residues, 109th–116th residues, 118th–126th residues, 128th–134th residues, 144th–149th residues, 162nd–170th residues, 176th–182nd residues, 184th–189th residues, 193rd–213rd residues, 215th–219th residues or 228th–240th residues of the amino acid sequence represented by SEQ ID NO:1, (2) positions other than the 6th–19th residues, 52nd–57th residues, 91st–100th residues, 107th–114th residues, 116th–124th residues, 126th–132nd residues, 142nd–147th residues, 162nd–170th residues, 176th–182nd residues, 184th–189th residues, 192nd–212nd residues, 214th–218th residues or 227th–238th residues (or 227th–239th residues) of the amino acid sequence represented by SEQ ID NO:2, preferably positions other than the 91st–100th residues, 107th–114th residues, 116th–124th residues, 126th–132nd residues, 142nd–147th residues, 162nd–170th residues, 176th–182nd residues, 184th–189th residues, 192nd–212nd residues, 214th–218th residues or 227th–239th residues represented by SEQ ID NO:2, or (3) positions other than the 6th–19th residues, 52nd–57th residues, 91st–100th residues, 107th–114th residues, 116th–124th residues, 126th–132nd residues, 142nd–147th residues, 162nd–170th residues, 176th–182nd residues, 184th–189th residues, 192nd–212nd residues, 214th–218th residues or 227th–238th residues (or 227th–239th residues) of the amino acid sequence represented by SEQ ID NO:3, preferably positions other than the 91st–100th residues, 107th–114th residues, 116th–124th residues, 126th–132nd residues, 142nd-147th residues, 162nd–170th residues, 176th–182nd residues, 184th–189th residues, 192nd–212nd residues, 214th–218th residues or 227th–239th residues represented by SEQ ID NO:3.

More specifically, proteins having the amino acid sequence (SEQ ID NO:25) represented by the following formula:

| Met 1 | Glu | Xaa | Ser | Val 5 | Val | Xaa | Pro | Ser | Val 10 | Phe | Val | Val | Asp |
|---|---|---|---|---|---|---|---|---|---|---|---|---|---|
| Gly 15 | Gln | Thr | Asp | Ile | Pro 20 | Phe | Xaa | Arg | Leu | Xaa 25 | Xaa | Xaa | His |
| Arg | Arg 30 | Xaa | Xaa | Cys | Xaa | Xaa 35 | Xaa | Xaa | Val | Xaa | Leu 40 | Xaa | Leu |
| Xaa | Leu | Leu 45 | Leu | Xaa | Gly | Ala | Gly 50 | Leu | Ala | Xaa | Gln | Gly 55 | Trp |

-continued

```
Phe Leu Leu Xaa Leu His Xaa Arg Leu Gly Xaa Xaa Vla Xaa
             60              65                    70

Xaa Leu Pro Asp Gly Xaa Xaa Gly Ser Trp Glu Xaa Leu Ile
             75              80

Gln Xaa Xaa Arg Ser His Xaa Xaa Asn Pro Ala Ala His Leu
 85              90              95

Thr Gly Ala Asn Xaa Ser Leu Xaa Gly Xaa Gly Pro Leu
    100             105         110

Leu Trp Glu Thr Xaa Leu Gly Leu Ala Phe Leu Arg Gly Leu
        115             120             125

Xaa Tyr His Asp gly Ala Leu Val Xaa Xaa Xaa Xaa Gly Tyr
            130             135                     140

Tyr Tyr Xaa Tyr Ser Lys Val Gln Leu Xaa Gly Val Gly Cys
            145                     150

Pro Xaa Gly Leu Ala Xaa Xaa Xaa Xaa Ile Thr His Gly Leu
155             160                 165

Tyr Lys Arg Thr Xaa Arg Tyr Pro Glu Xaa Leu Glu Leu Leu
    170             175             180

Val Ser Xaa Xaa Ser Pro Cys Gly Arg Ala Xaa Xaa Ser Ser
        185             190                 195

Arg Val Trp Trp Asp Ser Ser Phe Leu Gly Gly Val Val His
            200             205                     210

Leu Glu Ala Gly Glu Xaa Val Val Val Arg Val Xaa Xaa Xaa
            215                 220

Arg Leu Val Arg Xaa Arg Asp Gly Thr Arg Ser Tyr Phe Gly
225             230             235

Ala Phe Met Val (I)
240
```

(Xaa represents an optional amino acid residue and Xaa may be deleted) are also preferably used.

Referring to the above formula (I), Xaa may be missing in one or more positions (for example 1 to 56, preferably 1 to 40, more preferably 1 to 20, still more preferably 1 to 9, and most preferably a few (1 to 5) positions).

The amino acid residue represented by Xaa may be any one of a hydrophilic amino acid residue and a hydrophobic amino acid residue, and may also be any one of an acidic amino acid residue, a basic amino acid residue, or a neutral amino acid residue. Specifical examples of Xaa are Gly, Ala, Val, Leu, Ile, Ser, Thr, Cys, Met, Glu, Asp, Lys, Arg, His, Phe, Tyr, Trp, Pro, Asn, Gln and so on.

The 3rd Xaa in the formula (I) is preferably Glu or missing.

The 7th Xaa is preferably a hydrophilic amino acid residue, typically Arg or Gln.

The 22nd Xaa is preferably a hydrophilic amino acid residue, typically Thr or Arg.

The 25th Xaa is preferably a hydrophilic residue, typically Gly or Glu.

The 26th Xaa is preferably a hydrophilic residue, typically Arg or Gln.

The 27th Xaa is preferably a hydrophilic residue, typically Ser or Asn.

The 31st Xaa is preferably a hydrophilic residue, typically Gln or Arg.

The 32nd Xaa is preferably a hydrophilic residue, typically Ser or Arg.

The 34th Xaa is preferably a hydrophilic residue, typically Ser or Gly.

The 35th Xaa is preferably Val or Thr, for instance.

The 36th Xaa is preferably a hydrophobic residue, typically Ala or Val.

The 37th Xaa is preferably a hydrophilic residue, typically Arg or Gln.

The 39th Xaa is preferably a hydrophilic residue, typically Gly or Ser.

The 41st Xaa is preferably Gly or Ala, for instance.

The 43rd Xaa is preferably a hydrophobic residue, typically Leu or Val.

The 47th Xaa is preferably Met or missing.

The 53rd Xaa is preferably Val or Thr, for instance.

The 60th Xaa is preferably a hydrophilic residue, typically Gln or Arg.

The 63rd Xaa is preferably Trp or Gln, for instance.

The 67th Xaa is preferably an acidic amino acid residue, typically Glu or Asp.

The 68th Xaa is preferably a hydrophobic residue, typically Met or Ile.

The 70th Xaa is preferably Thr or Ala, for instance.

The 71st Xaa is preferably a basic amino acid residue, typically Arg or His.

The 76th Xaa is preferably Pro or Gly, for instance.

The 77th Xaa is preferably Ala or Lys, for instance.

The 82nd Xaa is preferably a hydrophilic residue, typically Gln or Lys.

The 86th Xaa is preferably a acidic amino acid residue, typically Glu or Asp.

The 87th Xaa is preferably a hydrophilic residue, typically Arg or Gln.

The 91st Xaa is preferably a hydrophilic residue, typically Glu or Gln.

The 92nd Xaa is preferably a hydrophobic residue, typically Val or Ala.

The 103rd Xaa is preferably Ser or Ala, for instance.

The 106th Xaa is preferably Thr or Ile, for instance.

The 108th Xaa is preferably Ser or Ile, for instance.

The 117th Xaa is preferably a hydrophilic residue, typically Gln or Arg.

The 127th Xaa is preferably a hydrophilic residue, typically Ser or Thr.

The 135th Xaa is preferably Val or Thr, for instance.

The 136th Xaa is preferably Thr or Met, for instance.

The 137th Xaa is preferably a hydrophilic residue, typically Lys or Glu.

The 138th Xaa is preferably a hydrophobic residue, typically Ala or Pro.

The 143rd Xaa is preferably a hydrophobic residue, typically Ile or Val.

The 150th Xaa is preferably a hydrophilic residue, typically Gly or Ser.

The 156th Xaa is preferably Leu or Gln, for instance.

The 160th Xaa is preferably a hydrophilic residue, typically Ser or Asn.

The 161st Xaa is preferably a hydrophilic residue, typically Thr or Gly.

The 162nd Xaa is preferably Leu or missing.

The 163rd Xaa is preferably Pro or missing.

The 173rd Xaa is preferably Pro or Ser, for instance.

The 178th Xaa is preferably a hydrophilic residue, typically Glu or Lys.

The 185th or 186th Xaa is preferably a hydrophilic residue, typically Gln or Arg.

The 193rd Xaa is preferably Thr or missing.

The 194th Xaa is preferably a hydrophilic residue, typically Ser or Asn.

The 216th Xaa is preferably a hydrophilic residue, typically Lys or Glu.

The 222nd Xaa is preferably a hydrophobic residue, typically Leu or Pro.

The 223rd Xaa is preferably a hydrophilic residue, typically Asp or Gly.

The 224th Xaa is preferably a hydrophilic residue, typically Glu or Asn.

The 229th Xaa is preferably a hydrophobic residue, typically Leu or Pro.

Throughout this specification, proteins are represented in accordance with the conventions for description of peptides, that is the N-terminus (amino terminus) at left and the C-terminus (carboxyl terminus) at right. The protein of the present invention including the protein containing the amino acid sequence of SEQ ID NO:1 is usually in the carboxyl (—COOH) or carboxylate (—COO$^-$) form at the C-terminus but may be in the amide (—CONH$_2$) or ester (—COOR) form.

R in the ester residue includes a $C_{1-6}$ alkyl group (e.g. methyl, ethyl, n-propyl, isopropyl, n-butyl, etc., a $C_{3-8}$ cycloalkyl group (e.g. cyclopentyl, cyclohexyl, etc.), a $C_{6-12}$ aryl group (e.g. phenyl, α-naphthyl, etc.), a $C_{7-14}$ aralkyl group such as a phenyl-$C_{1-2}$ alkyl group (e.g. benzyl, phenethyl, etc.) and α-naphthyl-$C_{1-2}$ alkyl, (e.g. α-naphthylmethyl, etc.), as well as pivaloyloxymethyl group which is often used for the production of esters for oral administration.

When the protein of the present invention has a carboxyl (or carboxylate) function in any position other than the C-terminus, the corresponding carboxamide or ester form is also included in the scope of the present invention. The ester mentioned just above may be any of the esters mentioned for the C-terminal carboxyl function.

Furthermore, the protein of the present invention includes (1) the protein in which the N-terminal amino acid residue has been protected with a protective group (e.g. $C_{1-6}$ acyl group wuch as $C_{1-6}$ alkanoyl such as formyl, acetyl, etc.), (2) the protein in which the N-terminal side of Glu has been cleaved in vivo to form pyroglutamic acid, (3) the protein in which the side chain of any relevant constituent amino acid (e.g. OH, SH, NH$_2$, imidazole group, indole group, guanizino group, etc.) has been protected by any protective group (e.g. $C_{1-6}$ acyl group such as $C_{1-6}$ alkanoyl such as formyl or acetyl, etc.), and (4) the complex protein such as glycoproteins obtained by attachment of sugar chains.

More preferable examples of the protein of the present invention are a human liver-derived protein having the amino acid sequence represented by SEQ ID NO:1 (FIG. 1 or 2), a murine embryo-derived protein having the amino acid sequence represented by SEQ ID NO:2 (FIG. 3 or 4), a rat liver-derived protein having the amino acid sequence represented by SEQ ID NO:3 (FIG. 6), and so on.

The partial peptide of the protein of the present invention may be any peptide having a qualitatively equivalent activity to the above-mentioned protein of the present invention such as an apotosis-inducing activity, a cytotoxic activity against virus-infected cells and so on. For example, the partial peptides include peptides comprising at least not less than about 20, preferably not less than about 50, more, preferably not less than about 70, for still better result, not less than about 100, best result, not less than 200 amino acid residues of the amino acid sequence of the proteins of the present invention.

Examples of the partial peptide are (i) a peptide having at least one or more amino acid sequences selected from the amino acid sequences corresponding to the 8th–21st residues, 55th–59th residues, 93rd–102nd residues, 109th–116th residues, 118th–126th residues, 128th–134th residues, 144th–149th residues, 162nd–170th residues, 176th–182nd residues, 184th–189th residues, 193rd–213rd residues, 215th–219th residues and 228th–239th residues of the amino acid sequence represented by SEQ ID NO:1 (that is, the 6th–20th residues, 52nd–57th residues, 91st–100th residues, 107th–114th residues, 116th–124th residues, 126th–132nd residues, 142nd–147th residues, 162nd–170th residues, 176th–182nd residues, 184th–189th residues, 192nd–212nd residues, 214th–218th residues and 227th–238th residues of the amino acid sequence represented by SEQ ID NO:2 or SEQ ID NO:3), (ii) a peptide having at least one or more amino acid sequences selected from the amino acid sequences corresponding to the 8th–2lst residues, 54th–59th residues, 93rd–102nd residues, 109th–116th residues, 118th–126th residues, 128th–134th residues, 144th–149th residues, 162nd–170th residues, 176th–182nd residues, 184th–189th residues, 193rd–213rd residues, 215th–219th residues and 228th–240th residues of the amino acid sequence represented by SEQ ID NO:1 (that is, the 6th–20th residues, 52nd–57th residues, 91st–100th residues, 107th–114th residues, 116th–124th residues, 126th–132nd residues, 142nd–147th residues, 162nd–170th residues, 176th–182nd residues, 184th–189th residues, 192nd–212nd residues, 214th–218th residues and 227th–239th residues of the amino acid sequence represented by SEQ ID NO:2 or SEQ ID NO:3), More specifically, a partial peptide having an amino acid sequence corresponding to the 83rd–240th residues of the amino acid sequence represented by SEQ ID NO:1 or a partial peptide having an amino acid sequence corresponding to the 81st–239th residues of the amino acid sequence of SEQ ID NO:2, etc. are preferred.

Furthermore, examples of the partial peptide of. the present invention are (1) a peptide which comprises a substantially equivalent amino acid sequence to the 83rd to 240th amino acid sequence of the amino acid sequence represented by SEQ ID NO:1 and has a substantially equivalent activity to the protein comprising the amino acid sequence represented by SEQ ID NO:1, (2) a peptide which comprises a substantially equivalent amino acid sequence to the 81st to 239th amino acid sequence of the amino acid sequence represented by SEQ ID NO:2 and has a substantially equivalent activity to the peptide comprising the 81lst to 239th amino acid sequence of the amino acid sequence represented by SEQ ID NO:2, (3) a peptide which comprises a substantially equivalent amino acid sequence to the 81st to 239th amino acid sequence of the amino acid sequence represented by SEQ ID NO:3 and has a substantially equivalent activity to the peptide comprising the 81st to 239th amino acid sequence of the amino acid sequence represented by SEQ ID NO:3.

Examples of the substantially equivalent amino acid sequence to the 83rd to 240th amino acid sequence of the amino acid sequence represented by SEQ ID NO:1 are an amino acid sequence of not less than about 40%, preferably not less than about 60%, more preferably not less than about 80%, further more preferably not less than about 90%, for still better result, not less than about 95% identity to the 83rd to 240th amino acid sequence of the amino acid sequence represented by SEQ ID NO:1.

Examples of the substantially equivalent amino acid sequence to the 81st to 239th amino acid sequence of the amino acid sequence represented by SEQ ID NO:2 are an amino acid sequence of not less than about 40%, preferably not less than about 60%, more preferably not less than about 80%, further more preferably not less than about 90%, for still better result, not less than about 95% identity to the 81st to 239th amino acid sequence of the amino acid sequence represented by SEQ ID NO:2.

Examples of the substantially equivalent amino acid sequence to the 81st to 239th amino acid sequence of the amino acid sequence represented by SEQ ID NO:3 are an amino acid sequence of not less than about 40%, preferably not less than about 60%, more preferably not less than about 80%, further more preferably not less than about 90%, for still better result, not less than about 95% identity to the 81st to 239th amino acid sequence of the amino acid sequence represented by SEQ ID NO:3.

The term "substantially equivalent activity" has the same meaning as defined above. The "substantially equivalent activity" can be measured by the same method as mentioned above.

The partial peptide of the present invention may include any peptides comprising (1) an amino acid sequence wherein 1 or more amino acid residues (for example 1 to 80, preferably 1 to 20, more preferably 1 to 9, further more preferably 1 to 9, further more preferably a few (1 to 5) amino acid residues) are deleted from the 83rd to 240th amino acid sequence of the amino acid sequence represented by SEQ ID NO:1, (2) an amino acid sequence wherein 1 or more amino acid residues (for example 1 to 80, preferable 1 to 20, more preferably 1 to 9, further more preferably a few (1 to 5) amino acid residues) are added to the 83rd to 240th amino acid sequence of the amino acid sequence represented by SEQ ID NO:1, (3) an amino acid sequence wherein 1 or more amino acid residues (for example 1 to 80, preferably 1 to 20, more preferably a few (1 to 5) amino acid residues) in the 83rd to 240th amino acid sequence of the amino acid sequence represented by SEQ ID NO:1 are substituted with 1 or more amino acid residues (for example 1 to 80, preferably 1 to 20, more preferably 1 to 9, further more preferably a few (1 to 5) amino acid residues), or (4) combinations thereof.

Other partial peptide of the present invention may include any peptides comprising (1) an amino acid sequence wherein 1 or more amino acid residues (for example 1 to 80, preferably 1 to 20, more preferably a few (1 to 5) amino acid residues) are deleted from the 81st to 239th amino acid sequence of the amino acid sequence represented by SEQ ID NO:2, (2) an amino acid sequence wherein 1 or more amino acid residues (for example 1 to 80, preferable 1 to 20, more preferable 1 to 9, further more preferably a few (1 to 5) amino acid residues) are added to the 81st to 239th amino acid sequence of the amino acid sequence represented by SEQ ID NO:2, (3) an amino acid sequence wherein 1 or more amino acid residues (for example 1 to 80, preferably 1 to 20, more preferably 1 to 9, further more preferably a few (1 to 5) amino acid residues) in the 81st to 239th amino acid sequence of the amino acid sequence represented by SEQ ID NO:2 are substituted with 1 or. more amino acid residues (for example 1 to 80, preferably 1 to 20, more preferably 1 to 9, further more preferably a few (1 to 5) amino acid residues), or (4) combinations thereof.

Other partial peptide of the present invention may include any peptides comprising (1) an amino acid sequence wherein 1 or more amino acid residues (for example 1 to 80, preferably 1 to 20, more preferably a few (1 to 5) amino acid residues) are deleted from the 81st to 239th amino acid sequence of the amino acid sequence represented by SEQ ID NO:3, (2) an amino acid sequence wherein 1 or more amino acid residues (for example 1 to 80, preferable 1 to 20, more preferable 1 to 9, further more preferably a few (1 to 5) amino acid residues) are added to the 81st to 239th amino acid sequence of the amino acid sequence represented by SEQ ID NO:3, (3) an amino acid sequence wherein 1 or more amino acid residues (for example 1 to 80, preferably 1 to 20, more preferably 1 to 9, further more preferably a few (1 to 5) amino acid residues) in the 81st to 239th amino acid sequence of the amino acid sequence represented by SEQ ID NO:3 are substituted with 1 or more amino acid residues (for example 1 to 80, preferably 1 to 20, more preferably 1 to 9, further more preferably a few (1 to 5) amino acid residues), or (4) combinations thereof.

In the above-mentioned deletion, substitution or addition, specifically, a peptide having an amino acid sequence wherein the 1st to 82nd amino acid residues are deleted from the amino acid sequence represented by the above formula (I), etc. are preferably used.

The peptide of the present invention is usually in the carboxyl (—COOH) or carboxylate (—COO⁻ form at the C-terminus, but may instead be in the amide (—CONH$_2$) or ester (—COOR) form as same as the protein of the present invention as mentioned above.

Furthermore, the partial peptide of the present invention includes (1) the peptide in which the N-terminal amino acid residue has been protected with a protective group, (2) the peptide in which the N-terminal side of Glu has been cleaved in vivo to form pyroglutamic acid, (3) the peptide in which the side chain or any relevant constituent amino acid has been protected by any protective group, and (4) the complex peptide such as glycoproteins obtained by attachment of sugar chains as same as the protein of the present invention as mentioned above.

The specific examples of the partial peptide of the present invention are a peptide comprising the 83rd to 240th amino acid sequence of the amino acid sequence represented by SEQ ID NO:1, a peptide comprising the 81st to 239th amino acid sequence of the amino acid sequence represented by SEQ ID NO:2, a peptide comprising the 81st to 239th amino acid sequence of the amino acid sequence represented by SEQ ID NO:3, and so on.

The salts of the protein or the partial peptide of the present invention includes salts with physiologically acceptable bases (e.g. alkali metals) or acids such as organic or inorganic acids, and is preferably a physiologically acceptable acid addition salt. Examples of such salts are salts thereof with inorganic acids (e.g. hydrochloric acid, phosphoric acid, hydrobromic acid or sulfuric acid, etc.) and salts thereof with organic acids (e.g. acetic acid, formic acid, propionic acid, fumaric acid, maleic acid, succinic acid, tartaric acid, citric acid, malic acid, oxalic acid, benzoic acid, methanesulfonic acid or benzenesulfonic acid, etc.)

The protein or a salt thereof of the present invention can be produced from the tissues or cells of human or other warm-blooded animals by per se known. purification technologies or, as described hereinafter, by culturing a transformant carrying a DNA encoding the protein. It can also be produced in accordance with the procedures for peptide synthesis which are described hereinafter.

When the protein of the present invention is produced from the tissues or cells of human or other warm-blooded animals, the tissues or cells of human or other warm-blood animals are homogenized and the protein of the present invention is extracted by an acid, etc. The protein can be isolated and purified from the extracted solution by a combination of chromatography such as reverse phase chromatography, ion exchange chromatography and so on.

For the synthesis of the protein of the present invention, a partial peptide thereof or their salts, or their amide form, any of commercial resins available for protein synthesis can be employed. Among such resins are chloromethyl resin, hydroxymethyl resin, benzhydrylamino resin, aminomethyl resin, 4-benzyloxybenzyl alcohol resin, 4-methylbenzhydrylamino resin, PAM resin, 4-hydroxymethyl-methylphenylacetamidomethyl resin, polyacrylamide resin, 4-(2',4'-dimethoxyphenyl-hydroxymethyl)phenoxy resin, and 4-(2',4'-dimethoxyphenyl-Fmoc-aminoethyl)phenoxy resin. Using such a resin, amino acids which may be beforehand protected at side-chain functional groups in a suitable manner can be serially condensed with the α-amino group in the order corresponding to the amino acid sequence of the objective protein by various condensation techniques which are per se known. After completion of the final condensation reaction, the protein is separated from the resin and the protective groups are removed. Then, in highly diluted solution, the intramolecular disulfide-forming reaction is carried out to provide the objective proteins or amides thereof.

Referring to the above condensation of protected amino acids, various activating agents known to be useful for protein synthesis can be utilized, and carbodiimide reagents are especially preferred. The carbodiimide reagents include are DCC, N,N'-diisopropylcarbodiimide, and N-ethyl-N'-(3-dimethylaminoprolyl)carbodiimide and so on. For activation by these reagents, the protected amino acid and a racemization inhibitor (e.g. HOBt, HOOBt, etc.) can be directly added to the resin, or the protected amino acid can be activated beforehand in the form of symmetric acid anhydride, HOBt ester or HOOBt ester and, then, added to the resin.

The solvent used for the above-mentioned activation of protected amino acids or the conjugation thereof to the resin can be properly selected from among the solvents known to be useful for protein condensation reactions. Examples of the solvent are acid amides (e.g. N,N-dimethylformamide, N,N-dimethylacetamide, N-methylpyrrolidone, etc.), halogenated hydrocarbons (e.g. methylene chloride, chloroform, etc.), alcohols (e.g. trifluoroethanol, sulfoxides (e.g. dimethyl sulfoxide, etc.), ethers (e.g. pyridine, dioxane, tetrahydrofuran, etc.), nitriles (e.g. acetonitrile, propionitrile, etc.), esters (e.g. methyl acetate, ethyl acetate, etc.), and suitable mixtures of these solvents. The reaction temperature can be selected from the range known to be useful for protein-forming reactions, usually the range of about −20° C. to about 50° C. The activated amino acid derivative is generally used in a 1.5 to 4-fold excess. When the condensation is found insufficient by ninhydrin assay, the reaction can be repeated to make the condensation throughly sufficient. When sufficient condensation can not be achieved by repeated reaction, an unreacted amino acid can be acetylated by using acetic anhydride or acetylimidazole so as not to effect a subsequent reaction.

The protective groups for protecting the amino group of the starting compound include Z, Boc, t-pentyloxycarbonyl, isobornyloxycarbonyl, 4-methoxy-benzyloxycarbonyl, Cl-Z, Br-Z, adamantyloxycarbonyl, trifluoroacetyl, phthaloyl, formyl, 2-nitrophenylsulfenyl, diphenylphosphinothioyl, Fmoc, and so on.

The carboxyl group can be protected in the form of, for example, an alkyl ester (e.g. straight-chain, branched, or cyclic alkyl esters such as methyl, ethyl, propyl, butyl, t-butyl, cyclopentyl, cyclohexyl, cycloheptyl, cyclooctyl, 2-adamantyl, and so on), an aralkyl ester (e.g. benzyl, 4-nitrobenzyl, 4-methoxybenzyl, 4-chlorobenzyl, benzhydryl, and so on), phenacyl ester, benzyloxycarbonylhydrazide, t-butoxycarbonylhydrazide or tritylhydrazide.

The hydroxyl group of serine can be protected in the form of an ester or an ether. The group suitable for esterification includes carboxylic acid-derived acyl groups such as a lower($C_{1-6}$) alkanoyl group (e.g. acetyl, etc.), an aroyl group (e.g. benzoyl, etc.), a benzyloxycarbonyl, an ethoxycarbonyl group and so on. The group suitable for etherification includes a benzyl group, a tetrahydropyranyl group, a t-butyl group and so on.

The protective group used for protecting the phenolic hydroxyl group of tyrosine includes Bzl, $C_{1-2}$-Bzl, 2-nitrobenzyl, Br-Z, t-butyl and so on.

The protective group for the imidazole group of histidine includes Tos, 4-methoxy-2,3,6-trimethylbenzenesulfonyl, DNP, benzyloxymethyl, Bum, Boc, Trt, Fmoc and so on.

The starting compound with activated carboxyl groups includes the corresponding acid anhydride, azide, and active ester (e.g. esters with alcohols such as pentachlorophenol, 2,4,5-trichlorophenol, 2,4-dinitrophenol, cyanomethyl alcohol, p-nitrophenol, HONB, N-hydroxysuccinimide, N-hydroxyphthalimide, HOBt, etc.). The starting compound with activated amino groups includes the corresponding phosphorylamide.

The method for removal of such protective groups includes catalytic reduction in a hydrogen stream in the presence of a catalyst (e.g. Pd black or Pd-on-carbon), acid treatment with anhydrous hydrogen fluoride, methanesulfonic acid, trifluoromethanesulfonic acid, trifluoroacetic acid or a mixture thereof, treatment with a base such as diisopropylethylamine, triethylamine, piperidine, piperazine or the like, and reduction with sodium metal in liquid ammonia. The above deprotection by treatment with acid is generally conducted at a temperature of about −20° C. to 40° C. This acid treatment can be carried out advantageously in the presence of a cation acceptor such as anisole, phenol, thioanisole, m-cresol, p-cresol, dimethyl sulfide, 1,4-butanedithiol, 1,2-ethanedithiol, or the like. The 2,4-dinitrophenyl group used for protecting the imidazole group of histidine can be removed by treatment with thiophenol, and the formyl group used for protecting the indole group of tryptophan can be removed not only by said acid treatment in the presence of 1,2-ethanedithiol, 1,4-butanedithiol or the like as described hereinbefore, but also by alkali treatment with diluted sodium hydroxide solution, diluted liquid ammonia, or the like.

The method for protecting any functional group that should not take part in the contemplated reaction, the protective group to be used for such protection, the method for eliminating the protective group, and the method for activating the functional group to be involved in the contemplated reaction can all be properly selected from among the known methods and groups.

An alternative method for providing the protein in amide form typically comprises protecting the α-carboxyl group of the C-terminal amino acid in the form of an amide, extending the peptide (protein) chain to a desired length towards the N-terminus, deprotecting the N-terminal α-amino acid of the resulting peptide chain selectively to provide an N-terminal-deprotected fragment, preparing a peptide (protein) fragment with its C-terminal carboxyl group selectively deprotected, and condensing the two fragments in a solvent such as the mixed solvent as mentioned above. The condensation reaction can be carried out in the same manner as described hereinbefore. After purification of the protected protein thus obtained by condensation, all the protective groups are eliminated by the procedures described hereinbefore to provide the contemplated protein in a crude form. This crude protein is purified by suitable known purification techniques and lyophilized to provide the desired protein amide.

A method for providing the protein in an ester form comprises condensing the α-carboxyl group of the C-terminal amino acid with a suitable alcohol to prepare the corresponding ester and subjecting this ester to the same procedure as described for purification of the protein amide to provide the objective protein ester.

The partial peptide of the protein of the present invention or a salt thereof can be produced by per se known procedures for peptide synthesis or by cleaving the protein with a suitable peptidase. The process for peptide synthesis may be a solid-phase synthesis and/or a liquid-phase synthesis. Namely, the objective peptide can be produced by condensing a partial peptide or amino acid capable of constituting the protein with the residual part thereof and, when the product has a protective group, the protective group is removed whereupon a desire peptide can be manufactured. The known technology for condensation and deprotection includes the procedures described in the following literature (1)–(5).

(1) M. Bodanszky and M. A. Ondetti, Peptide Synthesis, Interscience Publishers, New York, 1966

(2) Schroeder and Luebke, The Peptide, Academic Press, New York, 1965

(3) Nobuo Izumiya et al., Fundamentals and Experiments in Peptide Synthesis, Maruzen, 1975

(4) Haruaki Yajima and Shumpei Sakakibara, Biochemical Experiment Series 1, Protein Chemistry IV, 205, 1977

(5) Haruaki Yajima (ed.), Development of Drugs-Continued, 14, Peptide Synthesis, Hirokawa Shoten After the reaction, the partial peptide of the present invention can be isolated and purified by a combination of conventional purification techniques such as solvent extraction, distillation, column chromatography, liquid chromatography, and recrystallization. When the partial peptide isolated as above is in a free form, it can be converted to a suitable salt by known methods or method analogous thereto. On the other hand, when it is isolated as a salt, it can be converted to a free form or to any other salt thereof by known methods or method analogous thereto.

The DNA coding for the protein of the present invention may be any DNA comprising a nucleotide sequence encoding the protein of the present invention as mentioned above. It may also be any one of genomic DNA, genomic DNA library, cDNA derived from the tissues or cells as mentioned above, cDNA library derived from the tissues or cells as mentioned above, and synthetic DNA.

The vector for constructing a library may include bacteriophage, plasmid, cosmid, and phagemid. Furthermore, using a total RNA fraction or an mRNA fraction prepared from the tissues or cells, a direct amplification can be carried out by Reverse Transcriptase Polymerase Chain Reaction (hereinafter, referred to as RT-PCR method) technique.

Examples of the DNA coding for the protein having the amino acid sequence represented by SEQ ID NO:1 of the present invention are (1) a DNA comprising a nucleotide sequence represented by SEQ ID NO:4, or (2) a DNA which comprises a nucleotide sequence hybridizing to the nucleotide sequence represented by SEQ ID NO:4 under a highstringent condition and codes for a protein having a substantially equivalent activity to the protein comprising the amino acid sequence represented by ID No:1.

Examples of the DNA which comprises the nucleotide sequence hybridizing to the nucleotide sequence represented by SEQ ID NO:4 under a highstringent condition are a DNA comprising a nucleotide sequence of not less than about 40%, preferably not less than about 60%, more preferably not less than about 80%, for still better result, not less than about 90%, most preferably about 95% identity to the nucleotide sequence represented by SEQ ID NO:4.

Examples of the DNA coding for the protein having the amino acid sequence represented by SEQ ID NO:2 are (1) a DNA comprising a nucleotide sequence represented by SEQ ID NO:7, or (2) a DNA which comprises a nucleotide sequence hybridizing to the nucleotide sequence represented by SEQ ID NO:7 under a highstringent condition and codes for a protein having a substantially equivalent activity to the protein comprising the amino acid sequence represented by ID No:2, and so on.

Examples of the DNA which comprises the nucleotide sequence hybridizing to the nucleotide sequence represented by SEQ ID NO:7 under a highstringent condition are a DNA comprising a nucleotide sequence of not less than about 40%, preferably not less than about 60%, more preferably not less than about 80%, for still better result, not less than about 90%, most preferably about 95% identity to the nucleotide sequence represented by SEQ ID NO:7.

Examples of the DNA coding for the protein having the amino acid sequence represented by SEQ ID NO:3 are (1) a DNA comprising a nucleotide sequence represented by SEQ ID NO:10, or (2) a DNA which comprises a nucleotide sequence hybridizing to the nucleotide sequence represented by SEQ ID NO:10 under a highstringent condition and codes for a protein having a substantially equivalent activity to the protein comprising the amino acid sequence represented by ID No:3, and so on.

Examples of the DNA which comprises the nucleotide sequence hybridizing to the nucleotide sequence represented by SEQ ID NO:10 under a highstringent condition are a DNA comprising a nucleotide sequence of not less than about 40%, preferably not less than about 60%, more preferably not less than about 80%, for still better result, not less than about 90%, most preferably about 95% identity to the nucleotide sequence represented by SEQ ID NO:10.

The hybridization can be carried out by per se known methods such as the method described in Molecular Cloning, 2nd (J. Sambrook et al., Cold Spring Harbor Lab. Press, 1989) and so on. When a commercially available library is used, the hybridization can be carried out in accordance with the instructions given in the accompanying manual, and particularly, be carried out under a highstringent condition.

Under the highstringent condition, $Na^+$ concentration is at about 19 to 40 mM, preferably about 19 to 20 mM and a temperature is at about 50 to 70° C., preferably about 60 to 65° C. Particularly, the condition at about 19 mM of $Na^+$ and about 65° C. is preferred.

Preferable examples of the DNA coding for the protein comprising the amino acid sequence represented by SEQ ID NO:1 are a DNA comprising the nucleotide sequence represented by SEQ ID NO:4 and preferable examples of the DNA comprising the DNA coding for the protein having the amino acid sequence represented by SEQ ID NO:1 are a DNA comprising the nucleotide sequence represented by SEQ ID NO:5 (FIG. 1) or SEQ ID NO:6 (FIG. 2).

Preferable example of the DNA coding for the protein comprising the amino acid sequence represented by SEQ ID NO:2 are a DNA comprising the nucleotide sequence represented by SEQ ID NO:7 and preferable examples of the DNA comprising the DNA coding for the protein having the amino acid sequence represented by SEQ ID NO:2 are a DNA comprising the nucleotide sequence represented by SEQ ID NO:8 (FIG. 3) or SEQ ID NO:9 (FIG. 4).

Preferable example of the DNA coding for the protein comprising the amino acid sequence represented by SEQ ID NO:3 are a DNA comprising the nucleotide sequence represented by SEQ ID NO:10.

The DNA coding for the partial peptide of the present invention may be any DNA comprising a nucleotide sequence encoding the partial peptide of the present invention as mentioned above. It may also be any one of genomic DNA, genomic DNA library, cDNA derived from the tissues or cells as mentioned above, cDNA library derived from the tissues or cells as mentioned above, and synthetic DNA.

The vector for constructing a library may include bacteriophage, plasmid, cosmid, and phagemid. Furthermore, using a total RNA fraction or an mRNA fraction prepared from the tissues or cells, a direct amplification can be carried out by RT-PCR method.

Specifically, examples of the DNA coding for the partial peptide having at least one amino acid sequence selected from the amino acid sequences of the 8th–21st amino acid residues, 55th–59th residues (or 54th–59th residues), 93rd–102nd residues, 109th–116th residues, 118th–126th residues, 128th–134th residues, 144th–149th residues, 162nd–170th residues, 176th–182nd residues, 184th–189th residues, 193rd–213rd residues, 215th–219th residues and 228th–239th residues (or 228th–240th residues), respectively, of the amino acid sequence represented by SEQ ID NO:1 are a DNA having at least one nucleotide sequence selected from sequences of the 22nd–63rd nucleotide sequence, 163rd–177th nucleotide sequence (or 160th–177th nucleotide sequence), 277th–306th nucleotide sequence, 325th–348th nucleotide sequence, 352nd–378th nucleotide sequence, 382nd–402nd nucleotide sequence, 430th–447th nucleotide sequence, 484th–510th nucleotide sequence, 526th–546th nucleotide sequence, 550th–567th nucleotide sequence, 577th–639th nucleotide sequence, 643th–657th nucleotide sequence and 682nd–717th nucleotide sequence (or 682nd–720th nucleotide sequence), respectively, of the nucleotide sequence represented by SEQ ID NO:4 and so on.

Examples of the DNA coding for the partial peptide having at least one amino acid sequence selected from amino acid sequences of the 6th–20th amino acid residues, 53th–57th residues (or 52nd–57th residues), 91st–100th residues, 107th–114th residues, 116th–124th residues, 126th–132nd residues, 142nd–147th residues, 162nd–170th residues, 176th–182nd residues, 184th–189th residues, 192nd–212nd residues, 214th–218th residues and 227th–238th residues (or 227th–239th residues), respectively, of the amino acid sequence represented by SEQ ID NO:2 are, but not limited to, the DNAs having at least one nucleotide sequence selected from amino acid sequences of the 16th–60th nucleotide sequence, 157th–171st nucleotide sequence (or 154th–171st nucleotide sequence), 271st–300th nucleotide sequence, 319th–342nd nucleotide sequence, 346th–372nd nucleotide sequence, 376th–396th nucleotide sequence, 424th–441st nucleotide sequence, 484th–510th nucleotide sequence, 526th–546th nucleotide sequence, 550th–567th nucleotide sequence, 574th–636th nucleotide sequence, 640th–654th nucleotide sequence, and 678th–714th nucleotide sequence (or 678th–717th nucleotide sequence), respectively, of the nucleotide sequence represented by SEQ ID NO:7 and so on.

Examples of the DNA coding for the partial peptide having at least one amino acid sequence selected from amino acid sequences of the 6th–20th amino acid residues, 53th–57th residues (or 52nd–57th residues), 91st–100th residues, 107th–114th residues, 116th–124th residues, 126th–132nd residues, 142nd–147th residues, 162nd–170th residues, 176th–182nd residues, 184th–189th residues, 192nd–212nd residues, 214th–218th residues and 227th–238th residues (or 227th–239th residues), respectively, of the amino acid sequence represented by SEQ ID NO:3 are, but not limited to, the DNAs having at least one nucleotide sequence selected from amino acid sequences of the 16th–60th nucleotide sequence, 157th–171st nucleotide sequence (or 154th–171st nucleotide sequence), 271st–300th nucleotide sequence, 319th–342nd nucleotide sequence, 346th–372nd nucleotide sequence, 376th–396th nucleotide sequence, 424th–441st nucleotide sequence, 484th–510th nucleotide sequence, 526th–546th nucleotide sequence, 550th–567th nucleotide sequence, 574th–636th nucleotide sequence, 640th–654th nucleotide sequence, and 678th–714th nucleotide sequence (or 678th–717th nucleotide sequence), respectively, of the nucleotide sequence represented by SEQ ID NO:10 and so on.

Furthermore, other examples of the DNA coding for the partial peptide having an amino acid sequence of the 83rd–240th residues of the amino acid sequence represented by SEQ ID NO:1 are (1) a DNA comprising a nucleotide sequence of the 247th–720th nucleotide sequence of the nucleotide sequence represented by SEQ ID NO:4, (2) a DNA hybridized under a highstringent condition to the DNA comprising a nucleotide sequence of the 247th–720th nucleotide sequence of the nucleotide sequence represented by SEQ ID NO:4 and coding for a partial peptide which is qualitatively equivalent to the partial peptide having an amino acid sequence of the 83rd–240th residues of the amino acid sequence represented by SEQ ID No:1 in activities such as an apotosis-inducing activity and a cytotoxic activity against virus-infected cells.

Examples of the DNA which comprises the nucleotide sequence hybridizing to the nucleotide sequence corresponding to the 247th–720th nucleotide sequence of the nucleotide sequence represented by SEQ ID NO:4 under a highstringent condition are a DNA comprising a nucleotide sequence of not less than about 40%, preferably not less than about 60%, more preferably not less than about 80%, still more preferably not less than about 90%, and most preferably not less than about 95% identity to the nucleotide sequence of the 247th–720th nucleotide sequence of the nucleotide sequence represented by SEQ ID NO:4.

Other examples of the DNA coding for the partial peptide having an amino acid sequence of the 81st–239th residues of the amino acid sequence represented by SEQ ID NO:2 are (1) a DNA comprising a nucleotide sequence of the 241st–717th nucleotide sequence of the nucleotide sequence represented by SEQ ID NO:7, (2) a DNA hybridized under a highstringent condition to the DNA comprising a nucleotide sequence of the 241st–717th nucleotide sequence of the nucleotide sequence represented by SEQ ID NO:7 and coding for a partial peptide which is qualitatively equivalent to the fragment peptide having an amino acid sequence of the 81st–239th amino acid residues of the amino acid sequence represented by SEQ ID NO:2 in activities such as an apotosis-inducing activity and a cytotoxic activity against virus-infected cells.

Examples of the DNA which comprises the nucleotide sequence hybridizing to a DNA having a nucleotide sequence of the 241st–717th nucleotide sequence of the nucleotide sequence represented by SEQ ID NO:7 are a DNA comprising a nucleotide sequence of not less than about 40%, preferably not less than about 60%, more preferably not less than about 80%, still more preferably not less than about 90%, and most preferably not less than about 95% identity to the nucleotide sequence of the 241st–717th nucleotide sequence of the nucleotide sequence represented by SEQ ID NO:7.

Other examples of the DNA coding for the partial peptide having an amino acid sequence of the 81st–239th residues of the amino acid sequence represented by SEQ ID NO:3 are (1) a DNA comprising a nucleotide sequence of the 241st–717th nucleotide sequence of the nucleotide sequence represented by SEQ ID NO:10, (2) a DNA hybridized under a highstringent condition to the DNA comprising a nucleotide sequence of the 241st–717th nucleotide sequence of the nucleotide sequence represented by SEQ ID NO:10 and coding for a partial peptide which is qualitatively equivalent to the fragment peptide having an amino acid sequence of the 81st–239th amino acid residues of the amino acid sequence represented by SEQ ID NO:3 in activities such as an apotosis-inducing activity and a cytotoxic activity against virus-infected cells.

Examples of the DNA which comprises the nucleotide sequence hybridizing to a DNA having a nucleotide sequence of the 241st–717th nucleotide sequence of the nucleotide sequence represented by SEQ ID NO:10 are a DNA comprising a nucleotide sequence of not less than about 40%, preferably not less than about 60%, more preferably not less than about 80%, still more preferably not less than about 90%, and most preferably not less than about 95% identity to the nucleotide sequence of the 241st–717th nucleotide sequence of the nucleotide sequence represented by SEQ ID NO:10.

The method of hybridization and the highstringent condition are same as mentioned above.

More specifically, the DNA coding for the partial peptide having an amino acid sequence of the 83rd–240th residues of the amino acid sequence represented by SEQ ID NO:1 includes a DNA having a nucleotide sequence of the 247th–720th nucleotide sequence of the nucleotide sequence represented by SEQ ID NO:4. The DNA coding for the partial peptide having an amino acid sequence of the 81st–239th residues of the amino acid sequence represented by SEQ ID NO:2 includes the DNA having a nucleotide sequence of the 241st–717th nucleotide sequence of the nucleotide sequence represented by SEQ ID NO:7. The DNA coding for the partial peptide having an amino acid sequence of the 81st–239th residues of the amino acid sequence represented by SEQ ID NO:3 includes the DNA having a nucleotide sequence of the 241st–717th nucleotide sequence of the nucleotide sequence represented by SEQ ID NO:10.

The DNA encoding the protein or the partial peptide of the present invention can be cloned either by PCR amplification using synthetic DNA primers having a partial nucleotide sequence of the DNA coding for the protein or by hybridization using the DNA inserted in a suitable vector and labeled DNA fragment or synthetic DNA coding for a part or full region of the protein or the partial peptide of the present invention. The hybridization can be carried out by the method described in Molecular Cloning, 2nd (J. Sambrook et al., Cold Spring Harbor Lab. Press, 1989). When a commercially available DNA library is used, the instructions given in the accompanying manual can be followed.

The substitution of the nucleotide sequence of the DNA can be carried out by the per se known method such as Gapped duplex method, Kunkel method and so on by using the known kits such as Mutan™-G (Takara corporation), Mutan™-K (Takara corporation) and so on.

The cloned DNA coding for the protein or the partial peptide of the present invention can be used directly or after digestion with a restriction enzyme or after addition of a linker depending on purposes. This DNA may have ATG as the translation initiation codon at the 5' end and TAA, TGA, or TAG as the termination codon at the 3' end. The translation initiation and termination codons can be added by means of suitable DNA adapters.

An expression vector for the protein of the present invention can be constructed by, for example, (a) cutting out an objective DNA fragment from the DNA for the protein of the present invention and (b) ligating the objective DNA fragment with the downstream of a promoter in a suitable expression vector.

The vector may include plasmids derived from *Escherichia coli*, e.g., pBR322, pBR325, pUC12, pUC13, etc.; plasmids derived from *Bacillus subtilis*, e.g., pUB110, pTP5, pC194, etc.; plasmids derived from yeasts e.g., pSH19, pSH15, etc.; bacteriophages such as λ-phage: animal virus such as retrovirus, vaccinia virus, etc.; insect virus; and other vecters such as pA1-11, pXT1, pRc/CMV, pRc/RSV, pcDNAI/Neo and so on.

According to the present invention, any promoter can be used as long as it is appropriate for the host cell which is used for expressing a gene. When the host is an animal cell, the promoter include SRa promoter, SV40 promoter, LTR promoter, CMV (cytomegalovirus) promoter, HSV-TK promoter, etc., and CMV promoter and SRa promoter are preferably used. When the host for the transformation is

*Escherichia coli*, the promoter are preferably trp promoter, lac promoter, recA promoter, $\lambda AP_L$ promoter, lpp promoter, T7 promoter, etc. When the host for the transformation is Bacillus, the promoter are preferably SPO1 promoter, SPO2 promoter, penP promoter, etc. When the host is a yeast, the promoter are preferably PHO5 promoter, PGK promoter, GAP promoter, ADH promoter, AOX1 promoter, etc. When the host is an insect cell, the promoter include polyhedrin promoter, P10 promoter, etc.

The expression vectors may, if necessary, further comprise enhancers, splicing signals, polyadenylation signals, selective markers, SV40 duplicate origin (hereinafter referred to as SV40 ori). Examples of selective markers are dihydrofolate reductase (hereinafter referred to as dhfr gene, ampicillin resistant gene (hereinafter referred to as Ampr), neomycin-resistant gene (hereinafter referred to as Neo) and so on. The dhfr gene gives methotrexate (MTX) registant and Neo gives G418 resistant. Particularly, when the dhfr gene is used as a selective marker against dhfr gene-deficient chinese hamster cell line, cells transfected by the objective gene can be selected in a thymidine-free medium.

Furthermore, an appropriate signal sequence for a host can be added to the N-terminal side of the protein. When the host is *Escherichia coli*, the utilizable signal sequences may include PhoA signal sequence, OmpA signal sequence, etc. When the host is Bacillus, they may include α-amylase signal sequence, subtilisin signal sequence, etc. When the host is a yeast, they may include MFα signal sequence, SUC2 signal sequence, etc. When the host is an animal cell, they may include insulin signal sequence, α-interferon signal sequence, antibody molecule signal sequence, etc.

A transformant or transfectant is obtained by using the vector thus constructed, which carries the DNA coding for the protein of the present invention.

The host may be, for example, Escherichia species, Bacillus species, yeast cells, insect cells, insects, animal cells, etc.

Examples of Escherichia species include *Escherichia coli* K12-DH1 (Proceedings of the National Academy of Sciences of the United State of America, Vol. 60, 160 (1968)), JM103 (Nucleic Acids Research, Vol. 9, 309 (1981)), JA221 (Journal of Molecular Biology, Vol. 120, 517 (1978)), HB101 (Journal of molecular Biology, Vol, 41, 459 (1969)), C600 (Genetics, Vol. 39, 440 (1954)), etc.

Examples of Bacillus species are, for example, *Bacillus subtilis* MI114 (Gene, Vol. 24, 255 (1983)), 207–21 (Journal of Biochemistry, Vol. 95, 87 (1984)), etc.

Examples of yeast cells are, for example, *Saccharomyces cerevisiae* AH22, AH22R⁻, NA87-11A, DKD-5D or 20B-12, *Schizosachcaromvces pombe* NCYC1913 or *Pichia pastoris* KM71, etc.

Examples of insect cells are, for example, *Spodoptera frugiperda* cell (Sf cell), MG1 cell derived from a center intestine of *Trichoplusia ni*, High Five™ cell derived from eggs of *Trichoplusia ni*, *Mamestra brassicae*-derived cell, *Estigmena acrea*-derived cell and so on when virus is AcNPV; and *Bombyx mori* N cell (BmN cell) and so on when virus is BmNPV. Examples of the Sf cell are, for example, Sf9 cell (ATCC CRL 1711), Sf21 cell [both, Vaughn J. L. et al., In Vivo, 13, 213–217(1977)] and so on.

Examples of insects include a larva of silkworm (*Bombyx mori* larva) (Maeda et al., Nature, 315, 592(1985)).

Examples of animal cells are, for example, monkey-derived COS-7 cell line, Vero cell line, Chinese hamster ovary cell line (hereinafter referred to as CHO cell), dhfr gene-deficient Chinese hamster cell line (hereinafter referred to as CHO(dhfr⁻) cell), mouse L cell, mouse AtT-20, mouse myeloma cell, rat GH3, human FL, 293 cell, C127 cell, BALB3T3 cell, Sp-2/O cell, etc. Among them, CHO cell, CHO(dhfr⁻) cell, 293 cell, etc. are preferred.

Depending on host cells used, transformation is carried out using standard techniques appropriate to such cells.

Transformation of Escherichia species can be carried out in accordance with methods as disclosed in, for example, Proceedings of the National Academy of Sciences of the United State of America, Vol. 69, 2110 (1972), and Gene, Vol. 17, 107 (1982), etc. Transformation of Bacillus species can be carried out in accordance with methods as disclosed in, for example, Molecular & General Genetics, Vol. 168, 111 (1979), etc.

Transformation of yeast cells can be carried out in accordance with methods as disclosed in, for example, Methods in Enzymology, 194, 182–187(1991), etc. Transformation of insect cells or insects can be carried out in accordance with methods as disclosed in, for example, Bio/Technology, 6, 47–55, (1988).

Transformation of animal cells can be carried out by methods as disclosed in, for example, Cell Engineering, separate vol. 8, New Cell Engineering Experiment Protocol, 263–267(1995) (Shujun Company), Virology, Vol. 52, 456 (1973), etc.

In introducing the expression vector into cells, known methods such as a calcium phosphate method (Graham, F. L. and van der Eb, A. J.: Virology, 52, 456–467(1973)), an electroporation (Neumann, E. et al., EMBO Journal, 1,841–845(1982)), etc. may be used.

The transformants or transfectants wherein the expression vector carrying the DNA coding for the protein can be obtained according to the aforementioned techniques.

Examples of methods for expressing the protein of the present invention stably using animal cells are a method for selecting the cells wherein the above-mentioned expression vector is integrated on the chromosome by means of clone selection. Briefly, the transformant is first selected using the above-mentioned selective marker as an index for selection. Then the animal cell obtained as such using the selective marker is repeatedly subjected to a clone selection to establish an aminal cell strain which stably exhibits a high ability of expressing the protein of the present invention. When a dhfr gene is used as a selective marker, the resistant cells are selected from a culture with a sequentially increased MTX concentration to amplify the DNA coding for the protein of the present invention with dhfr gene in the cells whereby an animal cell strain exhibiting far higher expression can be obtained.

The protein of the present invention or a salt thereof can be also manufactured by culturing the transformant under a condition where the DNA coding for the protein of the present invention can be expressed to express and accumulate the protein of the present invention.

Culture of the transformants (transfectants) of Escherichia or Bacillus species can be carried out preferably in a liquid culture medium. The culture medium may contains carbon sources, nitrogen sources, minerals, etc. which are necessary for growing the transformants. The carbon sources may include glucose, dextrin, soluble starch, sucrose, etc. The nitrogen sources may include organic or inorganic substances such as ammonium salts, nitrates, corn steep liquor, peptone, casein, meat extracts, bean-cakes, potato extracts, etc. Examples of the minerals may include calcium chloride, sodium dihydrogen phosphate, magnesium chloride, etc. It is further allowable to add yeast extracts, vitamines, growth-promoting factors, etc. It is suitable that the pH of culture medium is at about 5 to 8.

The culture medium for Escherichia species is, for example, preferably M9 medium which contains glucose and casamino acid (Miller, Journal of Experiments in Molecular Genetics, 431–433, Cold Spring Harbor Laboratory, New York, (1972). If necessary, drugs such as 3β-indolyl acrylic acid can be added to the medium to improve efficiency of the promoter. In the case of Escherichia species as a host, the culture is carried out usually at about 15 to 43° C. for about 3 to 24 hours. As required, aeration and stirring may be applied. In the case of Bacillus species as a host, the culture is carried out usually at about 30 to 40° C. for about 6 to 24 hours. As required, aeration and stirring may also be applied.

In the case of yeast transformant cells, the culture medium used may include, for example, Burkholder minimum medium (Bostian, K. L. et al., Proceedings of the National Academy of Sciences of the United State of America, Vol. 77, 4505 (1980)), SD medium containing 0.5% casamino acid (Bitter, G. A. et al., Proceedings of the National Academy of Sciences of the United State of America, Vol. 81, 5330 (1984)), etc. It is preferable that the pH of the culture medium is adjusted to be from about 5 to 8. The culture is carried out usually at about 20 to 35° C. for about 24 to 72 hours. As required, aeration and stirring may be applied.

In the case of the transformants (or transfectants) of insect cells or insects, the culture medium used may include the Grace's insect medium supplemented with additives such as inactivated 10% bovine serum (Grace, T. C. C., Nature, 195, 788 (1962)). It is preferable that the pH of the culture medium is adjusted to be about 6.2 to 6.4. The culture is usually carried out at about 27° C. for about 3 to 5 days. As desired, aeration and stirring may be applied.

In the case of the transformants (or transfectants) of animal cells, the culture medium used may include MEM medium (Science, Vol. 122, 501 (1952)), DMEM medium (Virology, Vol. 8, 396 (1959)), RPMI 1640 medium (Journal of the American Medical Association, Vol. 199, 519 (1967)), 199 medium (Proceedings of the Society of the Biological Medicine, Vol. 73, 1 (1950)), etc. which are containing, for example, about 5 to 20% of fetal calf serum. It is preferable that the pH is from about 6 to 8. The culture is usually carried out at about 30 to 40° C. for about 15 to 72 hours. As required, medium exchange, aeration and stirring may be applied. Especially when CHO (dhfr⁻) cells and dhfr selective marker gene are used, it is preferred to use DMEM medium containing dialyzed fetal bovine serum which rarely contains thymidine.

Separation and purification of the protein from the above-mentioned cultures can be carried out according to methods described herein below.

To extract the protein from the cultured microorganisms, insects=cells or animal cells, the microorganisms, insect cells or animal cells are collected by known methods after the culture, suspended in a suitable buffer solution, disrupted by sonication, lysozyme treatment and/or freezing and thawing, etc. and, then, a crude protein extract is obtained by centrifugation or filtration. Other conventional extraction or isolation methods can be applied. The buffer solution may contain a protein-denaturing agent such as urea or guanidine hydrochloride or a surfactant such as Triton X-100™.

In the case where proteins are secreted into culture media, supernatants are separated from the microorganisms, insect cells or animal cells after culture and collected by known methods. The culture supernatant containing the protein can be purified by suitable combinations of known methods for separation, isolation and purification. The known methods of separation, isolation and purification may include methods which utilizes a difference in solubility, such as salting out or sedimentation with solvents, methods which utilizes chiefly a difference in the molecular size or weight, such as dialysis, ultrafiltration, gel filtration and SDS-polyacrylamide gel electrophoresis, methods utilizing a difference in the electric charge, such as ion-exchange chromatography, methods utilizing specific affinity such as affinity chromatography, methods utilizing a difference in the hydrophobic property, such as reversed-phase high-performance liquid chromatography, and methods utilizing a difference in the isoelectric point such as isoelectric electrophoresis, etc.

In cases where the protein thus obtained is in a free form, the free-form protein can be converted to a salt thereof by known methods or method analogous thereto. In case, where the protein thus obtained is in a salt form vice versa, the protein salt can be converted to a free form or to any other salt thereof by known methods or method analogous thereto.

The protein produced by the transformant can be arbitrarily modified or a polypeptide can be partly removed therefrom, by a suitable protein-modifying enzyme before or after the purification. The protein-modifying enzyme may include trypsin, chymotrypsin, arginyl endopeptidase, protein kinase, glycosidase, etc. The amount of the protein of the present invention thus obtained can be measured by a binding assay with a labeled ligand or by an enzyme immunoassays (enzyme linked immunoassays) using specific antibodies.

The antibodies against the protein of the present invention, its partial peptide or a salt thereof are any antibodies such as polyclonal antibodies and monoclonal antibodies which can recognize the protein of the present invention, its partial peptide or a salt thereof (hereinafter referred to as the protein of the present invention).

The antibodies against the protein of the present invention, its partial peptide or a salt thereof may be manufactured by methods per se known to those of skill in the art or methods similar thereto, using the protein of the present invention as antigen. For example, polyclonal antibodies can be manufactured by the method as given below.

Preparation of Monoclonal Antibody (a) Preparation of Monoclonal Antibody-Producing Cells The protein of the present invention is administered to warm-blooded animals either solely or together with carriers or diluents to the site favorable for antibody production. In order to potentiate the antibody productivity upon the administration, complete Freund's adjuvants or incomplete Freund's adjuvants may be administered. The administration is usually carried out once every 2 to 6 weeks and 2 to 10 times in total. Examples of the applicable warm-blooded animals are monkeys, rabbits, dogs, guinea pigs, mice, rats, sheep, goats and chickens. The use of mice and rats is preferred.

In establishing cells which produce monoclonal antibodies, an animal with the detectable antibody titer is selected from animals (e.g. mice) immunized with antigens, then spleen or lymph node is collected after 2 to 5 days from the final immunization and antibody-producing cells contained therein are fused with myeloma cells derived from homogeneous or heterogeneous animals to obtain monoclonal antibody-producing hybridomas. Measurement of the antibody titer in antisera may, for example, be carried out by reacting a labeled protein, which will be mentioned later, with the antiserum followed by measuring the binding activity of the labeling agent with the antibody. The cell fusion may be carried out, for example, by a method of Koehler and Milstein (Nature, 256, 495, 1975). Examples of the fusion accelerator are polyethylene glycol (PEG), Sendai virus, etc. and the use of PEG is preferred.

Examples of the myeloma cells are those derived from warm-blooded animals such as NS-1, P3U1, SP2/0, AP-1, etc. and the use of P3U1 is preferred. The preferred fusion ratio of the numbers of antibody-producing cells used (spleen cells) to the numbers of myeloma cells is within a range of about 1:1 to 20:1. When PEG (preferably, PEG 1000 to PEG 6000) is added in a concentration of about 10 to 80% followed by incubating at 20 to 40° C., preferably, at 30 to 37° C., for 1 to 10 minutes, an efficient cell fusion can be carried out.

Various methods may be applied for screening a hybridoma which produces a monoclonal antibody. For example, a supernatant of hybridoma culture is added to a solid phase (e.g. microplate) to which the protein antigen is adsorbed either directly or with a carrier, then anti-immunoglobulin antibody (anti-mouse immunoglobulin antibody is used when the cells used for the cell fusion are those of mouse) which is labeled with a radioactive substance, an enzyme or the like, or protein A is added thereto and then monoclonal antibodies bound on the solid phase are detected; or a supernatant of the hybridoma culture is added to the solid phase to which anti-immunoglobulin or protein A is adsorbed, then the protein labeled with a radioactive substance or an enzyme is added and monoclonal antibodies bound with the solid phase is detected.

Selection and cloning of the monoclonal antibody-producing hybridoma may be carried out by methods per se known to those of skill in the art or methods similar thereto. Usually, it is carried out in a medium for animal cells, containing HAT (hypoxanthine, aminopterin and thymidine). With respect to a medium for the selection, for the cloning and for the growth, any medium may be used so far as hybridoma is able to grow therein. Examples of the medium are an RPMI 1640 medium (Dainippon Pharmaceutical Co., Ltd., Japan) containing 1 to 20% (preferably 10 to 20%) of fetal calf serum (FCS), GIT medium (Wako Pure Chemical, Japan) containing 1 to 20% of fetal calf serum and a suitable serum-free medium for hybridoma (SFM-101; Nissui Seiyaku, Japan). The culture temperature is usually 20 to 40° C. and, preferably, about 37° C. The culture period is usually from five days to three weeks and, preferably, one to two weeks. The culture is usually carried out in 5% carbon dioxide gas. The antibody titer of the supernatant of the hybridoma culture may be measured by the same manner as in the above-mentioned measurement of the antibody titer in the antiserum.

(b) Purification of the Monoclonal Antibody

The separation and purification of the monoclonal antibody may be carried out by methods for separating/purifying immunoglobulin such as salting-out, precipitation with alcohol, isoelectric precipitation, electrophoresis, adsorption/deadsorption using ion exchangers such as DEAE, ultracentrifugation, gel filtration, specific purifying methods in which only an antibody is collected by treatment with an active adsorbent such as an antigen-binding solid phase, protein A or protein G and the bond is dissociated whereupon the antibody is obtained.

Preparation of a Polyclonal Antibody

The polyclonal antibody of the present invention can be produced by per se known methods or methods analogous thereto. The method comprises preparing an immunogen (antigen protein) per se or a conjugate of an imunogen with a carrier protein, immunizing a warm-blooded animal in the same manner as described for the production of the monoclonal antibody, harvesting a fraction containing the antibody against the protein of the present invention from the immunized animal, and purifying the harvested antibody.

Referring to the immunogen-carrier protein conjugate for use in the immunization of a warm-blooded animal, the kind of carrier protein and the ratio of the carrier and hapten are not particularly restricted only if the production of the antibody against the hapten conjugated with the particular carrier protein and used for immunization proceeds efficiently. Thus, for example, bovine serum albumin, bovine thyroglobulin, hemocyanine, or the like is coupled in the weight ratio of about 0.1 to 20, preferably about 1 to about 5, to unity of the hapten.

A variety of condensing agents can be used for this coupling between the hapten and the carrier. Thus, for example, a glutaraldehyde, carbodiimide, maleimide, or a thiol or dithiopyridyl group-containing active ester reagent can be employed.

The condensation reaction product is administered to a warm-blooded animal at a site favorable for antibody production, either as it is alone or together with a carrier or diluent. Enhancing antibody production, complete Freund's adjuvant or incomplete Freund's adjuvant may be administered. Administration is carried out generally once in about 2 to 6 weeks for a total of about 3 to 10 times.

The polyclonal antibody can be harvested from the blood, ascites fluid, or other body fluid, preferably from the blood, of the host warm-blooded animal.

The polyclonal antibody titer in the antiserum can be determined in the same manner as the determination of monoclonal antibody described hereinbefore. The separation and purification of the polyclonal antibody can be carried out by the same method as that described for the separation and purification of monoclonal antibody.

The antisense DNA having a nucleotide sequence complementary or substantially complementary to the DNA coding for the protein or the partial peptide of the present invention (hereinafter referred to as the DNA of the present invention) can be any antisense DNA having a nucleotide sequence complementary or substantially complementary to that of the DNA of the present invention and capable of suppressing expression of the DNA.

The nucleotide sequence substantially complementary to the DNA of the present invention may, for example, be a nucleotide sequence having an identity of not less than about 40%, preferably not less than about 60%, more preferably not less than about 80%, and for still better results, not less than about 90%, most preferably about 95% to the total nucleotide sequence or partial nucleotide sequence of the nucleotide sequence complementary to that the DNA of the present invention. Particularly preferred is an antisense DNA having an identity of not less than about 40%, preferably not less than about 60%, and more preferably not less than about 80%, and for still better results, not less than about 90%, most preferably about 95% to the nucleotide sequence of the domain, of the complete nucleotide sequence complementary to that of the DNA of the present invention, which encodes the N-terminal region of the protein of the present invention (e.g. the nucleotide sequence of the domain around the initiation codon). The antisense DNA can be synthesized using a known DNA synthesis hardware.

The protein, the partial peptide or a salt thereof of the present invention has activities such as an apotosis-inducing activity, a cytotoxic activity against virus-infected cells and so on. Therefore, the protein, the partial peptide, and salt of the present invention can be used in a variety of application.

Uses for the protein, the partial peptide or a salt thereof (hereinafter sometimes referred to collectively as the protein, etc. of the present invention), the DNA coding for the protein of the present invention (hereinafter sometimes referred to briefly as the DNA of the present invention), the antibody against the protein, etc. of the present invention (hereinafter sometimes referred to as the antibody of the present invention), and the antisense DNA of the present invention are now described.

(1) Medicinal Products Such as Therapeutic and Prophylactic Drugs for Various Diseases For example, when there is a patient whose Fas ligand in body cannot function sufficiently or normally because of a decrease or a defect in the Fas ligand in vivo, the role of the Fas ligand for said patient can be expected sufficiently or normally by:

(a) administering the DNA coding for the protein, etc. of the present invention to the patient to express it;

(b) inserting the DNA coding for the protein, etc. of the present invention into cells to express it and transplanting the cells to said patient, or (c) administering the protein, etc. of the present invention to the patient.

The protein, etc. of the present invention and the DNA of the present invention are useful for therapeutic or prophylactic agent for various diseases such as cancer (e.g. breast cancer, prostate cancer, ovary cancer, follicular lymphoma, cancer associated with p53 mutation, brain tumor, bladder cancer, uterocervical cancer, colon cancer (colorectal cancer), non-small cell carcinoma of lung, small cell carcinoma of lung, stomach cancer, etc.), viral or bacterial infection (e.g. incipient stage of AIDS virus infection, herpes virus infection, adenovirus infection, poxvirus infection, varicella-zoster virus infection, human papillomavirus infection, etc.), *Helicobacter pylori* infection, invasive staphylococcia, hepatitis (e.g. hepatitis A, hepatitis C, etc.), nephritis, autoimmune disease (e.g. systemic lupus erythematosus, immune complex glomerulonephritis, etc.), bone disease (e.g. rheumatoid arthritis such as abnormal proliferation of synuvial cells in rheumatism, etc.), atherosclerosis, and pain, preferably cancer (e.g. breast cancer, prostate cancer, ovary cancer, follicular lymphoma, cancer associated with p53 mutation, etc.), viral or bacterial infection (e.g. incipient stage of AIDS virus infection, herpes virus infection, adenovirus infection, poxvirus infection, etc.), hepatitis, nephritis, rheumatoid arthritis, atherosclerosis, autoimmune disease (e.g. systemic lupus erythematosus, immune complex glomerulonephritis, etc.).

When the DNA of the present invention is used as the above-mentioned pharmaceutical agent, said DNA may be used alone or after inserting it into a suitable vector such as retrovirus vector, adenovirus vector, adenovirus-associated virus vector, pox virus etc. followed by subjecting the product vector to a conventional means. The DNA can also be administered as "naked" DNA, with physiologically acceptable carriers such as adjuvants to assist in uptake, by "gene" gun or by a catheter such as a catheter with a hydrogel.

If one wishes to use the protein, etc. of the present invention, one would use it in a purified form, preferably in a purity of at least 90%, more preferably at least 95%, still more preferably at least 98% and most preferably at least 99%.

For example, the protein, etc. of the present invention can be used orally in the form of tablets which may be sugar coated as necessary, capsules, elixirs, microcapsules etc., or non-orally in the form of injectable preparations such as aseptic solutions and suspensions in water or other pharmaceutically acceptable liquids. These preparations can be produced by mixing the protein, etc. of the present invention with physiologically acceptable carriers, flavoring agents, excipients, vehicles, antiseptics, stabilizers, binders etc. in unit dosage forms required for generally accepted manners of pharmaceutical preparation. Active ingredient contents in these preparations are set so that an appropriate dose within the specified range is obtained.

Additives which can be mixed in tablets, capsules etc. include binders such as gelatin, corn starch, tragacanth and gum arabic, excipients such as crystalline cellulose, swelling agents such as corn starch, gelatin and alginic acid, lubricants such as magnesium stearate, sweetening agents such as sucrose, lactose and saccharin, and flavoring agents such as peppermint, akamono oil and cherry. When the unit dosage form is the capsule, the above-mentioned materials may further incorporate liquid carriers such as oils and fats. Sterile compositions for injection can be formulated by ordinary methods of pharmaceutical preparation such as by dissolving or suspending active ingredients, naturally occurring vegetable oils such as sesame oil and coconut oil, etc. in vehicles such as water for injection to create pharmaceutical compositions.

Aqueous liquids for injection include physiological saline and isotonic solutions containing glucose and other auxiliary agents, e.g., D-sorbitol, D-mannitol and sodium chloride, and may be used in combination with appropriate dissolution aids such as alcohols, e.g., ethanol, polyalcohols, e.g., propylene glycol and polyethylene glycol, nonionic surfactants, e.g., polysorbate 80™ and HCO-50 etc. Oily liquids include sesame oil and soybean oil, and may be used in combination with dissolution aids such as benzyl benzoate and benzyl alcohol. Furthermore the above-mentioned materials may also be formulated with buffers, e.g., phosphate buffer and sodium acetate buffer; soothing agents, e.g., benzalkonium chloride, procaine hydrochloride; stabilizers, e.g., human serum albumin, polyethylene glycol; preservatives, e.g., benzyl alcohol, phenol; antioxidants etc. Normally, an appropriate ample is filled in with the thus-prepared pharmaceutical composition such as an injectable liquid.

The vector comprising the DNA of the present invention can be formulated as well as mentioned above, and usually can be used non-orally.

Because the thus-obtained preparation is safe and of low toxicity, it can be administered to humans or mammals (e.g., rat, mouse, guinia pig, rabbit, sheep, pig, bovine, horse, cat, dog, monkey, etc.).

The dose of the protein, etc. of the present invention may vary depending on subject disease, subject of administration, way of administration, and so on. When the protein, etc. of the present invention is used, for example, for treating cancer by oral administration, the dose of the protein, etc. of the present invention is normally about 0.1 to 100 mg, preferably 1.0 to 50 mg, and more preferably 1.0 to 20 mg per day for an adult (weighing 60 kg). When the protein, etc. of the present invention is used, for example, for treating cancer by non-oral administration, it is advantageous to administer the protein, etc. of the present invention in the form of injectable preparation at a daily dose of about 0.01 to 30 mg, preferably about 0.1 to 20 mg, and more preferably about 0.1 to 10 mg per administration by an intravenous injection for an adult (weighing 60 kg), depending on subject of administration, subject disease and so on. For other animal species, corresponding does as converted per 60 kg weight can be administered.

(2) Gene Diagnostic Agent

By using the DNA of the present invention as a probe, for instance, an abnormality (gene abnormality) of the DNA or mRNA coding for the protein of the present invention or its partial peptide in humans or mammals (e.g. rat, mouse, guinea pig, rabbit, sheep, swine, bovine, horse, cat, dog, monkey, chimpanzee, etc.) can be detected. Therefore, the DNA of the present invention is useful as a gene diagnostic agent for the damage to the DNA or mRNA, mutation thereof, or decreased expression thereof, or increased expression or overexpression of the DNA or mRNA.

For example, when the increase of the mRNA coding for the protein, etc. or the increase of the protein, etc. of the present invention is detected, it may be lead to the diagnosis of acquired immunodeficiency syndrome (AIDS), inflammation, neurodegenerative disease due to osteomyelodysplasia, ischemic disease, destruction of joint tissues in rheumatism, hepatitis, autoimmune disease, cardiomyopathy, diabetes, diabetic complications, influenza, glomerulonephritis or uncerative colitis, particulary, AIDS, inflammation, destruction of joint tissues in rheumatism, hepatitis or autoimmune disease.

On the other hand, the deficit or lack of the DNA or mRNA or the decrease of the protein, etc. is detected, it may be lead to the diagnosis of cancer, viral infection, *Helicobacter pylori* infection, invasive staphylococcia, hepatitis, nephritis, autoimmune disease, bone disease, atherosclerosis or pain.

The above-mentioned gene diagnosis using the DNA of the present invention can be carried out by, for example, the per se known Northern hybridization assay or PCR-SSCP assay (Genomics, 5, 874–879 (1989); Proceedings of the National Academy of Sciences of the United States of America, 86, 2766–2770 (1989)).

When increase in expression of the mRNA coding for the protein, etc. of the present invention is detected by Northern hybridization assay, it may lead, with high probability, to the diagnosis of AIDS, inflammation, neurodegenerative disease due to osteomyelodysplasia, ischemic disease, destruction of joint tissues in rheumatism, hepatitis, autoimmune disease, cardiomyopathy, diabetes, diabetic complications, influenza, glomerulonephritis or uncerative colitis, particulary, AIDS, inflammation, destruction of joint tissues in rheumatism, hepatitis or autoimmune disease.

When decrease in expression of the mRNA is detected, it may lead, with high probability, to the diagnosis of cancer, viral infection, *Helicobacter pylori* infection, invasive staphylococcia, hepatitis, nephritis, autoimmune disease, bone disease, atherosclerosis or pain.

When a mutation of the DNA is detected by the PCR-SSCP assay, it may lead, with high probability to diagnosis of cancer, viral infection, *Helicobacter pylori* infection, invasive staphylococcia, hepatitis, nephritis, autoimmune disease, bone disease, atherosclerosis, pain, AIDS, inflammation, neurodegenerative disease due to osteomyelodysplasia, ischemic disease, destruction of joint tissues in rheumatism, cardiomyopathy, diabetes, diabetic complications, influenza, glomerulonephritis or uncerative colitis and so on.

(3) Quantitative Determination of the Protein of the Present Invention

The antibody of the present invention is capable of specifically recognizing the protein, etc. of the present invention and, accordingly, it can be used for quantitative determination of the protein, etc. of the present invention in test liquid samples and particularly for quantitative determination by sandwich immunoassays.

Thus, the present. invention provides, for example, the following methods:

(i) a quantitative determination of the protein, etc. of the present invention in a test liquid sample, which comprises
  (a) competitively reacting the test liquid sample and a labeled protein, etc. of the present invention with the antibody of the present invention, and
  (b) measuring the ratio of the labeled protein, etc. of the present invention binding with said antibody; and (ii) a quantitative determination of the protein, etc. of the present invention in a test liquid sample, which comprises
  (a) reacting the test liquid sample with an antibody immobilized on an insoluble carrier and a labeled antibody simultaneously or continuously, and
  (b) measuring the activity of the labeling agent on the insoluble carrier, wherein one antibody is capable of recognizing the N-terminal region of the protein, etc. of the present invention while another antibody is capable of recognizing the C-terminal region of the protein, etc. of the present invention.

When the monoclonal antibody of the present invention recognizing a protein, etc. of the present invention (hereinafter, sometimes referred to as "monoclonal antibody of the present invention") is used, the quantity of the protein, etc. of the present invention can be measured and, moreover, the protein, etc. of the present invention can be detected by means of a tissue staining, etc. as well. For such an object, antibody molecules per se may be used, or $F(ab')_2$ Fab' or Fab fractions of the antibody molecule may also be used. There is no particular limitation for the measuring method using the antibody of the present invention and any measuring method may be used so far as it relates to a method in which the amount of antibody, antigen or antibody-antigen complex, depending on or corresponding to the amount of antigen, e.g. the amount of the protein, etc. of the present invention in the liquid sample to be measured, is detected by a chemical or a physical means and then calculated using a standard curve prepared by a standard solution containing the known amount of antigen. For exmaple, nephrometry, competitive method, immunometric method and sandwich method are suitably used and, in terms of sensitivity and specificity, the sandwich method which will be described herein later is particularly preferred.

Examples of the labeling agent used in the measuring method using the labeling substance are radioisotopes, enzymes, fluorescent substances, luminescent substances, colloids, magnetic substances, etc. Examples of the radioisotope are $[^{125}I]$, $[^{125}I]$, $[^{3}H]$ and $[^{14}C]$. Preferred examples of the enzyme are those which are stable and with much specific activity, such as β-galactosidase, β-glucosidase, alkaline phosphatase, peroxidase and malate dehydrogenase. Examples of the fluorescent substance are fluorescamine, fluorescein isothiocyanate, etc. Examples of the luminescent substance are luminol, luminol derivatives, luciferin, lucigenin, etc. Further, a biotin-avidin system may also be used for binding an antibody or antigen with a labeling agent.

In insolubilization (immobilization) of antigens or antibodies, a physical adsorption may be used or a chemical binding which is usually used for insolubilization or immobilization of proteins or enzymes may be used as well. Examples of the carrier are insoluble polysaccharides such as agarose, dextran and cellulose; synthetic resins such as polystyrene, polyacrylamide and silicone; glass; etc.

In a sandwich method, the test liquid is allowed to react with an insolubilized monoclonal antibody of the present invention (the first reaction), then it is allowed to react with another labeled monoclonal antibody of the present invention (the second reaction) and the activity of the labeling agent on the insoluble carrier is measued whereupon the amount of the protein, etc. of the present invention in the test liquid can be determined. The first reaction and the second reaction may be conducted reversely or simultaneously or they may be conducted with an interval. The type of the labeling agent and the method of insolubilization may be the same as those mentioned hereinbefore. In the immunoassay by means of a sandwich method, it is not always necessary that the antibody used for the labeled antibody and the antibody for the solid phase is one type or one species but, with an object of improving the measuring sensitivity, etc., a combination of two or more antibodies may be used as well.

In the method of measuring the protein, etc. of the present invention by the sandwich method of the present invention, the preferred monoclonal antibodies of the present invention used for the first and the second reactions are antibodies wherein their sites binding to the protein of the present invention are different from each other. Thus, antibodies used in the first and the second reactions are those wherein, when an antibody used in the second reaction recognizes the C-terminal region of the protein, etc. of the present invention, then another antibody recognizing the site other than C-terminal regions, e.g. recognizing the N-terminal region, is preferably used in the first reaction.

The monoclonal antibody of the present invention may be used in a measuring system other than the sandwich method such as a competitive method, an immunometric method and a nephrometry. In the competitive method, an antigen in the test solution and a labeled antigen are allowed to react with an antibody in a competitive manner, then an unreacted labeled antigen (F) and a labeled antigen (B) binding with an antibody are separated (i.e. B/F separation) and the labeled amount of any of B and F is measured whereupon the amount of the antigen in the test solution is determined. With respect to a method for such a reaction, there are a liquid phase method in which a soluble antibody is used as the antibody and the B/F separation is conducted by polyethylene glycol, a second antibody to the above-mentioned antibody, etc.; and a solid phase method in which an immobilized antibody is used as the first antibody or a soluble antibody is used as the first antibody while an immobilized antibody is used as the second antibody.

In the immunometric method, an antigen in the test solution and an immobilized antigen are subjected to a competitive reaction with a certain amount of a labeled antibody followed by separation into solid and liquid phases or the antigen in the test solution and an excess amount of labeled antibody are allowed to react, then an immobilized antigen is added to bind an unreacted labeled antibody with the solid phase and separated into solid and liquid phases. After that, the labeled amount of any of the phases is measured to determine the antigen amount in the test solution.

In the nephrometry, the amount of insoluble sediment which is produced as a result of the antigen-antibody reaction in a gel or in a solution is measured. Even when the antigen amount in the test solution is small and only a small amount of the sediment is obtained, a laser nephrometry wherein scattering of laser is utilized can be suitably used.

In applying each of those immunological measuring methods (immunoassays) to the measuring method of the present invention, it is not necessary to set up any special condition, operation, etc. therefor. A measuring system (assay system) for the protein of the present invention may be constructed taking the technical consideration of the persons skilled in the art into consideration in the conventional conditions and operations for each of the methods. With details of those conventional technical means, a variety of reviews, reference books, etc. may be referred to.

They are, for example, Hiroshi Irie (ed): "Radioimmunoassay" (Kodansha, Japan, 1974); Hiroshi Irie (ed): "Radioimmunoassay; Second Series" (Kodansha, Japan, 1979); Eiji Ishikawa et al. (ed): "Enzyme Immunoassay" (Igaku Shoin, Japan, 1978); Eiji Ishikawa et al. (ed): "Enzyme Immunoassay" (Second Edition) (Igaku Shoin, Japan, 1982); Eiji Ishikawa et al. (ed): "Enzyme Immunoassay" (Third Edition) (Igaku Shoin, Japan, 1987); "Methods in Enzymology" Vol. 70 (Immunochemical Techniques (Part A)); ibid. Vo. 73 (Immunochemical Techniques (Part B)); ibid. Vo. 74 (Immunochemical Techniques (Part C)); ibid. Vo. 84 (Immunochemical Techniques (Part D: Selected Immunoassays)); ibid. Vol. 92 (Immunochemical Techniques (Part E: Monoclonal Antibodies and General Immunoassay Methods)); ibid. Vol. 121 (Immunochemical Techniques (Part I: Hybridoma Technology and Monoclonal Antibodies)) (Academic Press); etc.

By using the antibody of the present invention in the above manner, the protein of the present invention can be assayed with high sensitivity.

In addition, when decrease in concentration of the protein, etc. of the present invention is detected by determining the concentration of the protein, etc. of the present invention by using the antibody against the protein of the present invention, it may lead, with high probability, to the diagnosis of various diseases such as cancer, viral infection, *Helicobacter pylori* infection, invasive staphylococcia, hepatitis, nephritis, autoimmune disease, bone disease, atherosclerosis or pain and so on.

When increase in concentration of the protein, etc. of the present invention is detected, it may lead, with high probability, to the diagnosis of various diseases such as AIDS, inflammation, neurodegenerative disease due to osteomyelodysplasia, ischemic disease, destruction of joint tissues in rheumatism, hepatitis, autoimmune disease, cardiomyopathy, diabetes, diabetic complications, influenza, glomerulonephritis, uncerative colitis and so on, particulary, AIDS, inflammation, destruction of joint tissues in rheumatism, hepatitis or autoimmune disease.

Thus, the antibody of the present invention is useful as a diagnostic agent for the above-mentioned diseases.

Furthermore, the antibody of the present invention can be used for the purpose of detecting the protein of the present invention which may be present in test samples such as body fluids or tissues. The antibody can also be used for the construction of an antibody column for purification of the protein of the present invention, detection of the protein of the present invention in the fractions in the course of purification, and analysis of the behavior of the protein of the present invention in the test cell.

(4) Pharmaceutical Compositions Containing the Antibody of the Present Invention Of the antibody according to the present invention, those species which neutralize the activity of the protein, etc. of the present invention can be used as drugs, such as therapeutic or prophylactic agent for diseases such as AIDS, inflammation, neurodegenerative disease due to osteomyelodysplasia, ischemic disease, destruction of joint tissues in rheumatism, hepatitis, autoimmune disease, cardiomyopathy, diabetes, diabetic complications, influenza, glomerulonephritis, uncerative colitis and so on, particulary, AIDS, inflammation, destruction of joint tissues in rheumatism, hepatitis or autoimmune disease.

The above-mentioned therapeutic or prophylactic composition containing the antibody of the present invention can be administered either orally or otherwise to human and other mammals (e.g. rat, rabbit, sheep, swine, cattle, cat, dog, monkey), in the form of an antibody solution as such or in the form of a pharmaceutical composition having an appropriate dosage form.

The dosage is dependent on the recipient, target disease, symptom, administration route, and other factors. Generally, however, in the therapy or prevention of diabetes in a human adult, for instance, the antibody capable of neutralizing the activity of the protein, etc. of the present invention can be administered, by the intravenous route, in a single dose of about 0.01 to 20 mg/kg body weight, preferably 0.1 to 10 mg/kg body weight, or more preferably about 0.1 to 5 mg/kg body weight, about 1 to 5 times a day, or preferably about 1 to 3 times a day. For administration by other routes and for oral administration, the dosage can be selected using the above dosage schedule as a reference. In cases presenting with particularly severe symptoms, the dosage may be increased according to the condition.

The antibody of the present invention which neutralizes the activity of the protein, etc. of the present invention can be administered either as it is or in the form of a suitable pharmaceutical composition. The pharmaceutical composition comprises the antibody or its salt and a pharmaceutically acceptable carrier, diluent, or excipient. The composition can be provided in various dosage forms suited for oral administration or non-oral administration.

The composition for oral administration, for instance, includes solid and liquid dosage forms such as tablets (including dragees, film-coated tablets), pills, granules, powders, capsules (including soft capsules), syrup, emulsion, suspension, etc. Such dosage forms can be manufactured by the per se known procedures and contain a carrier, diluent or excipient which is generally included in pharmaceutical formulations. The carrier or excipient for tablets includes but is not limited to lactose, starch, sucrose, and magnesium stearate.

The composition for non-oral administration may for example an injectable product or a suppository. The injectable product includes intravenous, subcutaneous, intradermal, intramuscular, drip, and other injections. Such injections can be prepared by the per se known procedures, for example by dissolving, suspending, or emulsifying the antibody or salt in a sterile aqueous or oily vehicle which is generally used in the manufacture of injectable products. The aqueous vehicle for injections includes physiological saline and various isotonic solutions containing glucose and/or the like and may be supplemented with a suitable solubilizer such as alcohols (e.g. ethanol), polyols (e.g. propylene glycol, polyethylene glycol), nonionic surfactants [polysorbate 80, HCO-50 (polyoxyethylene (50 mol)-hydrogenated castor oil adduct)], etc. The oily vehicle includes but is not limited to sesame oil and soybean oil. Benzyl benzoate, benzyl alcohol, etc. may also be used as solubilizers. Injections thus prepared are provided as filled in suitable ampules. Suppositories for rectal administration can be manufactured by mixing said antibody or salt with any of the conventional suppository bases.

The above pharmaceutical composition for oral or non-oral administration can be conveniently provided in unit dosage forms suited for delivery of the unit dose of the active ingredient. The unit dosage form may for example be the above-mentioned tablet, pill, capsule, injection (ampule) or suppository. Preferably, the amount of said antibody or salt per unit dosage form is generally 5–500 mg and preferably 5–100 mg for injectable products or 10–250 mg for other products.

The foregoing composition may contain other active ingredients unless their formulation with said antibody or salt results in unfavorable interactions.

(5) Screening for Candidate Medicinal Compounds (A) Method for Screening a Compound Capable of Changing a Binding Activity of the Protein of the Present Invention with a Receptor to Which the Protein Can Bind The protein, etc. of the present invention is capable of binding specifically to a receptor belonging to the TNF receptor family (hereinafter referred to briefly as a receptor) and, therefore, by constructing a ligand-receptor binding assay system using the protein, etc. of the present invention and the receptor, a screening of candidate medicinal compounds having an activity equivalent to that of substances belonging to the TNF ligand family (e.g. TNF, lymphotoxin-α, lymphotoxin-β, Fas ligand, nerve growth factor, etc.) or a screening of candidate medicinal compounds which inhibit the activity of the protein, etc. of the present invention can be carried out. Thus, the present invention provides a method for screening for a compound capable of changing a binding activity of the protein of the present invention with a receptor to which the protein can bind, which comprises using the protein, etc. of the present invention.

The compound capable of changing a binding activity of the protein, etc. of the present invention with a receptor includes (i) a compound having a receptor-mediated cell stimulating activity (for example, promotion of DNA synthesis, arachidonic acid release, acetylcholine release, change in intracellular $Ca^{2+}$ concentration, intracellular cAMP production, intracellular cGMP production, inositol phosphate production, change in cell membrane potential, intracellular protein phosphorylation, activation of c-fos, pH depression, activity to stimulate or inhibit cell migration or other activity of cells, etc.), apoptosis-inducing activity, cytotoxic activity and so on (agonist), (ii) a compound having no receptor-mediated cell stimulating activity, an apotosis-inducing activity, a cytotoxic activity and so on (antagonist), (iii) a compound which increase a binding strength of the protein, etc. of the present invention and the receptor or (iv) a compound which decrease a binding strength of the protein, etc. of the present invention and the receptor. The above compound (i) may be preferably screened by the method for determining a ligand as mentioned above.

The present invention provides:

(1) A method for screening for a compound capable of changing a binding activity of the protein, etc. of the present invention with a receptor, or a salt thereof, which comprises comparing the result in cases that (i) the protein, etc. of the present invention are contacted with the receptor or its partial peptide and
(ii) the protein, etc. of the present invention and a test compound are contacted with the receptor or its partial peptide;

(2) A method for screening for a compound capable of changing a binding activity of the protein, etc. of the present invention with a receptor, or a salt thereof, which comprises comparing the result in cases that (i) the protein, etc. are contacted with cells containing a receptor or their cell membrane fractions and (ii) the protein, etc. of the present invention and a test compound are contacted with cells containing a receptor or their cell membrane fractions;

(3) A method for screening for a compound capable of changing the binding activity of the protein, etc. of the present invention with a receptor, or a salt thereof, which comprises comparing the result in cases that (i) cells containing the protein, etc. of the present invention or their cell membrane fractions are contacted with cells containing a receptor or their cell membrane fractions and (ii) cells containing the protein, etc. of the present invention or their cell membrane fractions and a test compound are contacted with cells containing a receptor or their cell membrane fractions;

Thus, those screening methods of the present invention are characterized in that a comparison is made between (i) and (ii) for the binding of the protein, etc. of the present invention to a receptor or cells containing the receptor, an apotosis-inducing activity, a cytotoxic activity, for instance.

Specifically, the present invention provides:

(1a) A method for screening for a compound capable of changing a binding activity of the protein, etc. of the present invention with a receptor, or a salt thereof, which comprises measuring and comparing an amount of binding of the labeled protein, etc. of the present invention with the receptor, its partial peptide or a salt thereof, in cases that (i) the labeled protein, etc. of the present invention are contacted with the receptor or its partial peptide and (ii) the labeled protein of the present invention and a test compound are contacted with the receptor or its partial peptide;

(2a) A method for screening for a compound capable of changing a binding activity of the protein, etc. of the present invention with a receptor, or a salt thereof, which comprises measuring and comparing an amount of binding of the labeled protein, etc. of the present invention with cells containing the receptor or their cell membrane fractions, in cases that (i) the labeled protein, etc. of the present invention are contacted with cells containing a receptor or their cell membrane fractions and (ii) the protein, etc. of the present invention and a test compound are contacted with cells containing a receptor or their cell membrane fractions;

(2b) A method for screening for a compound capable of changing a binding activity of the protein, etc. of the present invention with a receptor, or a salt thereof, which comprises measuring and comparing activities such as a receptor-mediated cell stimulating activity (for example, promotion of DNA synthesis, arachidonic acid release, acetylcholine release, change in intracellular $Ca^{2+}$ concentration, intracellular cAMP production, intracellular cGMP production, inositol phosphate production, change in cell membrane potential, intracellular protein phosphorylation, activation of c-fos, pH depression, activity to stimulate or inhibit cell migration or other activity of cells, etc.), an apotosis-inducing activity, a cytotoxic activity and so on, in cases that (i) the protein, etc. of the present invention are contacted with cells containing a receptor and (ii) the protein, etc. of the present invention and a test compound are contacted with cells containing a receptor;

(3a) A method for screening for a compound capable of changing a binding activity of the protein, etc of the present invention with a receptor, or a salt thereof, which comprises measuring and comparing activities such as a receptor-mediated cell stimulating activity (for example, promotion of DNA synthesis, arachidonic acid release, acetylcholine release, change in intracellular $Ca^{2+}$ concentration, intracellular cAMP production, intracellular cGMP production, inositol phosphate production, change in cell membrane potential, intracellular protein phosphorylation, activation of c-fos, pH depression, activity to stimulate or inhibit cell migration or other activity of cells, etc.), an apotosis-inducing activity, a cytotoxic activity and so on, in cases that (i) cells containing the protein of the present invention or their cell membrane fractions are contacted with cells containing a receptor and (ii) cells containing the protein, etc. of the present invention or their cell membrane fractions and a test compound are contacted with cells containing a receptor;

In the above-mentioned screening method (1a) or (2a), a compound found to bind the receptor to change a binding activity of the protein, etc. of the present invention with the receptor can be selected as a compound which is capable of changing the binding activity of the protein of the present invention with a receptor to which the protein can bind.

In the above screening method (2b) or (3a), a compound found to bind the receptor and exhibit the receptor-mediated cell stimulating activity (for example, promotion of DNA synthesis, arachidonic acid release, acetylcholine release, change in intracellular $Ca^{2+}$ concentration, intracellular cAMP production, intracellular cGMP production, inositol phosphate production, change in cell membrane potential, intracellular protein phosphorylation, activation of c-fos, pH depression, activity to stimulate or inhibit cell migration or other activity of cells, etc.), the apotosis-inducing activity, or the cytotoxic activity, for instance, can be selected as a receptor agonist. On the other hand, a compound which has no cell stimulating activity, apotosis-inducing activity, or other activity can be selected as a receptor antagonist.

Furthermore, in the above screening method (1a) or (2a), a compound, among the compounds shown to have an activity to change the binding activity of the protein, etc. of the present invention with the receptor, which is found to have the apotosis-inducing activity or other activity can be selected as a receptor agonist, while a compound not shown to have apotosis-inducing activity or other activity can be selected as a receptor antagonist.

The receptor used in the screening methods of the present invention includes any receptors to which the protein, etc. of the present invention can bind, such as receptors belonging to the TNF receptor family and the receptors against the protein, etc. of the present invention. Examples of the receptors belonging to the TNF receptor family are TNF receptors (55 kDa: Cell, 61, 351–359, 1990; 75 kDa, Science, 248, 1019–1023, 1990), lymphotoxin-β receptor, Fas (Cell, 66, 233–243, 1991), CD27 (The Journal of Immunology, 147, 3165–3169, 1991), CD30 (Cell, 68, 421–427, 1992), CD40 (The EMBO Journal, 8, 1403–1410, 1989), OX40 (European Journal Immunology, 24/3, 677–683, 1994), DR4 (Science, 276, 111–113, 1997), DR3/WSL-1 (NATURE, 384, 372–375, 1996; SCIENCE, 274, 990–992, 1996), TR2 (The Journal of Biological Chemistry, 272, p14272–14276, 1997).

Those receptors and the receptors against the protein, etc. of the present invention can be obtained in accordance with the per se known protein purification technology. Moreover, the receptors can also be obtained by cloning a DNA coding for the receptor in accordance with the per se known genetic engineering method and, then, producing the objective receptor by the method for expression of the protein, etc. of the present invention as described hereinbefore.

As the partial peptide of the receptor, a partial peptide available on cutting the full-length receptor appropriately can be employed.

Examples of the labeled protein, etc. of the present invention are the protein, etc. labeled with [$^3$H], [$^{125}$I], [$^{14}$C], [$^{35}$S] and so on.

Examples of the cells containing the above-mentioned receptor used in the screening method of the present invention are the same cells as those mentioned above as the host cells for expression of the protein, etc. of the present invention. Among them, CHO cells are preferred.

The receptor-containing cells can be produced by the per se known method, for example, the method for expression of the protein of the present invention as mentioned above, using a DNA coding for the receptor. Moreover, examples of the cell lines containing the receptor are established cell lines such as Jurkat cell line, U937 cell line (for both, The Journal of Biological Chemistry, 271, 12691–12694, 1996), HepG2 cell line, THP-1 cell line, etc.

Examples of the cells containing the protein of the present invention used in the screening method of the present invention are the same cell lines as those mentioned as host cells for the expression of the protein, etc. of the present invention. Among them, CHO cells are preferred. The receptor-containing cells can be prepared by the per se known method, for example the method for expression of the protein, etc. of the present, invention as described hereinbefore, by using a DNA coding for the receptor.

When cells containing the receptor or cells containing the protein, etc. of the present invention is to be used in the screening method according to the present invention, the cells can be fixed with glutaraldehyde, formaldehyde, or the like. The fixing of cells can be carried out by the per se known procedure. Moreover, as the tissue containing the protein, etc. of the present invention, livers, spleens, etc. of various animals or membrane fractions thereof can be used.

The cell membrane fractions of the cells containing the receptor or cells containing the protein, etc. of the present invention is fractions rich in cell membrane components as obtained by the disruption and subsequent treatment according to the per se known procedure. The disruption of cells can be carried out by, for example, the homogenizing technique utilizing a Potter-Elvehjem homogenizer, the disruption technique using a Warling blender or Polytron (Kinematica), sonic disruption, and the disruption method in which cells are compressed by French press or the like and simultaneously ejected from a fine nozzle. Fractionation of the cell membrane is chiefly achieved by centrifugation, e.g. by zonal centrifugation or density-gradient centrifugation. For example, the disrupted cell fluid is centrifuged at a low speed (500 rpm–3000 rpm) for a short time (usually about 1–10 minutes) and the supernatant is further centrifuged at a high speed (15000 rpm–30000 rpm) usually for 30 minutes to 2 hours, followed by recovery of the pellet for use as the membrane fraction. This membrane fraction contains not only the expressed receptor or protein, etc. of the present invention but also the membrane components such as the cell-derived phospholipids and membrane proteins.

The amount of the receptor in the receptor-containing cells or cell membrane fraction is preferably $10^3$–$10^8$ molecules per cell and more preferably $10^5$–$10^7$ molecules per cell. In this connection, the larger the amount of expression is, the higher is the ligand-binding activity per unit membrane fraction (specific activity) so that one is not only enabled to construct a highly sensitive screening system but also enabled to assay a larger number of samples per lot.

Examples of the test compound are peptides, proteins, non-peptide, compounds, synthetic compounds, fermentation products, cell extracts, plant extracts, animal tissue extracts, blood plasma and so on. Such compounds may be novel compounds or known compounds.

In the screening method of the present invention, the reaction between the protein, etc. of the present invention and the receptor is generally carried out at a temperature of about 37° C. for several hours.

Specifically, in the screening method (1a) or (2a) described hereinbefore, the cells containing the receptor or a cell membrane fraction thereof, or the receptor or its partial peptide is suspended in a buffer solution suitable for screening to prepare a receptor sample in the first place. The buffer solution may be any buffer solution that does not affect with the binding of the protein, etc. of the present invention to the receptor, thus including phosphate buffer, Tris-HCl buffer, etc. within the pH range of about 4–10 (preferably pH about 6–8). For the suppression of non-specific binding, a surfactant such as CHAPS, Tween-80™ (Kao-Atlas), digitonin, sodium deoxycholate, or the like can be added to the buffer. Furthermore, to suppress degradation of the receptor and ligand, protease inhibitors such as PMSF, leupeptin, bacitracin, aprotinin, E-64 (Institute for Protein Research), pepstatin, or the like can be added. On the other hand, when the cells are fixed cells, the coupling of the protein, etc. of the present invention with the receptor can be carried out using the cells immobilized on the incubator, that is to say the cells as grown, or the cells fixed with glutaraldehyde or paraformaldehyde.

In this case, the culture medium or Hank's solution is used as the buffer. To 0.01 ml–10 ml of the receptor solution is added the labeled protein, etc. of the present invention (e.g. [$^{125}$I]-labeled protein, etc. of the present invention) in a predetermined quantity (in the case of 2000 Ci/mmol, for instance, about 10000 cpm–1000000 cpm), and the test compound is concurrently added at a final concentration of $10^{-4}$M to $10^{-10}$M. To find the amount of non-specific binding (NSB), reaction tubes containing a large excess of the unlabeled protein, etc. of the present invention are also provided. The reaction is carried out at 0°–50° C., preferably at 4°–37° C., for 20 minutes to 24 hours, preferably 30 minutes to 3 hours. After completion of the reaction, the reaction mixture is subjected to filtration a glass fiber filter or the like and the filter is washed with a suitable amount of the same buffer. The radioactivity (e.g. the amount of [$^{125}$I]) remaining on the glass fiber filter is determined with a liquid scintillation counter or a γ-counter. For filtration, a manifold or a cell harvester can be employed but the use of a cell harvester is preferred for increased efficiency. With the balance ($B_0$–NSB) after subtracting the amount of non-specific binding (NSB) from the count ($B_0$) without an antagonist being taken as 100%, a test compound giving a specific binding (B–NSB) value of not more than 50% can be selected as a candidate agonist or antagonist compound.

In the screening method (2b) or (3a), the receptor-mediated cell stimulating activity (for example, promotion of DNA synthesis, arachidonic acid release, acetylcholine release, change in intracellular $Ca^{2+}$ concentration, intracellular cAMP production, intracellular cGMP production, inositol phosphate production, change in cell membrane potential, intracellular protein phosphorylation, activation of c-fos, pH depression, activity to stimulate or inhibit cell migration or other activity of cells, etc.), the apotosis-inducing activity, the cytotoxic activity, or other activity can be assayed by the known procedure or a procedure analogous thereto.

Specifically, the receptor-containing cells are seeded and grown on a multi-well plate or the like in the first place. Prior to screening, the medium is replaced with fresh medium or a suitable non-cytotoxic buffer and, after addition of the test compound etc., the plate is incubated for a predetermined time. Then, the cells are extracted or the supernatant is recovered and the each product is assayed by the per se known procedure. When the assay of an indicator of cell stimulating activity (e.g. arachidonic acid) is confounded by a proteolytic enzyme contained in the cells, an inhibitor of the enzyme can be added prior to the assay. As to activity to suppress cAMP production, for instance, the activity can be assayed as production inhibitory activity against cells with basal production enhanced by forskolin or the like beforehand.

The term "apotosis" is used referring to cell shrinkage, chromatin condensation, nuclear condensation, disappearance of microvilli, blebbing, formation of apoptotic small bodies, gaps from surrounding cells owing to cell shrinkage, and phagocytic scavenging by the adjacent cells (Japanese Journal of Clinical Medicine, 54, No. 7, 1996).

Apotosis-inducing activity can be assayed by the morphological analysis or biochemical analysis of apotosis in accordance with, for example Apotosis Experimental Protocol (Dec. 20, 1994) in Experimental Protocol Series (Supplement), Saibo Kogaku (Cell Engineering), Shujunsha. The method for morphological analysis includes light-microscopic observation of apotosis (e.g. observation of cell morphology by phase-contrast microscope, observation of dye-stained floating or adherent cells, observation by fluorescein staining, etc. and morphological observation of tissues involving the use of paraffin sections, hematoxylin/eosin-stained specimens, etc.) and electron-microscopic observation of apotosis (e.g. ultrathin-section preparation and electron staining). The biochemical analysis of apotosis includes DNA fragmentation analysis (e.g. agarose gel electrophoresis), and cell death assessment methods (e.g. crystal violet method, MTT method, LDH method, etc.).

The assay of cytotoxic activity can be performed in accordance with the method of Rouvier E. et al., Journal of Experimental Medicine, 177, 195–200, 1993.

In the above screening method (2b) or (3a), when apotosis or cytotoxic responses in the receptor-containing cells is induced by addition of a test compound, the test compound can be selected as a candidate receptor agonist compound. On the other hand, when an apotosis or a cytotoxic activity is inhibited by addition of a test compound, the test compound can be selected as a candidate receptor antagonist compound.

The screening kit according to the present invention comprises the protein of the present invention and, preferably, receptor-containing cells or a cell membrane fraction thereof.

The following is an example of the screening kit of the present invention.

Screening Reagents (1) Assay Buffer and Wash Buffer

Hank's balanced salt solution (Gibco BRL) supplemented with 0.05% bovine serum albumin (Sigma)

Sterilized with a 0.45 μm filter and stored at 4° C., or optionally prepared before use (2) A Receptor Sample CHO cells containing the receptor against the protein of the present invention or a TNF receptor, etc. are subcultured in a 12-well plate, 5×10$^5$ cells/well, and incubated at 37° C. under 5% $CO_2$–95% air for 2 days.

(3) A Labeled Sample of the Protein of the Present Invention

The protein of the present invention, its partial peptide or a salt thereof, as labeled with [$^3$H], [$^{125}$I], [$^{14}$C] or [$^{35}$S].

(4) A Standard Solution of the Protein, etc. of the Present Invention

The protein of the present invention, its partial peptide thereof or a salt thereof, as dissolved in 0.1% bovine serum albumin (Sigma)-PBS at a final concentration of 0.1 mM and stored at −20° C.

Method for Assay (1) Culture CHO cells containing a recombinant receptor in a 12-well tissue culture plate, wash twice with 1 ml of assay buffer, and add 490 μl of assay buffer to each well.

(2) Add 5 μl of a 10$^{-3}$ to 10$^{-10}$M solution of a test compound and, then, 5 μl of 5 nM labeled protein, etc. of the present invention, and react at room temperature for 1 hour. To find the amount of non-specific binding, add 5 μl of 10$^{-4}$M protein, etc. of the present invention in stead of the test compound.

(3) Discard the reaction fluid and wash 3 times with 1 ml of wash buffer. Dissolve the labeled protein, etc. of the present invention as conjugated to the cells with 0.5 ml of 0.2 N NaOH-1% SDS and mix the solution with 4 ml of liquid scintillator A (Wako Pure Chemical).

(4) Measure radioactivity with a liquid scintillation counter (Beckmann) and calculate the percent maximum binding (PMB) by means of the following equation. In case [$^{125}$I] has been used for labeling, direct counting with a gamma-counter can be made without mixing with a liquid scintillator.

$$PMB=[(B-NSB)/(B-NSB)]\times 100$$

PMB: percent maximum binding
B: value with addition of test sample
NSB: non-specific binding
$B_0$: maximum binding Thus, the protein, etc. of the present invention is useful as a reagent for the screening of a compound capable of the binding activity of the protein, etc. of the present invention with the receptor.

The compound or a salt thereof, which can be useful by the screening method of the present invention or by using the screening kit of the present invention is a compound which changes the binding activity of the protein, etc. of the present invention with a receptor. The compound includes (i) a compound which has a receptor-mediated cell stimulating activity, an apotosis-inducing activity or a cytotoxic activity (receptor agonist), (ii) a compound which does not have any of the cell stimulating activity, apotosis-inducing activity, or cytotoxic activity (receptor antagonist), (iii) a compound which increase a binding activity of the protein, etc. of the present invention and the receptor or (iv) a compound which decrease the binding activity of the protein, etc. of the present invention and the receptor.

The compound can be obtained from the test compounds as mentioned above, and may be any one of peptides, proteins, non-peptideous compounds, synthetic compounds, fermentation products, cell extracts, plant extracts, animal tissue extracts or blood plasma. The such compounds may be novel or know compounds.

The receptor agonist has all or some of the physiological activities possessed by the protein, etc. of the present invention and is useful as a safe or low-toxicity drug for uses relevant to the physiological activities. For example, it is useful as a therapeutic or prophylactic agent for cancer (e.g. breast cancer, prostate cancer, ovary cancer, follicular lymphoma, cancer associated with p53 mutation, brain tumor, bladder cancer, uterocervical cancer, colon cancer (colorectal cancer), non-small cell carcinoma of lung, small cell carcinoma of lung, stomach cancer, etc.), viral or bacterial infection (e.g. initial phase of AIDS virus infection, herpes virus infection, adenovirus infection, poxvirus infection, varicella-zoster virus infection, human papillomavirus infection, etc.), *Helicobacter pylori* infection, invasive staphylococcia, hepatitis (e.g. hepatitis A, hepatitis C, etc.), nephritis, autoimmune disease (e.g. systemic lupus erythematosus, immune complex glomerulonephritis, etc.), bone disease (e.g. rheumatoid arthritis (e.g. abnormal proliferation of synuvial cells in rheumatism) etc.), atherosclerosis, and pain, preferably cancer (e.g. breast cancer, prostate cancer, ovary cancer, follicular lymphoma, cancer associated with p53 mutation, etc.), viral or bacterial infection (e.g. incipient stage of AIDS virus infection, herpes virus infection, adenovirus infection, poxvirus infection, etc.), hepatitis, nephritis, rheumatoid arthritis, atherosclerosis, autoimmune diseases (e.g. systemic lupus erythematosus, immune complex glomerulonephritis, etc.).

The receptor antagonist inhibits all or some of the physiological activities possessed by the protein, etc. of the present invention and are useful as a safe or low-toxicity drug for inhibiting those physiological activities. Therefore, it is useful for example, as a therapeutic or prophylactic agent for AIDS, inflammation, neurodegenerative disease (e.g. Alzheimer's disease, Parkinson's disease, amyotrophic lateral sclerosis, pigmentary retinitis, cerebellar degeneration, etc.), diseases due to osteomyelodisplasia (e.g. aplastic anemia etc.), ischemic disease (e.g. myocardial infarction, stroke, etc.), destruction of joint tissues in rheumatism, hepatitis (e.g. fulminant hepatitis), autoimmune disease (e.g. systematic lupus erythematosus, immune complex glomerulonephritis, etc.), cardiomyopathy (e.g. dilated cardiomyopathy), diabetes, diabetic complications (e.g. diabetic nephropathy, diabetic neuropathy, diabetic retinopathy), influenza, glomerulonephritis, and ulcerative colitis, preferably AIDS, inflammation, destruction of joint tissues in rheumatism, hepatitis (e.g. fulminant hepatitis), and autoimmune disease (e.g. systematic lupus erythematosus, immune complex glomerulonephritis, etc.).

The compound which increases the binding activity of the protein, etc. of the present invention and the receptor in useful as a safe or low-toxicity drug for increasing the physiological activities of the protein, etc. of the present invention. Therefore, the compound is useful as a therapeutic or prophylactic agent for cancer, viral infection, *Helicobacter pylori* infection, invasive staphylococcia, hepatitis, nephritis, autoimmune disease, bone disease, atherosclerosis or pain, as same as the agonist as mentioned above.

The compound which decreases the binding activity of the protein, etc. of the present invention and the receptor in useful as a safe or low-toxicity drug for decreasing the physiological activities of the protein, etc. of the present invention. Therefore, the compound is useful as a therapeutic or prophylactic agent for AIDS, inflammation, neurodegenerative disease due to osteomyelodysplasia, ischemic disease, destruction of joint tissues in rheumatism, hepatitis, autoimmune disease, cardiomyopathy, diabetes, diabetic complications, influenza, glomerulonephritis or uncerative colitis, as same as the antagonist as mentioned above.

The salts of the compound obtained by the screening method as mentioned above include salts with physiologically acceptable bases (e.g. alkali metals) or acids such as organic or inorganic acids, and are preferably a physiologically acceptable acid addition salt. Examples of such salts are salts thereof with inorganic acids (e.g. hydrochloric acid, phisphoric acid, hydrobromic acid or sulfuric acid, etc.) and salts thereof with organic acids (e.g. acetic acid, formic acid, propionic acid, fumaric acid, maleic acid, succinic acid, tartaric acid, citric acid, malic acid, oxalic acid, benzoic acid, methanesulfonic acid or benzenesulfonic acid, etc.).

Because the thus-obtained preparation is safe and of low toxicity, it can be administered to humans or mammals (e.g., rat, mouse, guinia pig, rabbit, sheep, pig, bovine, horse, cat, dog, monkey, etc.).

The dose of the compound obtained by the screening method may vary depending on subject disease, subject of administration, way of administration, and so on. When the agonist is used, for example, for treating cancer by oral administration, the dose of the agonist is normally about 0.1 to 100 mg, preferably 1.0 to 50 mg, and more preferably 1.0 to 20 mg per day for an adult (weighing 60 kg). When the agonist is used, for example, for treating cancer by non-oral administration, it is advantageous to administer the agonist in the form of injectable preparation at a daily dose of about 0.01 to 30 mg, preferably about 0.1 to 20 mg, and more preferably about 0.1 to 10 mg per administration by an intravenous injection for an adult (weighing 60 kg), depending on subject of administration, subject disease and so on. For other animal species, corresponding does as converted per 60 kg weight can be administered. When the antagonist is used, for example, for treating AIDS by oral administration, the dose of the antagonist is normally about 0.1 to 100 mg, preferably 1.0 to 50 mg, and more preferably 1.0 to 20 mg per day for an adult (weighing 60 kg). When the antagonist is used, for example, for treating AIDS by non-oral administration, it is advantageous to administer the antagonist in the form of injectable preparation at a daily dose of about 0.01 to 30 mg, preferably about 0.1 to 20 mg, and more preferably about 0.1 to 10 mg per administration by an intravenous injection for an adult (weighing 60 kg), depending on subject of administration, subject disease and so on. For other animal species, corresponding does as converted per 60 kg weight can be administered.

(B) The Screening Method and Screening Kit for a Compound Which Promotes or Inhibits an Activity of a Proteinase Which Converts the Protein of the Present Invention The protein of the present invention, as well as its salt, is a membrane-binding protein, and is considered to express its functions (i) as the protein bounds to the membrane or (ii) as the extracellular domain is released by the cleavage of the binding domain by endogenous proteinase and the extracellular domain binds the receptor. Therefore, by using the protein etc. of the present invention and a proteinase having an activity to convert the protein of the present invention, a compound having an activity to promote or inhibit the activity of the proteinase having an activity of degrading the protein of the present invention can be selected.

The compound having an activity to inhibit the activity of the proteinase inhibits a release of the extracellular domain of the protein, etc. of the present invention in vivo to thereby inhibit the activity not dependent on cell-to-cell contact of the protein, etc. of the present invention. Therefore, the compound can be useful as a pharmaceutical agent such as a therapeutic or prophylactic agent for destruction of joint tissues in rheumatism, hepatitis, or autoimmune disease (e.g. systemic lupus erythematosus, immune complex glomerulonephritis, etc.), among other diseases.

Thus, the present invention provides a method for screening for a compound, or a salt thereof, having an activity to promote or inhibit the activity of the proteinase having an activity of degrading the protein of the present invention, which comprises using the protein, etc. of the present invention.

More specifically, the present invention provides:
(1) A method for screening for a compound, or a salt thereof, having an activity to promote or inhibit a proteinase having an activity of converting the protein of the present invention, which comprises a result in cases that (i) a culture supernatant obtained by culture of cells containing the protein of the present invention in the presence of the proteinase (provided, however, that where the cells containing the protein of the present invention produce and secrete an extracellular proteinase having an activity to convert the protein of the present invention, it may be the extracellular proteinase which the cells produce and secrete) with cells containing a receptor and (ii) a culture supernatant obtained by culture of the cells containing the protein of the present invention in the presence of the proteinase and a test compound with the cells containing the receptor.

Specifically, in the screening method of the present invention, a comparison is made between (i) and (ii), for example, a receptor-mediated cell stimulating activity, an apotosis-inducing activity or a cytotoxic activity in the receptor-containing cells.

More specifically, the present invention provides:

(1a) A method for screening for a compound, or a salt hereof, having an activity to promote or inhibit the activity of the proteinase, which comprises measuring and comparing activities such as a receptor-mediated cell stimulating activity (for example, promotion of DNA synthesis, arachidonic acid release, acetylcholine release, change in intracellular $Ca^{2+}$ concentration, intracellular cAMP production, intracellular cGMP production, inositol phosphate production, change in cell membrane potential, intracellular protein phosphorylation, activation of c-fos, pH depression, activity to stimulate or inhibit cell migration or other activity of cells, etc.), an apotosis-inducing activity or a cytotoxic activity, in cases that (i) a culture supernatant obtained by culture of a cells containing the protein of the present invention in the presence of the proteinase (provided, however, that where the cells containing the protein of the present invention produce and secrete an extracellular proteinase having an activity to convert the protein of the present invention, it may be the extracellular proteinase which the cells produce and secrete) with cells containing a receptor and (ii) a culture supernatant obtained by culture of the cells containing the protein of the present invention in the presence of the proteinase and a test compound with the cells containing the receptor.

By the above screening method, the test compound which inhibits the activity such as a receptor-mediated cell stimulating activity (for example, promotion of DNA synthesis, arachidonic acid release, acetylcholine release, change in intracellular $Ca^{2+}$ concentration, intracellular cAMP production, intracellular cGMP production, inositol phosphate production, change in cell membrane potential, intracellular protein phosphorylation, activation of c-fos, pH depression, activity to stimulate or inhibit cell migration or other activity of cells, etc.), an apotosis-inducing activity, a cytotoxic activity, etc. can be selected as a compound or a salt thereof having an activity to inhibit the proteinase having an activity of converting the protein of the present invention.

The receptor used in the screening method of the present invention includes any receptors to which the protein, etc. of the present invention can bind such as a receptor belonging to the TNF receptor family and the receptor against the protein of the present invention. The receptor belonging to the TNF receptor family includes but is not limited to TNF receptor (55 kDa or 75 kDa), lymphotoxin-β receptor, Fas, CD27, CD30, CD40, OX40, DR4, DR3/WSL-1 and TR2 mentioned hereinbefore.

Those receptors and the receptor against the protein, etc. of the present invention can be prepared by the per se known protein purification technology. The objective receptor can also be prepared by cloning a DNA coding for the receptor by the per se known genetic engineering technology and, using the DNA clone, applying the method for expression of the protein, etc. of the present invention as described hereinbefore.

Examples of the proteinase having an activity of converting the protein of the present invention are a matrix metalloproteinase such as MMP-1, MMP-2 or MMP-3, adamalysins (ADAMs) such as TNF-α-converting enzyme (TACE), and so on.

Examples of the cells containing the receptor used in the screening method of the present invention are the same cells as those mentioned hereinbefore as the host cells for expression of the protein, etc. of the present invention. Among them, CHO cells are preferred. The receptor-containing cells can be prepared by the per se known method, for example, by the method for the expression of the protein, etc. of the present invention as described hereinbefore, by using a DNA coding for the receptor. Moreover, examples of the cells containing the receptor are established cell lines such as Jurkat cell line, U937 cell line, HepG2 cell line, THP-1 cell line, etc.

Examples of the cells containing the protein of the present invention used in the screening method of the present invention, are the same cells as those mentioned as the host cells for the expression of the protein, etc. of the present invention. Among them, CHO cells are preferred. The receptor-containing cells can be prepared by the per se known technology, for example, the method for the expression of the protein, etc. of the present invention as described hereinbefore, using a DNA coding for the receptor.

When cells containing the protein, etc. of the present invention is used in the screening method according to the present invention, the cells can be fixed with glutaraldehyde, formaldehyde, or the like. The fixing of cells can be carried out by the per se known method. Moreover, as the tissue containing the protein of the present invention, livers, spleens, etc. of various animals or the membrane fractions thereof can be used.

The cell membrane fractions of cells containing the protein, etc. of the present invention include the same cell membrane fractions as described hereinbefore.

The test compound includes peptides; proteins, non-peptide compounds, synthetic compounds, fermentation products, cell extracts, plant extracts, animal tissue extracts, blood plasma and so on. These compounds may be novel or known compounds.

In the screening method of the present invention, culture of cells containing the protein, etc. of the present invention in the presence of the proteinase is generally carried out at about 37° C. for several hours. The reaction between the resulting culture supernatant and the receptor-containing cells is generally carried out at about 37° C. for several hours.

The assay of the receptor-mediated cell stimulating activity, apotosis-inducing activity or cytotoxic activity can be carried out in the same manner as described hereinbefore.

The screening kit of the present invention comprises the protein, etc. of the present invention., a proteinase having an activity to convert the protein of the present invention, and preferably a receptor-containing cell line.

The following is an example of the screening kit of the present invention.

Screening Reagents (1) Assay buffer and wash buffer

Hank's balanced salt solution (Gibco BRL) supplemented with 0.05% bovine serum albumin (Sigma)

Sterilized with a 0.45 μm filter and stored at 4° C., or optionally prepared before use (2) A receptor sample CHO cells containing the receptor against the protein, etc. of the present invention or a TNF receptor are subcultured in a 12-well plate, $5 \times 10^5$ cells/well, and incubated at 37° C. under 5% $CO_2$-95% air for 2 days.

(3) A sample of the protein of the present invention

Cells containing the protein of the present invention (4) A sample of the proteinase having an activity to convert the protein of the present invention Matrix metalloproteinase (this is not necessary when cells containing the protein of the present invention produce or secrete an extracellular proteinase having an activity to convert the protein of the present invention).

Assay Protocol (1) Incubate cells containing the protein or equivalent of the present invention in the presence of a proteinase having an activity to convert the protein of the present invention (provided, however, that where the cells containing the protein of the present invention produce and secrete an extracellular proteinase having an activity to convert the protein of the present invention, it may be extracellular proteinase which the cells produce and secrete) at about 37° C. for several hours to prepare a culture supernatant.

(2) Incubate the cells containing the protein of the present invention in the presence of the proteinase and a test compound at about 37° C. for several hours to prepare a culture supernatant.

(3) Incubate each of the culture supernatants obtained under (1) and (2), respectively, and cells containing the receptor against the protein of the present invention together at about 37° C. for several hours.

(4) Then, assay apotosis-inducing activity in accordance with the method described in Apotosis Experimental Protocol (published Dec. 20, 1994), Experimental Protocol Series (Supplement), Saibo Kogaku (Cell Engineering), Shujunsha.

Thus, the protein, etc. of the present invention is useful as a reagent for the screening for a compound, or a salt thereof, having an activity to promote or inhibit the activity of the proteinase having an activity to convert the protein of the present invention.

The salts of the compound as obtained by the screening method as mentioned above includes salts with physiologically acceptable bases (e.g. alkali metals) or acids such as organic or inorganic acids, and is preferably a physiologically acceptable acid addition salt. Examples of such salts are salts thereof with inorganic acids (e.g. hydrochloric acid, phisphoric acid, hydrobromic acid or sulfuric acid, etc.) and salts thereof with organic acids (e.g. acetic acid, formic acid, propionic acid, fumaric acid, maleic acid, succinic acid, tartaric acid, citric acid, malic acid, oxalic acid, benzoic acid, methanesulfonic acid or benzenesulfonic acid, etc.)

The compound, or a salt thereof, which promotes activity of the the proteinase having an activity to convert the protein of the present invention, obtained by the screening method of the present invention or by using the screening kit of the present invention can promote the release of the extracellular domain of the protein of the present invention by the proteinase, and can promote the activities mediated by the receptor against the protein of the present invention which are not dependent on cell-to-cell contact, such as a cell stimulating activity, apotosis-inducing activity, cytotoxic activity, etc. Therefore, the compound is useful as a safe, low-toxicity drug such as a prophylactic or therapeutic composition for diseases such as cancer, viral infection, *Helicobacter pylori* infection, invasive staphylococcia, hepatitis, nephritis, autoimmune disease, bone disease, atherosclerosis or pain.

On the other hand, the compound, or a salt thereof, which inhibits the activity of the proteinase having an activity to convert the protein of the present invention, obtained by the screening method of the present invention or by using the screening kit of the present invention can inhibit the release of the extracellular domain of the protein of the present invention by the proteinase, and can suppress the activities mediated by the receptor against the protein of the present invention which are not dependent on cell-to-cell contact, such as a cell stimulating activity, apotosis-inducing activity, cytotoxic activity, etc. Therefore, the compound is useful as a safe, low-toxicity drug such as a prophylactic or therapeutic composition for diseases such as AIDS, inflammation, neurodegenerative disease (e.g. Alzheimer's disease, Parkinson's disease, amyotrophic lateral sclerosis, pigmentary retinitis, cerebellar degeneration, etc.), diseases due to osteomyelodisplasia (e.g. aplastic anemia etc.), ischemic disease (e.g. myocardial infarction, stroke, etc.), destruction of joint tissues in rheumatism, hepatitis (e.g. fulminant hepatitis), autoimmune disease (e.g. systematic lupus erythematosus, immune complex glomerulonephritis, etc.), cardiomyopathy (e.g. dilated cardiomyopathy), diabetes, diabetic complications (e.g. diabetic nephropathy, diabetic neuropathy, diabetic retinopathy), influenza, glomerulonephritis, and ulcerative colitis, preferably AIDS, inflammation, destruction of joint tissues in rheumatism, hepatitis (e.g. fulminant hepatitis), and autoimmune disease (e.g. systematic lupus erythematosus, immune complex glomerulonephritis, etc.).

When the compound obtained by the screening method of the present invention or by using the screening kit of the present invention is used as the therapeutic or prophylactic composition, it can be formulated to tablets, capsules, elixirs, microcapsules, aspetic solution, suspensions or the like in the same way as the pharmaceutical composition comprising the protein, etc. of the present invention as mentioned above.

Because the thus-obtained preparation is safe and of low toxicity, it can be administered to humans or mammals (e.g., rat, mouse, guinia pig, rabbit, sheep, pig, bovine, horse, cat, dog, monkey, etc.).

The dose of the compound may vary depending on subject disease, subject of administration, way of administration, and so on. When the compound, which can promote the activity of the proteinase having the activity to convert the protein of the present invention, is used, for example, for treating cancer by oral administration, the dose of the compound is normally about 0.1 to 100 mg, preferably 1.0 to 50 mg, and more preferably 1.0 to 20 mg per day for an adult (weighing 60 kg). When the compound is used, for example, for treating cancer by non-oral administration, it is advantageous to administer the compound in the form of injectable preparation at a daily dose of about 0.01 to 30 mg, preferably about 0.1 to 20 mg, and more preferably about 0.1 to 10 mg per administration by an intravenous injection for an adult (weighing 60 kg), depending on subject of administration, subject disease and so on. For other animal species, corresponding does as converted per 60 kg weight can be administered.

On the other hand, when the compound, which can inhibit the activity of the proteinase having the activity to convert the protein of the present invention, is used, for example, for treating autoimmune disease by oral administration, the dose of the compound is normally about 0.1 to 100 mg, preferably 1.0 to 50 mg, and more preferably 1.0 to 20 mg per day for an adult (weighing 60 kg). When the compound is used, for example, for treating autoimmune disease by non-oral administration, it is advantageous to administer the compound in the form of injectable preparation at a daily dose of about 0.01 to 30 mg, preferably about 0.1 to 20 mg, and more preferably about 0.1 to 10 mg per administration by an intravenous injection for an adult (weighing 60 kg), depending on subject of administration, subject disease and so on. For other animal species, corresponding does as converted per 60 kg weight can be administered.

(C) The Screening Method for a Compound or a Salt Thereof Which Promotes or Inhibits an Intracellular Signal Transduction Following the Binding of the Protein, etc. of the Present Invention to the Receptor The protein, etc. of the present invention specifically binds receptors of the TNF receptor family (hereinafter referred to briefly as the receptor) or the receptor against the protein, etc. of the present invention and, therefore, by constructing a ligand-receptor binding assay system using the protein, etc. of the present invention and such a receptor, the screening of a compound or a salt thereof having an activity to promote or inhibit an intracellular signal transduction following the binding of the protein, etc. of the present invention to the receptor can be carried out.

Thus, the present invention provides a screening method for a compound, or a salt thereof, which promotes or inhibits intracellular signal transduction following the binding of the protein, etc. of the present invention to the receptor, which comprises using the protein or equivalent of the present invention as a reagent.

More specifically, the present invention provides (1) A method for screening for a compound, or a salt thereof, which promotes or inhibits an intracellular signal transduction following the binding of the protein, etc. of the present invention to the receptor, which comprises comparing the result, in cases that (i) cells containing the receptor are contacted with the protein, etc. of the present invention and (ii) the cells containing the receptor are contacted with the protein, etc. of the present invention and a test compound, and (2) A method for screening for a compound, or a salt thereof, which promotes or inhibits an intracellular signal transduction following the binding of the protein, etc. of the present invention to the receptor, which comprises comparing the result, in cases that (i) cells containing the receptor are contacted with cells containing the protein, etc. of the present invention or their cell membrane fractions and (ii) the cells containing the receptor are contacted with cells containing the protein, etc. of the present invention or their cell membrane fractions and a test compound.

Specifically, in the screening method of the present invention, a comparison is made between (i) and (ii) for e.g. an intracellular signal transduction following the binding of the protein, etc. of the present invention to the receptor.

More specifically, the present invention provides:

(1a) A method for screening for a compound, or a salt thereof, which promotes or inhibits an intracellular signal transduction following the binding of the protein, etc. of the present invention to the receptor, which comprises measuring and comparing a receptor-mediated cell stimulating activity (for example, promotion of DNA synthesis, arachidonic acid release, acetylcholine release, change in intracellular $Ca^{2+}$ concentration, intracellular cAMP production, intracellular cGMP production, inositol phosphate production, change in cell membrane potential, intracellular protein phosphorylation, activation of c-fos, pH depression, activity to stimulate or inhibit cell migration or other activity of cells, etc.), an apotosis-inducing activity or a cytotoxic activity, in cases that (i) the protein, etc. of the present invention are contacted with cells containing the receptor and (ii) the protein, etc. of the present invention and a test compound are contacted with the cells containing the receptor, (2a) A method for screening for a compound, or a salt thereof, which promotes or inhibits an intracellular signal transduction following the binding of the protein, etc. of the present invention to the receptor, which comprises measuring and comparing a receptor-mediated cell stimulating activity (for example, promotion of DNA synthesis, arachidonic acid release, acetylcholine release, change in intracellular $Ca^{2+}$ concentration, intracellular cAMP production, intracellular cGMP production, inositol phosphate production, change in cell membrane potential, intracellular protein phosphorylation, activation of c-fos, pH depression, activity to stimulate or inhibit cell migration or other activity of cells, etc.), an apotosis-inducing activity or a cytotoxic activity in cases that (i) cells containing the protein, etc. of the present invention or their cell membrane fractions are contacted with cells containing the receptor and (ii) cells containing the protein, etc. of the present invention or their cell membrane fractions and a test compound are contacted with cells containing the receptor.

In the above screening method (1a) or (2a), any compound that does not affect with the binding of the protein, etc. of the present invention to the receptor but rather promotes the receptor-mediated cell stimulating activity, apotosis-inducing activity or cytotoxic activity can be selected as the compound, or a salt thereof, which promotes an intracellular signal transduction following the binding of the protein, etc. of the present invention to the receptor. On the other hand, any compound that does not affect with the binding of the protein, etc. of the present invention to the receptor and inhibits the cell stimulating activity, apotosis-inducing activity or the like can be selected as the compound or a salt thereof which inhibits an intracellular signal transduction following the binding of the protein, etc. of the present invention to the receptor.

Since this screening method is a method for selecting a compound which does not affect with the binding of the protein, etc. of the present invention to the receptor but modulates (either promotes or suppresses) an intracellular signal transduction following receptor binding, the test compound used in this screening method is preferably a compound which is not selected as a receptor agonist or antagonist in the above-mentioned screening method for a receptor agonist or antagonist.

Examples of the receptor used in the screening method of the present invention are any receptors which the protein, etc. of the present invention can bind such as receptors belonging to the TNF receptor family, the receptor against the protein, etc. of the present invention and so on. As such receptors of the TNF receptor family, the above-mentioned TNF receptor (55 kDa or 75 kDa), lymphotoxin-β receptor, Fas, CD27, CD30, CD40, and OX40, among other factors, can be employed.

Those receptors and the receptor of the protein, etc. of the present invention can be prepared by the per se known protein purification technology. The objective receptor can be also prepared by cloning a DNA coding for the receptor by the per se known genetic engineering technology and applying the method for the expression of the protein, etc. of the present invention as described hereinbefore.

As the partial peptide of this receptor, a partial peptide obtained by cutting the full-length receptor appropriately can be employed.

The cells containing the receptor used in the screening method of the present invention includes those mentioned hereinbefore for the host cells for the expression of the protein, etc. of the present invention. Among them, CHO cells are particularly preferred. Such receptor-harboring cells can be prepared by the per se known technology, for example, the method for the expression of the protein, etc. of the present invention, by using a DNA coding for the receptor. Moreover, examples of the cells containing the receptor are established cell lines such as Jurkat cell line, U937 cell line, HepG2 cell line, THP-1 cell line, etc.

The cells containing the protein, etc. of the present invention used in the screening method of the present invention include those mentioned hereinbefore for the host cells for the expression of the protein, etc. of the present invention. Among them, CHO cells are particularly preferred. Such receptor-containing cells can be prepared by the per se known technology, for example the method for the expression of the protein, etc. of the present invention, by using a DNA coding for the receptor.

When cells containing the receptor or cells containing the protein, etc. of the present invention are used in the screening method of the present invention, the cells may be fixed with glutaraldehyde, formaldehyde, or the like. This fixing can be carried out in accordance with the per se known procedure. Moreover, as the tissue containing the protein, etc. of the present invention, livers, spleens, etc. of various animals and their membrane fractions can be used.

As the tissue containing the receptor or the membrane fraction of cells containing the protein, etc. of the present invention, those mentioned hereinbefore can be employed.

The test compound used includes peptides, proteins, non-peptideous compounds, synthetic compounds, fermentation products, cell extracts, plant extracts, animal tissue extracts, blood plasma, etc. The compound may be novel or known compounds.

In the screening method of the present invention, the reaction between the protein, etc. of the present invention and cells containing the receptor can be carried out generally at about 37° C. for several hours.

In the above screening method (1a) or (2a), the assay of a cell stimulating activity, apotosis-inducing activity or cytotoxic activity can be carried out in the same manner as described hereinbefore.

When, in the above screening method (1a) or (2a), the receptor-mediated cell stimulating activity, apotosis-inducing activity, cytotoxic activity, etc. are enhanced by addition of a test compound, the test compound can be selected as a compound or a salt thereof that promotes an intracellular signal transduction following the binding of the protein, etc. of the present invention to the receptor. On the other hand, when the receptor-mediated cell stimulating activity, apotosis-inducing activity, cytotoxic activity, etc. are inhibited by addition of a test compound, the test compound can be selected as a compound that inhibits an intracellular signal transduction following the binding of the protein, etc. of the present invention to the receptor.

The screening kit of the present invention comprises the protein, etc. of the present invention and preferably cells containing a receptor.

The following is an example of the screening kit of the present invention.

Screening Reagents (1) Assay buffer and wash buffer

Hank's balanced salt solution (Gibco BRL) supplemented with 0.05% bovine serum albumin (Sigma)

Sterilized with a 0.45 μm filter and stored at 4° C., or optionally prepared before use (2) A receptor sample CHO cells containing the receptor against the protein of the present invention or a TNF receptor are subcultured in a 12-well plate, $5 \times 10^5$ cells/well, and incubated at 37° C. under 5% $CO_2$-95% air for 2 days.

(3) A sample of the protein, etc. of the present invention

The protein, etc. of the present invention, its partial peptide or a salt thereof.

Assay Protocol

Apotosis-inducing activity can be assayed in accordance with Apotosis Experimental Protocol (Dec. 20, 1994), Experimental Protocol Series (Supplement), Saibo Kogaku (Cell Engineering), Shujunsha.

Thus, the protein, etc. of the present invention is useful as a reagent for the screening for a compound or a salt thereof that promotes or inhibits an intracellular signal transduction following the binding of the protein, etc. of the present invention to the receptor.

The salts of the compound obtained by the screening method as mentioned above include salts with physiologically acceptable bases (e.g. alkali metals) or acids such as organic or inorganic acids, and are preferably a physiologically acceptable acid addition salt. Examples of such salts are salts thereof with inorganic acids (e.g. hydrochloric acid, phisphoric acid, hydrobromic acid or sulfuric acid, etc.) and salts thereof with organic acids (e.g. acetic acid, formic acid, propionic acid, fumaric acid, maleic acid, succinic acid, tartaric acid, citric acid, malic acid, oxalic acid, benzoic acid, methanesulfonic acid or benzenesulfonic acid, etc.)

The compound or a salt thereof obtained by the screening method of the present invention or by using the screening kit of the present invention is a compound, or a salt thereof, that promotes an intracellular signal transduction such as a receptor-mediated cell stimulating activity, apotosis-inducing activity, cytotoxic activity, etc., following the binding or a compound, or a salt thereof, that inhibits the cell stimulating, apotosis-inducing, cytotoxic, activity, etc.

The compound, or a salt thereof, that promotes an intracellular signal transduction following the binding of the protein, etc. of the present invention to the receptor is useful as a safe, low-toxicity drug, for example, as a prophylactic or therapeutic agent for various diseases such as cancer (e.g. breast cancer, prostate cancer, ovary cancer, follicular lymphoma, cancer associated with p53 mutation, brain tumor, bladder cancer, uterocervical cancer, colon cancer (colorectal cancer), non-small cell carcinoma of lung, small cell carcinoma of lung, stomach cancer, etc.), viral or bacterial infection (e.g. initial phase of AIDS virus infection, herpes virus infection, adenovirus infection, poxvirus infection, varicella-zoster virus infection, human papillomavirus infection, etc.), *Helicobacter pylori* infection, invasive staphylococcia, hepatitis (e.g. hepatitis A, hepatitis C, etc.), nephritis, autoimmune disease (e.g. systemic lupus erythematosus, immune complex glomerulonephritis, etc.), bone disease (e.g. rheumatoid arthritis such as joint tissue destrution in rheumatism, etc.), atherosclerosis, and pain, preferably cancer (e.g. breast cancer, prostate cancer, ovary cancer, follicular lymphoma, cancer associated with p53 mutation, etc.), viral or bacterial infection (e.g. incipient stage of AIDS virus infection, herpes virus infection, adenovirus infection, poxvirus infection, etc.), hepatitis, nephritis, rheumatoid arthritis, atherosclerosis, and autoimmune disease (e.g. systemic lupus erythematosus, immune complex glomerulonephritis, etc.).

The compound, or a salt thereof, that inhibits an intracellular signal transduction following the binding of the protein, etc. of the present invention to the receptor is useful as a safe, low-toxicity drug, for example a therapeutic or prophylactic agent for various diseases such as AIDS, inflammation, neurodegenerative disease (e.g. Alzheimer's disease, Parkinson's disease, amyotrophic lateral sclerosis, pigmentary retinitis, cerebellar degeneration, etc.), diseases due to osteomyelodysplasia (e.g. aplastic anemia etc.), ischemic disease (e.g. myocardial infarction, stroke, etc.), joint tissue destruction in rheumatism, hepatitis (e.g. fulminant hepatitis), autoimmune disease (e.g. systematic lupus erythematosus, immune complex glomerulonephritis, etc.), cardiomyopathy (e.g. dilated cardiomyopathy), diabetes, diabetic complications (e.g. diabetic nephropathy, diabetic neuropathy, diabetic retinopathy), influenza, glomerulonephritis, and ulcerative colitis, preferably AIDS, joint tissue destruction in rheumatism, inflammation, hepatitis (e.g. fulminant hepatitis), and autoimmune disease (e.g. systematic lupus erythematosus, immune complex glomerulonephritis, etc.).

When the compound obtained by the screening method of the present invention or by using the screening kit of the present invention is used as the therapeutic or prophylactic agent, it can be formulated to tablets, capsules, slixirs, microcapsules, aspetic solution, suspensions or the like in the same way as the pharmaceutical composition comprising the protein, etc. of the present invention as mentioned above.

Because the thus-obtained preparation is safe and of low toxicity, it can be administered to humans or mammals (e.g., rat, mouse, guinia pig, rabbit, sheep, pig, bovine, horse, cat, dog, monkey, etc.).

The dose of the protein, etc. of the present invention may vary depending on subject disease, subject of administration, and so on. When the compound which promotes the intracellular signal transduction is used, for example, for treating cancer by oral administration, the dose of the compound is normally about 0.1 to 100 mg, preferably 1.0 to 50 mg, and more preferably 1.0 to 20 mg per day for an adult (weighing 60 kg). When the compound which promotes the intracellular signal transduction is used, for example, for treating cancer by non-oral administration, it is advantageous to administer the compound in the form of injectable preparation at a daily dose of about 0.01 to 30 mg, preferably about 0.1 to 20 mg, and more preferably about 0.1 to 10 mg per administration by an intravenous injection for an adult (weighing 60 kg), depending on subject of administration, subject disease and so on. For other animal species, corresponding does as converted per 60 kg weight can be administered.

When the compound which inhibits the intracellular signal transduction is used, for example, for treating AIDS by oral administration, the dose of the compound is normally about 0.1 to 100 mg, preferably 1.0 to 50 mg, and more preferably 1.0 to 20 mg per day for an adult (weighing 60 kg). When the compound which inhibits the intracellular signal transduction is used, for example, for treating AIDS by non-oral administration, it is advantageous to administer the compound in the form of injectable preparation at a daily dose of about 0.01 to 30 mg, preferably about 0.1 to 20 mg, and more preferably about 0.1 to 10 mg per administration by an intravenous injection for an adult (weighing 60 kg), depending on subject of administration, subject disease and so on. For other animal species, corresponding does as converted per 60 kg weight can be administered.

(6) The Antisense DNA

The antisense DNA which is capable of complementary binding to the DNA or mRNA coding for the protein, etc. of the present invention and suppresses the expression of the DNA or mRNA and the protein, etc. of the present invention is capable of inhibiting the function of the protein, etc. or the DNA coding for the protein, etc. of the present invention which show the above-mentioned activities in vivo. Therefore, this antisense DNA is used for a prophylactic or therapeutic agent for various diseases such as AIDS, neurodegenerative disease (e.g. Alzheimer's disease, Parkinson's disease, amyotrophic lateral sclerosis, pigmentary retinitis, cerebellar degeneration, etc.), diseases due to osteomyelodysplasia (e.g. aplastic anemia etc.), ischemic disease (e.g. myocardial infarction, stroke, etc.), joint tissue destruction in rheumatism, hepatitis (e.g. fulminant hepatitis), autoimmune disease (e.g. systematic lupus erythematosus, immune complex glomerulonephritis, etc.), cardiomyopathy (e.g. dilated cardiomyopathy), diabetes, diabetic complications (e.g. diabetic nephropathy, diabetic neuropathy, diabetic retinopathy), influenza, glomerulonephritis, and ulcerative colitis, preferably AIDS, joint tissue destruction in rheumatism, hepatitis (e.g. fulminant hepatitis), and autoimmune disease (e.g. systematic lupus erythematosus, immune complex glomerulonephritis, etc.).

When the antisense DNA is used for the prophylactic or therapeutic agent, it can be formulated in the same way as the prophylactic or therapeutic composition containing the DNA of the present invention. The DNA may be used alone or after inserting it into a suitable vector such as retrovirus vector, adenovirus vector, adenovirus-associated virus vector, pox virus etc. followed by subjecting the product vector to a conventional means. The DNA can also be administered as "naked" DNA, with physiologically acceptable carriers such as adjuvants to assist in uptake, by "gene" gun or by a catheter such as a catheter with a hydrogel.

In addition, this antisense DNA can be used as a diagnostic oligonucleotide probe for investigating the presence of the DNA of the present invention or the status of its expression in various tissues and cells.

(7) Construction of a Transgenic Animal

The present invention further provides a non-human mammal harboring a foreign DNA coding for the protein of the present invention (hereinafter referred to briefly as foreign DNA) or a mutant thereof (sometimes referred to briefly as a foreign mutant DNA).

Thus, the present invention provides (1) A non-human mammal harboring a foreign DNA of the present invention or a foreign mutant DNA thereof:

(2) The non-human mammal according to (1) which is a rodent:

(3) The non-human mammalian according to (2) wherein the rodent is a mouse; and (4) A recombinant vector containing the foreign DNA of the present invention or a foreign mutant DNA thereof and capable of being expressed in a mammal.

The non-human mammal harboring the foreign DNA of the present invention or a foreign mutant DNA thereof (hereinafter referred to briefly as the transgenic animal of the present invention) can be constructed by transferring the objective DNA to a germinal cell such as an unfertilized egg cell, fertilized egg cell, or sperm cell or its primordial cell, preferably in the period of embryogenesis in the ontogenesis of a non-human mammal (more preferably in the stage of a single cell or a fertilized egg cell and generally at the 8-cell stage or earlier), by the calcium phosphate method, electric pulse method, lipofection method, agglutination method, microinjection method, particle gun method, or DEAE-dextran method.

The non-human mammal used includes bovine, swine, sheep, goat, rabbit, canine, feline, guinea pig, hamster, murine, rat, and so on. From the standpoint of construction of a diseased animal model, rodents which have comparatively short ontogenesis and life cycles and can be easily bred, particularly mice (e.g. pure strains such as C57BL/6, DBA2, etc. and hybrid strains such as B6C3F$_1$, BDF$_1$, B6D2F$_1$, BALB/c, ICR, etc.) or rats (e.g. Wistar, SD, etc.) are preferred.

The "mammal" as mentioned with reference to the recombinant vector capable of being expressed in a mammal includes the same non-human mammals as those mentioned above and humans.

The foreign DNA of the present invention is not a DNA of the present invention which is inherently harbored by the non-human mammal, but a DNA of the present invention as isolated or extracted from a mammal. Preferable examples of the DNA are a DNA having a nucleotide sequence represented by SEQ ID NO:9.

The mutant DNA includes not only the DNAs available upon variation (e.g. mutation) of the nucleotide sequence of the original DNA of the present invention, for example, upon addition or deletion of nucleotide sequence or substitution of other, and includes abnormal DNAs.

The term "abnormal DNA" as used herein means any DNA that causes an expression of an abnormal protein of the present invention, for example, an expression of a protein which suppresses the function of the normal protein of the present invention.

The foreign DNA of the present invention may be one derived from a mammal of the same species as the host animal or a mammal of a different species. For transfer of the DNA of the present invention to the host animal, it is generally advantageous to use a DNA construct prepared by linking the DNA at downstream of a promoter capable of being expressed in animal cells. For example, in transferring the human-derived DNA of the present invention, this human DNA of the present invention can be linked at downstream of a promoter capable of causing expression of DNAs derived from various animals (e.g. rabbit, canine, feline, guinea pig, hamster, rat, murine, etc.) harboring the DNA of the present invention having high homology thereto to prepare a DNA construct (e.g. a vector) which can then be microinjected into the fertilized egg cell of a host mammal such as a fertilized murine egg cell, whereby a transgenic mammal showing a high expression of the DNA of the present invention can be provided.

Examples of the expression vector used for the protein of the present invention are plasmids derived from *E. coli*, plasmids derived from *B. subtilis*, plasmids of the yeast origin, λ phage and other bacteriophages, retroviruses such as Molony leukemia virus, and animal viruses such as vaccinia virus and vaculovirus. Preferable examples are plasmids of the *E. coli* origin, plasmids of the *B. subtilis* origin, and yeast-derived plasmids.

The promoter for the regulation of the expression of the DNA are (1) promoters for DNAs derived from viruses (e.g. simian virus, cytomegalovirus, Molony leukemia virus, JC virus, papilloma virus, poliovirus, etc.), (2) promoters derived from mammals (e.g. man, rabbit, dog, cat, guinea pig, hamster, rat, mouse, etc.) for albumin, insulin II, uroprakin II, elastase, erythropoietin, endothelin, muscle creatine kinase, glial fibrillary acidic protein, glutathione S-transferase, platelet-derived growth factor β, keratin K1, K10, and K14, collagen type I and type II, cyclic AMP-dependent protein kinase βI subunit, dystrophin, tartaric acid-resistant alkaline phosphatase, atrial natriuretic factor, endothelial receptor tyrosine kinase (generally abbreviated as Tie2), sodium/potassium-exchanging adenosinetriphosphatase (Na$^+$, K$^+$-ATPase), neurofilament light chain, metallothionein I and IIA, metalloprotease I tissue inhibitor, MHC Class I antigen (H-2L), H-ras, renin, dopamine β-hydroxylase, thyroid peroxidase (TPO), polypeptide chain elongation factor 1α (EF-1α), β actin, α-and β-myosin heavy chain, myosin light chains 1 and 2, myelin basic protein, thyroglobulin, Thy-1, immunoglobulin H chain variable region (VNP), serum amyloid P component, myoglobin, troponin C, smooth muscle α-actin, preproenkephalin A or vasopressin, and so on. Preferable promoters are promoters conducive to high expression in the whole body, such as cytomegalovirus promoter, human polypeptide chain elongation factor 1α (EF-1α) promoter, and human and chicken β-actin promoters.

The vector preferably has a sequence for terminating the transcription of the objective mRNA (generally called terminator) in the transgenic mammal. The examples of the sequence are sequences derived from viruses, various mammals. Preferable examples are the SV40 terminator derived from simian virus, and so on.

In addition, for enhanced the expression of the objective DNA, it is possible, depending on the specific objective, to link the splicing signal, enhancer domain, a portion of the eucaryotic DNA intron, etc. at upstream of the 5'-end of the promoter region, between the promoter region and the translated region, or at downstream of the 3'-end of the translated region.

The translated region of the normal protein of the present invention can be obtained, as the whole or part of the genomic DNA, from the DNAs derived from the liver, kidney, or thyroid cells or fibroblasts of various mammals (e.g. rabbit, canine, feline, guinea pig, hamster, rat, murine, man, etc.) or from various commercial genomic DNA libraries, or starting with the complementary DNAs prepared from RNAs derived from the liver, kidney, thyroid cells or fibroblasts by the known technique. The foreign abnormal DNA can be constructed by mutating the translated region of the normal protein obtained from the above-mentioned cells or tissues by the mutagenesis method.

The translated region can be prepared as a DNA construct which can be expressed in a transgenic animal, by the routine recombinant DNA technique, i.e. by coupling it at downstream of the promoter and, if desired, at upstream of the transcription termination site.

The transfer of the DNA of the present invention at the fertilized egg cell stage insures that the DNA will be ubiquitous in all the germ cells and somatic cells of the host mammal. The presence of the DNA of the present invention in the germ cells of the transgenic animal following DNA transfer means that all the germ cells and somatic cells of all the progeny of the transgenic animal harbor the DNA of the present invention. Thus, the offspring of animals of this line to which DNA is passed down have the DNA of the present invention in their germ cells and somatic cells.

The non-human mammal to which the foreign normal DNA of the present invention has been transferred can be verified by mating to retain the DNA stably and then bred as a strain harboring the transferred DNA from generation to generation under the usual breeding conditions. The transfer of the DNA of the present invention in the fertilized egg cell stage is carried out in such a manner that the transferred DNA will be present in excess in all the germ cells and somatic cells of the transgenic animal. The presence of an excess of the DNA of the present invention in the germ cells of the transgenic animal means that all the progeny of this line harbor an excess of the DNA of the present invention in their germ cells and somatic cells. By preparing homozygous animals having the transferred DNA in both homologous chromosomes and mating the animals of both sexes, they can be bred serially so that all the progeny may harbor an excess of the DNA.

The non-human mammal harboring the normal DNA of the present invention features a high expression of the DNA and may eventually develop a hyperergasia of the protein of the present invention through activation of the function of the endogenous normal DNA and, therefore, can be utilized as an animal model of the disease. For example, by using the transgenic animal harboring the normal DNA of the present invention, it is possible to study the hyperergasia of the protein of the present invention to elucidate the mechanisms of diseases with which the protein of the present invention is associated, and explore therapeutic modalities for the diseases.

Furthermore, the mammal to which the foreign normal DNA of the present invention has been transferred presents with symptoms due to an increase in the free protein of the present invention and, therefore, can also be used in the screening of therapeutic drugs for diseases with which the protein of the present invention is associated.

On the other hand, the non-human mammal harboring the foreign abnormal DNA of the present invention can be verified by mating to retain the DNA stably and then bred as a line harboring the DNA from generation to generation under the usual breeding conditions. Moreover, it is possible to incorporate the objective DNA in the above-mentioned plasmid for use as a starting material. The DNA construct with the promoter can be prepared by the routine recombinant DNA technique. Transfer of the abnormal DNA of the present invention in the fertilized egg cell stage insures that the transferred DNA will be ubiquitous in all the germ cells and somatic cells of the host mammal. The presence of the abnormal DNA of the present invention in the germ cells of the transgenic animal means that all the offspring of this transgenic animal harbor the abnormal DNA of the present invention in all of their germ cells and somatic cells. The progeny of this animal harbor the abnormal DNA of the present invention in all of their germ cells and somatic cells. By preparing homozygous male and female animals having the introduced DNA in both homologous chromosomes and mating them, it can be insured that all their offsprings harbor the DNA.

The non-human mammal harboring the abnormal DNA of the present invention features a high expression of the abnormal DNA and, therefore, may eventually develop adiaphoria associated with functional inactivation of the protein of the present invention through inhibition of the function of the endogenous normal DNA and, therefore, can be utilized as an animal model of the disease. For example, by using the transgenic animal harboring the abnormal DNA of the present invention, analysis of the mechanism of this functional inactivation adiaphoria due to the protein of the present invention and therapeutic modalities for the disease can be explored.

As a specific potential use, the transgenic animal with a high expression of the abnormal DNA of the present invention can be used as a model for elucidating the functional inhibition of the normal protein by the abnormal protein of the present invention (dominant negative effect) in adiaphoria of functional inactivation type due to the protein of the present invention. Moreover, the transgenic mammal harboring the foreign abnormal DNA of the present invention develops symptoms due to an increase in the free protein of the present invention and, therefore, can be utilized in the screening of therapeutic compounds for adiaphoria due to functional inactivation of the protein of the present invention.

As other potential uses for transgenic animals harboring the two kinds of. DNAs described above, the following uses can be suggested.

(1) Use as a cell source for tissue culture;

(2) Analysis of the relationship of the protein of the present invention to proteins which are specifically expressed or activated by the protein by direct analysis of DNAs or RNAs in the tissues of the transgenic mammal harboring the DNA of the present invention or analysis of the composition of the protein expressed by the DNA;

(3) Study of the functions of cells of those tissues which are generally difficult to culture by using the cells from the tissues containing the DNA as cultured by the standard tissue culture technique;

(4) Screening of drugs capable of enhancing the cell functions by using the cells described in (3);

(5) Isolation and purification of the muteins of the present invention and construction of antibodies to the muteins.

Furthermore, by using the transgenic animal of the present invention, clinical symptoms of diseases associated with the protein of the present invention, inclusive of said adiaphoria associated with functional inactivation of the protein of the present invention, can be investigated. In addition, more detailed pathological findings can be generated in various organs of this model of diseases associated with the protein of the present invention, thus contributing to the development of new therapies and the study and treatment of secondary diseases arising from such diseases.

Moreover, following isolation of various organs from the transgenic animal of the present invention and their mincing and digestion with a proteolytic enzyme such as trypsin, free single cells harboring the transferred gene can be recovered and cultured for establishment of a cell line. Furthermore, characterization of cells producing the protein of the present invention can be made and their relationship to apotosis, differentiation, or proliferation, the mechanism of signal transduction in them, and abnormalities involved can be explored to thereby generate information useful for a further elucidation of the protein of the present invention and its actions.

Moreover, for the development of therapeutic drugs for diseases associated with the protein of the present invention, such as adiaphoria due to functional inactivation of the protein of the present invention by using the transgenic animal of the present invention, an effective and rapid screening technology for such therapeutic drugs can be established by using the test and assay methods described hereinbefore. In addition, by using the above transgenic animal or the foreign DNA expression vector of the present invention, gene therapies for diseases associated with the protein of the present invention can be explored and developed.

(8) Construction of Knockout Animals

The present invention further provides a non-human mammalian embryonic stem cell wherein the DNA of the present invention is inactivated and a non-human mammal deficient in expression of the DNA of the present invention wherein the DNA is inactivated.

The present invention, therefore, provides:

(1) A non-human mammalian embryonic stem cell wherein the DNA of the present invention is inactivated;

(2) The non-human mammalian embryonic stem cell according to in (1) wherein the DNA is inactivated by introduction of a reporter gene (e.g. a β-galactosidase gene of the E. coli origin);

(3) The non-human mammalian embryonic stem cell according to (1) which is neomycin-resistant;

(4) The non-human mammalian embryonic stem cell according to (1) wherein the non-human mammal is a rodent;

(5) The non-human mammalian embryonic stem cell according to (4) wherein the rodent is a mouse;

(6) A non-human mammal deficient in expression of the DNA of the present invention, wherein the DNA is inactivated;

(7) The non-human mammal according to (6) wherein the DNA is inactivated by introduction of a reporter gene (e.g. a β-galactosidase gene of E. coli origin) and the reporter gene can be expressed under the control of the promoter against the DNA of the present invention;

(8) The non-human mammal according to (6) wherein the non-human mammal is a rodent;

(9) The non-human mammal according to (8) wherein the rodent is a mouse; and

(10) A method for screening for a compound or a salt thereof which enhances or inhibits an activity of the promoter against the DNA of the present invention, which comprises administering a test compound to the non-human mammal according to (7) and detecting an expression of the reporter gene.

The DNA comprising the murine-derived genomic DNA having the nucleotide sequence represented by SEQ ID NO:9 (FIG. 4) is preferably used for preparation the knockout mouse of the present invention.

The term "non-human mammalian embryonic stem cell wherein the DNA of the present invention in inactivated" means the embryonic stem cell (hereinafter referred to briefly as ES cell) of a non-human mammal in which the DNA has been deprived of the capacity to express the protein of the present invention (hereinafter referred to sometimes as the knockout DNA of the present invention) through introduction of an artificial mutation to the DNA of the present invention possessed by the non-human mammal to thereby inhibit expression of the DNA of the present invention or through substantial deprivation of the activity of the protein of the present invention which is encoded by the DNA.

The non-human mammal includes the same animals mentioned hereinbefore.

Examples of the method for introducing an artificial mutation to the DNA of the present invention are a deletion of some or all of the DNA sequence, or an insertion or substitution of a different DNA by the genetic engineering technology. By such a mutation, the codon reading frame can be shifted or the function, of the promoter or exon can be disrupted to provide the knockout DNA of the present invention.

The non-human mammalian embryonic stem cell wherein the DNA of the present invention is inactivated (hereinafter referred to as the ES cell wherein the DNA is the inactivated of the present invention or the knockout ES cell of the present invention) can be prepared by, for example, a procedure which comprises isolating the DNA of the present invention from an objective non-human mammal, inserting a drug-resistance gene, typically the neomycin-resistance gene or hygromycin-resistance gene, or a reporter gene such as lacZ (β-galactosidase gene) or cat (chloramphenicol acetyltransferase gene) in its exon region to disrupt the function of the exon or inserting a DNA sequence for terminating gene transcription (e.g. poly A coupling signal) in the intron region between exons to thereby inhibit synthesis of a complete mRNA, introducing the thus-constructed DNA chain having a DNA sequence adapted to eventually disrupt the gene (hereinafter referred to briefly as the targeting vector) into the chromosomes of the host animal by homologous recombination, subjecting the resulting ES cell to Southern hybridization analysis using the DNA sequence on the DNA of the present invention or in its vicinity as the probe or a PCR procedure using the DNA sequence on the targeting vector and a DNA sequence in the vicinity but not including the DNA of the present invention used in the construction of the targeting vector as primers, and selecting the knockout ES cell of the present invention.

Moreover, the original ES cell used for inactivation of the DNA of the present invention by the homologous recombination technique or the like may be an already established cell line such as those mentioned hereinbefore or a new cell line established de novo by the known method of Evans and Kaufma. Taking murine ES cells as an example, ES cells of the 129 line are generally employed but the immunological background of this line is not clear. Therefore, the cell line established by using $BDF_1$ mice created by the hybridization of C57BL/6 mice and C57BL/6 mice, both yielding few eggs, with DBA/2 mice ($BDF_1=F_1$ of C57BL/6 and DBA/2) for preparing pure-line ES cells with an immunologically defined genetic background can be used with advantage. In addition to the advantage of high egg output and sturdiness of the egg, $BDF_1$ mice have the background of C57BL/6 mice so that in the construction of a disease model with ES cells obtained, the genetic background of the model mice can be converted to that of C57BL/6 mice by back-crossing with C57BL/6.

Moreover, in establishing an ES cell line, it is common practice to use blastocytes 3.5 days following fertilization but, aside from them, a large number of early embryos can be prepared with high efficiency by harvesting the embryos at the 8-cell stage and culturing them into blastocytes.

Furthermore, while ES cells from both male and female animals can be employed, generally ES cells of a male animal are more convenient for the construction of reproduction line chimeras. Moreover, for the purpose of reducing the burden of the complicated cultural procedure, it is preferable to carry out sexing as early as possible.

As a typical method for sexing ES cells, there can be mentioned the method in which the gene in the sex determination region on the Y chromosome is amplified and detected by PCR. Whereas the conventional karyotype analysis requires about $10^6$ cells, the above method requires only about one colony equivalent of ES cells (about 50 cells). Therefore, the primary selection of ES cells in an early stage can be made by this sexing method. Since male cells can thus be selected in the early stage, the trouble in the initial stage of culture can be drastically reduced.

Moreover, the secondary selection can be carried out by G-banding for the number of chromosomes. The number of chromosomes in the resulting ES cell is preferably 100% of the normal number but this goal may not be reached due to the physical and other factors involved in the establishment of the line. In such cases, it is preferable to knockout the gene of the ES cell and reclone it in the normal cell (taking a mouse as an example, the cell in which the number of chromosomes is 2n=40).

The embryonic stem cell line thus established is generally very satisfactory in proliferation characteristic but since it is liable to lose its ontogenic ability, it must be subcultured with sufficient care. For example, this cell line should be cultured on suitable feeder cells such as STO fibroblasts in the presence of LIF (1–10000 U/ml) in a carbon dioxide incubator (preferably 5% $CO_2$-95% air or 5% oxygen-5% $CO_2$-90% air) at about 37° C. and, in subculture, it should be treated with trypsin/EDTA solution (generally 0.001–0.5% trypsin/0.1–5 mM EDTA, preferably about 0.1% trypsin/1 mM EDTA) to provide single cells and seed them on freshly prepared feeder cells. While such subculture is generally performed every 1–3 days, it is good practice to observe the cells on each occasion and, whenever morphologically abnormal cells are discovered, discard the culture.

ES cells can be allowed to differentiate into various types of cells, such as head long muscle cells, visceral muscle cells, heart muscle cells, etc. by conducting monolayer culture to a high density under suitable conditions or suspension culture until a mass of cells is formed (M. J. Evans & M. H. Kaufman, Nature, 292, 154, 1981; G. R. Martin, Proceedings of National Academy of Science USA, 78, 7634, 1981; T. C. Doetschman et al., Journal of Embryology and Experimental Morphology, 87, 27, 1985), and the cell deficient in expression of the DNA of the present invention as obtained by causing the ES cell of the present invention to differentiate is useful for the cytobiological in vitro study of the protein of the present invention.

The non-human mammal deficient in expression of the DNA of the present invention can be differentiated from the normal animal by assaying the mRNA in the animals by the known method and comparing the amounts of expression indirectly.

The non-human mammal used for this purpose includes the animals mentioned hereinbefore.

Referring to the non-human mammal deficient in expression of the DNA of the present invention, the DNA of the present invention can be knocked out by introducing the targeting vector constructed as above into, for example, a murine embryonic stem cell or a murine egg cell and thereby causing the DNA sequence of the targeting vector harboring the inactivated DNA of the present invention to undergo homologous recombination with, and accordingly replacing, the DNA of the present invention on the murine embryonic stem cell or egg cell chromosomes.

The cell with the DNA of the present invention thus knocked out can be obtained by Southern hybridization analysis using a DNA sequence on the DNA of the present invention or in its vicinity as a probe or by PCR using a DNA sequence on the targeting vector or a murine-derived DNA sequence in a region adjacent to but not including the DNA of the present invention used in the targeting vector as primers. When a non-human mammalian embryonic stem cell is used, a cell line with the DNA of the present invention knocked out by the homologous recombination technique is cloned and injected into the non-human mammalian embryo or blastocyte at a suitable stage of embryogenesis, for example at the 8-cell stage, and the resulting chimera embryo is transplanted in the pseudopregnant uterus of the non-human mammal. The animal thus obtained is a chimera animal constituted by both the cells harboring the normal DNA of the present invention and the cells harboring the artificially mutated DNA of the present invention.

When some of the gametes of this chimera animal harbor the mutated DNA of the present invention, an individual the entire tissues of which are constituted by cells harboring the mutated DNA of the present invention can be screened from the colony of animals obtained by crossing such a chimera animal with a normal animal, for example by coat color discrimination. The individuals thus selected are usually animals deficient in hetero-expression of the protein of the present invention and by mating such individuals deficient in hetero-expression of the protein of the present invention with each other, animals deficient in homo-expression of the protein of the present invention can be acquired.

When an egg cell is used, a transgenic non-human mammal with the targeting vector having been introduced into its chromosomes can be prepared by injecting the DNA solution into the egg cell nucleus by the microinjection technique and selecting animals expressing a mutation of the DNA of the present invention by homologous recombination.

The individuals with the DNA of the present invention knocked out are mated to verify that the animals obtained by mating also have the DNA knocked out and they can be sub-bred under the usual breeding conditions.

Preparation and maintenance of the reproduction line can also be carried out in the routine manner. Thus, by mating male and female animals harboring the inactivated DNA, homozygotes having the inactivated DNA in both homologous chromosomes can be obtained. The homozygotes thus obtained are bred under such conditions that, with regard to the dam, the number of homozygotes is plural per normal individual. By mating male and female heterozygotes, homozygotes and heterozygotes both harboring the inactivated DNA can be sub-bread.

The non-human mammalian embryonic stem cell harboring the inactivated DNA of the present invention is very useful for the construction of non-human mammals deficient in expression of the DNA of the present invention. Moreover, the mouse deficient in expression of the protein of the present invention lacks the various biological activities inducible by the protein of the present invention and can, therefore, be of use as an animal model of diseases arising from inactivation of the biological activities of the protein of the present invention, thus being of use in the etiological studies of diseases and development of therapeutics.

(8a) A method for screening for a compound having therapeutic or prophylactic effect in the various diseases caused by a defect in or damage to the DNA of the present invention A non-human mammal deficient in expression of the DNA of the present invention can be used in the screening for a compound having therapeutic or prophylactic effect in the diseases (e.g. cancer) caused by a defect in or damage to the DNA of the present invention.

Thus, the present invention provides a method for screening for a compound, or a salt thereof, which has therapeutic or prophylactic effect in the diseases caused by a defect in or damage to the DNA of the present invention, which method comprises administering a test compound to a non-human mammal deffficient in expression of the DNA of the present invention and monitoring or measuring a change of the non-human mammal.

The non-human mammal deficient in expression of the DNA of the present invention, which is to be used in this screening method, includes the same animals as those mentioned above.

The test compound includes peptides, proteins, non-peptide compounds, synthetic compounds, fermentation products, cell extracts, plant extracts, animal tissue extracts, blood plasma and son on. The test compound may be novel or known compounds.

More specifically, a non-human mammal deficient in expression of the DNA of the present invention is treated with the test compound and the treated animal is compared with an untreated control to evaluate the test compound for therapeutic or prophylactic effect by using a change in some organ or tissue or in a disease symptom as an indicator.

The method of treating the test animal with a test compound can be selected according to the symptom or symptoms manifested by the test animal and the characteristics of the test compound, among other factors and, for example, oral administration or intravenous injection can be employed. The dosage of the test compound can be suitably selected according to the route of administration, the properties of the test compound, and other conditions.

In the screening for a compound with therapeutic or prophylactic effect in cancer, for instance, the test compound is administered to the non-human mammals deficient in expression of the DNA of the present invention. And, changes in, body weight, etc. in the animal are determined at timed intervals.

When, in the screening method, the body weight in the test animal is increased about 10% or more, preferably about 30% or more, more preferably about 50% or more, following administration of the test compound, the particular test compound can be selected as a compound capable of producing therapeutic or prophylactic effect in cancer.

The compound obtained by the above screening method has therapeutic or prophylactic effect in the diseases (e.g. cancer, viral infection, *Helicobacter pylori* infection, invasive staphylococcia, hepatitis, nephritis, autoimmune disease, bone disease, atherosclerosis or pain) caused by a defect in or damage to the protein, etc. of the present invention and, therefore, can be used as a drug, for example as a safe, low-toxicity therapeutic or prophylactic agent for the diseases. Furthermore, compounds derived from the compound obtained by the above screening may also be used in the same manner.

The salts of the compound obtained by the screening method as mentioned above include salts with physiologically acceptable bases (e.g. alkali metals) or acids such as organic or inorganic acids, and are preferably a physiologically acceptable acid addition salt. Examples of such salts are salts thereof with inorganic acids (e.g. hydrochloric acid, phisphoric acid, hydrobromic acid or sulfuric acid, etc.) and salts thereof with organic acids (e.g. acetic acid, formic acid, propionic acid, fumaric acid, maleic acid, succinic acid, tartaric acid, citric acid, malic acid, oxalic acid, benzoic acid, methanesulfonic acid or benzenesulfonic acid, etc.).

The therapeutic or prophylactic composition comprising the compound obtained the screening method can be prepared in the same as the pharmaceutical composition comprising the protein, etc. of the present invention as mentioned above.

Because the thus-obtained preparation is safe and of low toxicity, it can be administered to humans or mammals (e.g., rat, mouse, guinia pig, rabbit, sheep, pig, bovine, horse, cat, dog, monkey, etc.).

The dose of the compound may vary depending on subject disease, subject of administration, way of administration, and so on. When the compound is used, for example, for treating cancer by oral administration, the dose of the compound is normally about 0.1 to 100 mg, preferably 1.0 to 50 mg, and more preferably 1.0 to 20 mg per day for an adult (weighing 60 kg). When the compound is used, for example, for treating cancer by non-oral administration, it is advantageous to administer the compound in the form of injectable preparation at a daily dose of about 0.01 to 30 mg, preferably about 0.1 to 20 mg, and more preferably about 0.1 to 10 mg per administration by an intravenous injection for an adult (weighing 60 kg), depending on subject of administration, subject disease and so on. For other animal species, corresponding does as converted per 60 kg weight can be administered.

(8b) A method for screening for a compound capable of promoting or inhibiting an activity of the promoter for the DNA of the present invention The present invention provides a method for screening for a compound, or a salt thereof, which promotes or inhibits an activity of the promoter for the DNA of the present invention, which method comprises administering a test compound to a non-human mammal deficient in expression of the DNA of the present invention, wherein the DNA of the present invention is inactivated by introducing of a reporter gene and detecting the expression of the reporter gene.

As the test compound, the same compounds as those mentioned hereinbefore can be used.

Examples of the reporter gene are the same genes as those mentioned hereinbefore. Preferable examples are a β-galactosidase gene (lacz) and so on.

In non-human mammals deficient in expression of the DNA of the present invention wherein the DNA of the present invention is inactivated by introducing a reporter gene, the reporter gene is under the control of the promoter for the DNA of the present invention and, therefore, the activity of the promoter can be detected by tracing the expression of the substance encoded by the reporter gene.

For instance, when part of the DNA region coding for the protein of the present present invention has been inactivated by the *Escherichia coli*-derived β-galactosidase gene (lacZ), β-galactosidase is expressed in those tissues in which, the protein of the present invention would have been expressed. Therefore, the status of expression of the protein of the present invention in a living animal body can be traced, easily and expediently, for example, by the staining method using a reagent serving as a substrate for β-galactosidase, such as 5-bromo-4-chloro-3-indolyl-β-galactopyranoside (X-gal). More specifically, a tissue section of a mouse defective in the protein of the present invention is fixed with glutaraldehyde or the like, washed with Dulbecco's phosphate-buffered saline (PBS), and reacted with a staining solution containing X-gal at room temperature or around 37° C. for about 30 minutes to 1 hour. The tissue sample is then washed with 1 mM EDTA/PBS solution to terminate the β-galactosidase reaction and observed for color development. Alternatively, the mRNA coding for lacZ may be detected by a conventional method.

The compound, or a salt thereof, as obtained by the above screening method is a compound selected from among the test compounds mentioned above and, as such, is a compound capable of promoting or inhibiting the activity of the promoter for the DNA of the present invention.

The salts of the compound obtained by the screening method as mentioned above include salts with physiologically acceptable bases (e.g. alkali metals) or acids such as organic or inorganic acids, and are preferably a physiologically acceptable acid addition salt. Examples of such salts are salts thereof with inorganic acids (e.g. hydrochloric acid, phisphoric acid, hydrobromic acid or sulfuric acid, etc.) and salts thereof with organic acids (e.g. acetic acid, formic acid, propionic acid, fumaric acid, maleic acid, succinic acid, tartaric acid, citric acid, malic acid, oxalic acid, benzoic acid, methanesulfonic acid or benzenesulfonic acid, etc.).

The compound, or a salt thereof, which promotes the activity of the promoter for the DNA of the present invention is capable of promoting the expression of the protein of the present invention and, hence, the promoting function of the protein. Therefore, the compound is useful as a drug, such as a safe, low-toxic therapeutic or prophylactic agent for diseases such as cancer, viral infection, *Helicobacter pylori* infection, invasive staphylococcia, hepatitis, nephritis, autoimmune disease, bone disease, atherosclerosis or pain.

On the other hand, the compound, or a salt thereof, which inhibits the activity of the promoter for the DNA of the present invention is capable of inhibiting expression of the protein of the present invention and, hence, inhibiting the function of the protein. Therefore, the compound is useful as a drug, such as a safe, low-toxic therapeutic or prophylactic agent for diseases such as AIDS, inflammation, neurodegenerative disease due to osteomyelodysplasia, ischemic disease, destruction of joint tissues in rheumatism, hepatitis, autoimmune disease, cardiomyopathy, diabetes, diabetic complications, influenza, glomerulonephritis or uncerative colitis, particulary, AIDS, inflammation, destruciton of joint tissues in rheumatism, hepatitis or autoimmune disease.

Furthermore, compounds derived from the compound obtained by the above screening method may also be used in the same way.

The therapeutic or prophylactic agent comprising the compound obtained the screening method can be prepared in the same as the pharmaceutical composition comprising the protein, etc. of the present invention as mentioned above.

Because the thus-obtained preparation is safe and of low toxicity, it can be administered to humans or mammals (e.g., rat, mouse, guinia pig, rabbit, sheep, pig, bovine, horse, cat, dog, monkey, etc.).

The dose of the compound may vary depending on subject disease, subject of administration, way of administration, and so on. When the compound which promotes an activity of the promoter is used, for example, for treating cancer by oral administration, the dose of the compound which promotes an activity of the promoter is normally about 0.1 to 100 mg, preferably 1.0 to 50 mg, and more preferably 1.0 to 20 mg per day for an adult (weighing 60 kg). When the compound which promotes an activity of the promoter is used, for example, for treating cancer by non-oral administration, it is advantageous to administer the compound which promotes an activity of the promoter in the form of injectable preparation at a daily dose of about 0.01 to 30 mg, preferably about 0.1 to 20 mg, and more preferably about 0.1 to 10 mg per administration by an intravenous injection for an adult (weighing 60 kg), depending on subject of administration, subject disease and so on. For other animal species, corresponding does as converted per 60 kg weight can be administered.

When the compound which inhibits an activity of the promoter is used, for example, for treating AIDS by oral administration, the dose of the compound which inhibits an activity of the promoter is normally about 0.1 to 100 mg, preferably 1.0 to 50 mg, and more preferably 1.0 to 20 mg per day for an adult (weighing 60 kg). When the compound which inhibits an activity of the promoter is used, for example, for treating AIDS by non-oral administration, it is advantageous to administer the compound which inhibits an activity of the promoter in the form of injectable preparation at a daily dose of about 0.01 to 30 mg, preferably about 0.1 to 20 mg, and more preferably about 0.1 to 10 mg per administration by an intravenous injection for an adult (weighing 60 kg), depending on subject of administration, subject disease and so on. For other animal species, corresponding does as converted per 60 kg weight can be administered.

In the specification, claims and drawings of the present application, the abbreviations used for bases (nucleotides), amino acids and so forth are those recommended by the IUPAC-IUB Commission on Biochemical Nomenclature or those conventionally used in the art. Examples thereof are given below. Amino acids for which optical isomerism is possible are, unless otherwise specified, in the L form.

DNA: Deoxyribonucleic acid
cDNA: Complementary deoxyribonucleic acid
A: Adenine
T: Thymine
G: Guanine
C: Cytosine
RNA: Ribonucleic acid
mRNA: Messenger ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
EDTA: Ethylenediaminetetracetic acid
SDS: Sodium dodecyl sulfate
Gly: Glycine
Ala: Alanine
Val: Valine
Leu: Leucine
Ile: Isoleucine
Ser: Serine
Thr: Threonine
Cys: Cysteine
Met: Methionine
Glu: Glutamic acid
Asp: Aspartic acid
Lys: Lysine
Arg: Arginine
His: Histidine
Phe: Phenylalanine
Tyr: Tyrosine
Trp: Tryptophan
Pro: Proline
Asn: Asparagine
Gln: Glutamine
pGlu: Pyroglutamic acid Substitution groups, protecting groups and reagents used in the specification of the present application are represented by the symbols set forth below.

Me: Methyl
Et: Ethyl
Bu: Butyl
Ph: Phenyl
TC: Thiazolidine-4(R)-carboxamide
Tos: p-Toluenesulfonyl
CHO: Formyl
Bzl: Benzyl
$Cl_2$-Bzl: 2,6-Dichlorobenzyl
Bom: Benzyloxymethyl
Z: Benzyloxycarbonyl
Cl-Z: 2-Chlorobenzyloxycarbonyl
Br-Z: 2-Bromobenzyloxycarbonyl
Boc: tert-Butoxycarbonyl
DNP: Dinitrophenyl
Trt: Trityl
Bum tert-Butoxymethyl
Fmoc: N-9-Fluorenylmethyloxycarbonyl
HOBt: 1-Hydroxybenzotriazole
HOOBt: 3,4-Dihydro-3-hydroxy-4-oxo-1,2,3-benzotriazine
HONB: 1-hydroxy-5-norbornene-2,3-dicarboximide
DCC: Dicyclohexylcarbodiimide SEQ ID NO:1 shows the amino acid sequence of a human protein of the present invention;

SEQ ID NO:2 shows the amino acid sequence of a murine protein of the present invention;

SEQ ID NO:3 shows the amino acid sequence of a rat protein of the present invention;

SEQ ID NO:4 shows the nucleotide sequence of a DNA coding for the human protein having the amino acid sequence represented by SEQ ID NO:1 of the present invention;

SEQ ID NO:5 shows the nucleotide sequence of a DNA containing the DNA coding for the human protein having the amino acid sequence represented by SEQ ID NO:1 of the present invention as inserted in plasmid pTB1939;

SEQ ID NO:6 shows the nucleotide sequence of a DNA containing the DNA coding for the human protein having the amino acid sequence represented by SEQ ID NO:1 of the present invention as inserted in plasmid pTB1940;

SEQ ID NO:7 shows the nucleotide sequence of a DNA coding for the murine protein having the amino acid sequence represented by SEQ ID NO:2 of the present invention;

SEQ ID NO:8 shows the nucleotide sequence of a DNA containing the DNA coding for the murine protein having the amino acid sequence represented by SEQ ID NO:2 of the present invention as inserted in plasmid pTB1958;

SEQ ID NO:9 shows the nucleotide sequence of a genomic DNA coding for the murine protein having the amino acid sequence represented by SEQ ID NO:2.

SEQ ID NO:10 shows the nucleotide sequence of a DNA coding for the rat protein having the amino acid sequence represented by SEQ ID NO:3 of the present invention.

SEQ ID NO:11 shows the nucleotide sequence of a synthetic oligonucleotide used for cloning of the DNA coding for the human protein of the present invention;

SEQ ID NO:12 shows the nucleotide sequence of a primer used for cloning of the DNA coding for the human protein of the present invention;

SEQ ID NO:13 shows the nucleotide sequence of a primer used for cloning of the DNA coding for the human protein of the present invention;

SEQ ID NO:14 shows the nucleotide sequence of a primer used for cloning of the DNA coding for the murine protein of the present invention;

SEQ ID NO:15 shows the nucleotide sequence of a primer used for cloning of the DNA coding for the murine protein of the present invention;

SEQ ID NO:16 shows the nucleotide sequence of a synthetic oligonucleotide used in the analysis of the nucleotide sequence in the vicinity of the initiation codon of the DNA coding for the murine protein of the present invention;

SEQ ID NO:17 shows the nucleotide sequence of a synthetic oligonucleotide used in the analysis of the nucleotide sequence in the vicinity of the initiation codon of the DNA coding for the murine protein of the present invention;

SEQ ID NO:18 shows the nucleotide sequence of an adaptor ligated to both ends of the mouse genomic DNA fragments used in the analysis of the nucleotide sequence in the vicinity of the initiation codon of the DNA coding for the murine protein of the present invention;

SEQ ID NO:19 shows the nucleotide sequence of a synthetic oligonucleotide used in the analysis of the nucleotide sequence in the vicinity of the initiation codon of the DNA coding for the murine protein of the present invention;

SEQ ID NO:20 shows the nucleotide sequence of a synthetic oligonucleotide used in the analysis of the nucleotide sequence in the vicinity of the initiation codon of the DNA coding for the murine protein of the present invention;

SEQ ID NO:21 shows the nucleotide sequence of a primer used for the construction of a *Pichia pastoris* expression vector of the human protein of the present invention.

SEQ ID NO:22 shows the nucleotide sequence of a primer used for the construction of a *Pichia pastoris* expression vector of the human protein of the present invention.

SEQ ID NO:23 shows the nucleotide sequence of a primer used for cloning of the DNA coding for the rat protein of the present invention;

SEQ ID NO:24 shows the nucleotide sequence of a primer used for cloning of the DNA coding for the rat protein of the present invention;

SEQ ID NO:25 shows the general formula of the amino acid sequence of the protein of the present invention.

The transformant strain of Escherichia coli DH10B/pTB1939 and *Escherichia coli* DH10B/pTB1940, which are obtained in the Example 1 mentioned hereinafter, are on deposit under the terms of the Budapest Treaty form Jul. 17, 1996, with the NIBH under the Accession Number of FERM BP-5595 and FERM BP-5596, respectively. They are also on deposit from Jul. 11, 1996 with the IFO under the Accession Number of IFO 15997 and IFO 15998, respectively.

The transformant strain of *Escherichia coli,* designated DH5α/pTB1958, which is obtained in the Example 2 mentioned hereinafter, is on deposit under the terms of the Budapest Treaty from Jan. 30, 1997, with the NIBH under the Accession Number of FERM BP-5805. It is also on deposit from Jan. 31, 1997 with the IFO under the Accession Number of IFO 16054.

The transformant strain of *Escherichia coli*, designated DH5α/PTB2011, which is obtained in the Example 3 mentioned hereinafter, is on deposit under the terms of the Budapest Treaty from Jul. 8, 1997, with the NIBH under the Accession Number of FERM BP-6012. It is also on deposit from Jul. 7, 1997 with the IFO under the Accession Number of IFO 16109.

The transformant strain of *Escherichia coli*, designated DH5α/PTB2012, which is obtained in the Example 5 mentioned hereinafter, is on deposit under the terms of the Budapest Treaty from Jul. 8, 1997, with the NIBH under the Accession Number of FERM BP 6013. It is also on deposit from Jul. 7, 1997 with the IFO under the Accession Number of IFO 16110.

BRIEF DESCRIPTION OF THE DRAWINGS

FIGS. 1A–1C shows the nucleotide sequence of the DNA coding for the human protein of the present invention as harbored by the plasmid pTB1939 obtained in Example 1 and the amino acid sequence of the human protein of the present invention as deduced from the nucleotide sequence;

FIGS. 2A–2C shows the nucleotide sequence of the DNA coding for the human protein of the present invention as harbored by the plasmid pTB1940 obtained in Example 1 and the amino acid sequence of the human protein of the present invention as deduced from the nucleotide sequence;

FIGS. 3A–3B shows the nucleotide sequence of the DNA coding for the murine protein of the present invention as harbored by the plasmid pTB1958 obtained in Example 2 and the amino acid sequence of the murine protein of the present invention as deduced from the nucleotide sequence.

FIGS. 4A–4J shows the nucleotide sequence of the genomic DNA coding for the murine protein of the present invention as harbored by the plasmid pTB2011 obtained in Example 3 and the amino acid sequence of the murine protein of the present invention as deduced from the nucleotide sequence.

FIGS. 6A–6B shows the nucleotide sequence of the DNA coding for the rat protein of the present invention as harbored by the plasmid PTB2012 obtained in Example 5 and the amino acid sequence of the rat protein of the present invention as deduced from the nucleotide sequence.

BEST MODE FOR CARRYING OUT THE PRESENT INVENTION

EXAMPLES

Figure 5:
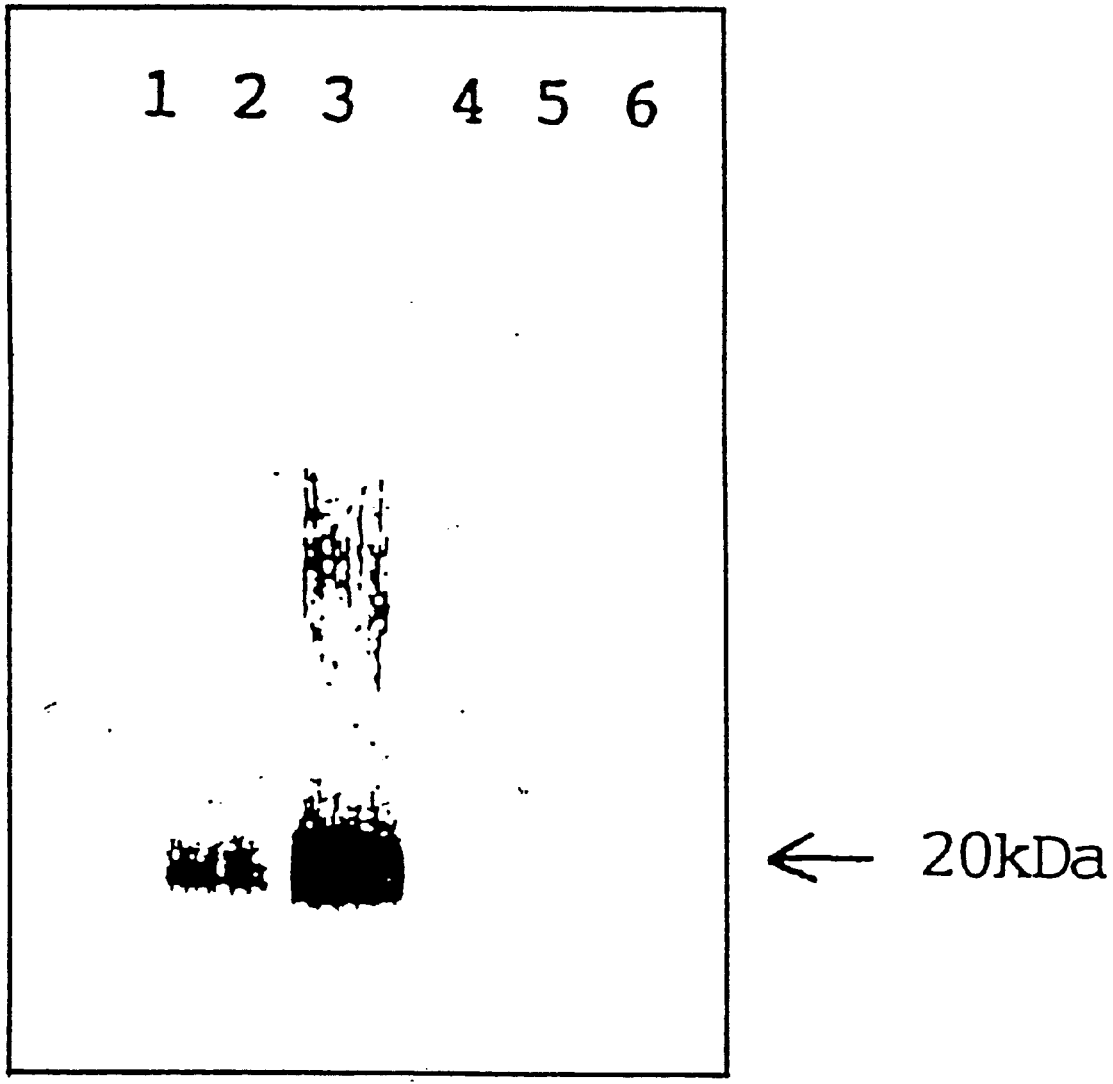
FIG. 5 shows the result of the western blot analysis in Example 4 by using the recombinant protein corresponding to the extracellular domain of the human Fas ligand-like protein of the present invention and the antiserum against the protein. The lanes 1, 2 and 3 show the result of the culture supernatant of the strain transfected with the expression vector, and the lanes 4, 5 and 6 show the result of the control. The lanes 1 and 4, 2 and 5, and 3 and 6 show the result of 0 day-, 1 day- and 2 days-culture, respectively. The band shows the existence of the recombinant protein.

The following examples are intended to describe the present invention in further detail and should by no means be interpreted as defining the scope of the present invention. The gene manipulation using *Escherichia coli* was carried out in accordance with the procedure described in Molecular Cloning.

Example 1

Cloning of the cDNA Coding for a Human Fas Ligand-like Protein

The cloning of cDNA was performed using GENETRAPPER™ cDNA Positive Selection System (Gibco BRL).

*E. coli* DH12S cells of SUPERSCRIPT™ human liver-derived cDNA library (GIBCO BRL) were cultured in Terrific Broth (12 g/l Bacto-tryptone (Difco), 24 g/l Bacto-yeast extract (Difco), 2.3 g/l monopotassium phosphate, 12.5 g/l dipotassium phosphate, 0.4% glycerol) containing 100 μg/ml ampicillin for 16 hours at 30° C. Plasmid DNAs from the amplified cDNA library were prepared by using QIAGEN Plasmid Kit (GIAGEN). The purified plasmid cDNA library was digested with GeneII and ExoIII (both Gibco BRL) to provide a single-stranded cDNA library.

On the other hand, a synthetic oligonucleotide (SEQ ID NO:11) was used as the probe in the screening of the cDNA library. The probe was biotinylated for labeling at the 3'-end using TdT tailed with biotin-14-dCTP (Gibco BRL). After the single-stranded cDNA library was treated at 95° C. for 1 minute, it was quenched on ice and the biotinylated probe was added. Hybridization was performed at 37° C. for 1 hour and, then, at room temperature. GENETRAPPER™ cDNA Positive Selection System streptavidin beads (Gibco BRL) were then added and the mixture was allowed to stand for 30 minutes, with stirring at 2-minute intervals. The beads were placed in GENETRAPPER™ cDNA Positive Selection System magnet rack (Gibco BRL) and allowed to stand for 2 hours. The supernatant was then discarded and the magnet beads were washed with GENETRAPPER™ cDNA Positive Selection System wash buffer. This washing with the wash buffer was carried out 3 times. Then, the beads were put back in the magnetic rack and allowed to stand. After the supernatant was discarded, GENETRAPPER™ cDNA Positive Selection System elution buffer was added and the system was allowed to stand at room temperature for 5 minutes. After 5 minutes in the magnet rack, the supernatant DNA solution was recovered.

To the DNA solution thus recovered was added a synthetic oligonucleotide (SEQ ID NO:11) as a primer and the mixture was treated at 95° C. for 1 minute. GENETRAPPER™ cDNA Positive Selection System repair enzyme was then added and the mixture was allowed to stand at 70° C. for 15 minutes to synthesize a double-stranded DNA. The double-stranded DNA thus synthesized was introduced into *E. coli* DH10B using an electroporation apparatus (Bio-Rad).

Using the transformant thus obtained and two oligonucleotides (SEQ ID NO:12 and NO:13) as primers, a screening by colony PCR technique was carried out and 3 colonies (#9, #33, #81) with which 434bp DNA fragments were PCR-amplified, were selected as positive clones.

Each selected *E. coli* clone was cultured and the DNA was extracted. Sequencing was carried out using Taq dideoxy terminator cycle sequencing kit (Perkin-Elmer) and the nucleotide sequences of the cDNA fragments were determined using ABI PRISM™ 377 DNA sequencer (Perkin-Elmer). Of the 3 clones obtained, Clone #9 and Clone #33 were found to contain the same DNA fragment and had a 1491-base nucleotide sequence containing the poly(A)$^+$ chain as represented by SEQ ID NO:5 (FIG. 1). Clone #81 had a 1353-base nucleotide sequence containing the poly (A)$^+$ chain and poly(A)$^+$ coupling signal (AATAA) as represented by SEQ ID NO:6 (FIG. 2). Those 3 cDNA fragments contained the same gene, with a novel Fas ligand-like protein comprising 240 amino acid residues represented by SEQ ID NO:1 having been encoded. Moreover, Kyte-Doolittle analysis suggested that the putative hydrophobic region from 35Trp to 63Trp corresponds to the transmembrane domain of this protein. This protein showed the highest homology with human lymphotoxin-β, with 33% homology at the amino acid level. The protein was 31% homologous with human Fas ligand at the amino acid level but phylogenetic tree analysis by the method of J. Hein (based on the PAM250 residue weight table) showed higher homology to human Fas ligand than to human lymphotoxin-β.

Among the DNAs coding for the protein of the present invention, plasmid pTB1939 harboring Clone #9, plasmid pTB1940 harboring Clone #81 were respectively introduced into *E. coli* DH10B to provide the transformants *E. coli* DH10B/pTB1939 and *E. coli* DH10B/pTB1940.

Example 2

Cloning of the cDNA Coding for a Murine Fas Ligand-like Protein

The cloning of the cDNA was carried out by PCR technique.

*E. coli* DH12S cells of SUPERSCRIPT™ mouse 8.5 day embryo cDNA library (Gibco BRL) was cultured in Super Broth (32 g/l Bacto-tryptone (Difco), 20 g/l Bacto-yeast extract (Difco), 0.2 g/l NaCl) containing 100 μg/ml ampicillin at 30° C. for 16 hours, and then by using Qiagen Plasmid Kit (Qiagen), plasmid DNAs from the amplified cDNA library were prepared and used as a template.

As the primers, the following two synthetic oligonucleotides were used.

5'-TCTGCTCTGGCATGGAGAGTGTGGT-3' (SEQ ID NO:14)

5'-CTATTGCTGGGTTTGAGGTGAGTC-3' (SEQ ID NO:15)

The PCR was carried out in a system containing TaKaRa Ex Taq (Takara) using a thermal cycler (GeneAmp® PCR System 2400, Perkin-Elmer) with the following program:

1 cycle of: 95° C., 1 min 30 cycles of:
    94° C., 20 s
    55° C., 30 s
    72° C., 2 min 4° C., Soak The amplified fragment thus obtained was inserted in pT7Blue T-Vector (Novagen) using DNA Ligation Kit Version 2 (Takara) and introduced into *E. coli* DH5α.

From a resultant *E. coli* transformant, the plasmid DNA was extracted and allowed for the Cycle sequencing reaction by using Dye Terminator Cycle Sequence FS Ready Reaction Kit (Perkin-Elmer). The nucleotide sequence of the DNA fragment was analysed with the 373A DNA Sequencer (Perkin-Elmer).

The obtained clone contained a 795-base nucleotide sequence of SEQ ID NO:8 containing a 717-base nucleotide sequence of SEQ ID NO:7 which codes for the murine Fas ligand-like protein having the 239-amino acid residues represented by SEQ ID NO:2 (FIG. 3). This murine Fas ligand-like protein 78% homologous to the human Fas ligand-like protein having the amino acid sequence represented by SEQ ID NO:1 as obtained in Example 1. The nucleotide sequence coding for the murine protein was also 77% homologous to that for the human protein.

The resulting plasmid pTB1958 harboring the DNA coding for the murine-derived Fas ligand-like protein was introduced into *E. coli* DH5α to provide the transformant *E. coli* DH5α/pTB1958.

Then, using Promoter Finder DNA Walking Kit (Clontech), the sequence around the initiation codon of the DNA coding for the murine-derived protein of the present invention was analyzed.

The murine genomic DNA used had been pre-digested with a restriction enzyme ScaI and provided with the adaptor sequence at the 5'- and 3'-ends for coupling with primer AP1 (Clontech) and primer AP2 (Clontech).
(1) Primer AP1: (SEQ ID NO:16) 5'-GTAATACGACT CACTATAGGGC-3'
(2) Primer AP2: (SEQ ID NO:17) 5'-ACTATAGGGCA CGCGTGGT-3'
(3) Adaptor sequence: (SEQ ID NO:18) 5'-GTAATA CGACTCACTATAGGGCACGCGTGGTCGACGGCC CGGGCTGGT-3'

The first PCR was carried out by using a solution of said murine genomic DNA digest, TaKaRa LA PCR Kit Version 2 (Takara), AP1, and an under-mentioned synthetic oligonucleotide GSP1 in a thermal cycler (GeneAmp® PCR System 2400, Perkin-Elmer) with the following program:
 7 cycles of:
  94° C., 2 s
  72° C., 3 min
 37 cycles of:
  94° C., 2 s
  68° C., 3 min
 1 cycle of: 68° C., 4 min
 4° C., Soak
(4) Synthetic oligonucleotide GSP1: (SEQ ID NO:19) 5'-CAGCCCAGCACCTAGCAGCAGCACCAG-3'

This reaction mixture was diluted 50-fold with sterilized water and then used for the second PCR with TaKaRa LA PCR Kit Version 2 (Takara), primer AP2, and the under-mentioned synthetic oligonucleotide GSP2 in a thermal cycler (GeneAmp® PCR System 2400, Perkin-Elmer) with the following program:
 5 cycles of:
  94° C., 2 s
  72° C., 3 min
 25 cycles of:
  94° C., 2 s
  68° C., 3 min
 1 cycle of: 68° C., 4 min
 4° C., Soak
(5) Synthetic oligonucleotide GSP2: (SEQ ID NO:20) 5'-GCCGCCTGAATGGGATGTCCGTCTGTC-3'

A single 1.1 kbp of DNA fragment amplified from the ScaI-digested genomic DNA solution was inserted in pT7Blue-T-Vector (Novagen) using DNA Ligation Kit Version 2 (Takara) and introduced into *E. coli* DH5α to provide a transformant.

From this transformant, the plasmid DNA was extracted and the cycle sequencing reaction was carried out by using Dye Terminator Cycle Sequence FS Ready Reaction Kit (Perkin-Elmer). Then, using 373A DNA Sequencer (Perkin-Elmer), a partial nucleotide sequence of the amplified fragment was determined. The obtained clone harbored a sequence in complete agreement with the nucleotide sequence coding for 1Met (initiation codon) through 13Asp of the murine protein having the amino acid sequence of SEQ ID NO:2 (the nucleotide sequence corresponding to the 1st base through the 39th base of the nucleotide sequence of SEQ ID NO:7), indicating that the sequence of the synthetic oligonucleotide (SEQ ID NO:14) used in the above-described cloning of the cDNA coding for the murine protein of the present invention was a part of the sequence of the DNA actually encoding the murine protein of the present invention.

Example 3

Cloning of a Murine Genomic DNA Fragment Coding for the Murine Fas Ligand-like Protein A murine genomic DNA fragment coding for the murine Fas ligand-like protein was isolated. Thus, plaque hybridization was carried out by using the Lamda FIX II library (Stratagene) integrated with the 129SVJ mouse chromosomal DNA partially digested with Sau3AI and the labeled murine cDNA as obtained Example 2 as a template and a probe, respectively. At first, a phage solution of the library diluted to 1–10×10$^4$ pfu (plaque-forming units)/ml was mixed with the same volume of culture broth of *E. coli* XL1-Blue MRA cultured overnight at 30° C. in LB medium supplemented with 0.2% maltose and 10 mM MgSO$_4$ and the mixture was incubated at 37° C. for 10 minutes. To 200 μl aliquots of this mixture were added 5 ml aliquots of top agarose (0.7% agarose-NZY medium (5 g/l NaCl, 2 g/l MgSO$_4$.7H$_2$O, 5 g/l yeast extract, 10 g/l NZ amine (adjusted to pH 7.5)) prewarmed to 50° C., and then uniformly overlaid on NZY plates (1.5% agarose, 9 cm-dish). The plates were incubated at 37° C. for 9 hours. Then nylon transfer membranes Hybond™-N+ (Amersham) marked for identification of the plate position beforehand were intimately put on the the plaque-forming plates and removed after standing for 1 minute for transfer of the emergent phage particles onto the membranes. These membranes were placed on a Whatman 3 MM filter paper (Whatman International) which was saturated with denaturing solution (1.5 M NaCl, 0.5 M NaOH), phage side up, for 7 minutes. Then, on a paper which was saturated with neutralizing solution (1.5 M NaCl, 0.5 M Tris-HCl (pH 7.2), 1 mM EDTA), phage side up, for 3 minutes. This neutralization was carried out again and the filter was washed with 2×SSC solution (0.3 M NaCl, 0.03 M sodium citrate). The membranes were placed, DNA side up to dry and then on a paper which is saturated with 0.4 M NaOH, phage side up, for 20 minutes. They were then washed with 5×SSC solution (0.75 M NaCl, 75 mM sodium citrate) and packed in hybridization bags. To these bags was added 5 ml of ECL Gene Detection System (Amersham) hybridization buffer and prehybridization was carried out at 42° C. for 1 hour. On the other hand, a PCR-amplified DNA fragment corresponding to the open reading frame (ca 0.72 kb) of the murine cDNA was labeled by ECL direct nucleic acid labelling systems (Amersham) as below.

The DNA fragment was denatured by heating for 5 minutes in a boiling water bath, and immediately cooled on ice for 5 minutes. An equivalent volume of DNA labelling reagent was added to the denatured DNA followed by adding the same volume of glutaraldehyde solution. The reagent mixture was mixed and incubated for 10 min at 37° C. Ten microliter of the mixture was added to the hybridization bag, followed by 1-hour incubation at 42° C. The filter was then taken from the bag and washed with a primary wash buffer (6 M urea, 4 g/l SDS, 25 ml/l 20×SSC) pre-warmed at 42° C. for 20 minutes. This washing procedure was carried out again and the filter was then washed twice with a second wash buffer (2×SSC) for 5 minutes. Then the membranes were immersed in ECL Gene Detection System detection reagent for 1 minute and each filter was in contact with a sheet of X-ray film. The films were removed after 1 hour exposure and developed, and positive clones were selected. Each selected clone was subjected to a secondary screening by the same procedure as above and ultimately 5 candidate clones (#2, 3, 4, 5, and 6) were acquired. The results of PCR experiments using these clones showed that #1 and #6 clones had the entire region corresponding to the coding sequence of the the murine Fas ligand-like protein.

Then, subcloning was carried out to identify the nucleotide sequence of the genomic DNA including the coding sequence of the murine Fas ligand-like protein. First, Clone #6 obtained above was digested with the restriction enzyme XbaI and subjected to 0.7% agarose gel electrophoresis. A 9 kb DNA fragment which was considered to contain the coding sequence of the murine Fas ligand-like protein, was excised and was purified using QIAquick Gel Extraction Kit (Qiagen). On the other hand, a cloning vector pUC19 was digested with the restriction enzyme XbaI and electrophoresed on 1.0% agarose gel. A DNA fragment corresponding to 2.7 kb was excised and was purified by using QIAquick Gel Extraction Kit (Qiagen). To prevent the self-ligation of the vector itself, it was dephosphorylated with a bovine small intestine-derived alkaline phosphatase CIAP (Takara). The DNA fragment derived from Clone #6 was inserted to the CIAP-treated pUC19 by using DNA Ligation Kit Version 2 (Takara) and was introduced into *E. coli* DH5α. The plasmid DNA containing the objective fragment was prepared from the resulting transformant cells. The nucleotide sequence of the cloned XbaI DNA fragment derived from Clone #6 was determined by carrying out a cycle sequencing using various synthetic oligonucleotides as primers and ABI PRISM™ Dye Terminator Cycle Sequencing FS Ready Reaction Kit (Perkin-Elmer) in GeneAmp PCR System 2400 in accordance with the attached instruction manual, following with sequencing of the samples with DNA Sequencer 373A (Perkin-Elmer). The nucleotide sequence thus determined was verified by using a gene analysis software Lasergene (DNASTAR). The result indicated that the genomic gene encoding the murine Fas ligand-like protein consisted of four exons (FIG. 4). The plasmid harboring the Clone #6-derived XbaI DNA fragment including the entire region of the coding sequence of the murine Fas ligand-like protein was named pTB2011 and the transformant acquired by introduction of the plasmid into *Escherichia coli* DH5α was named *E. coli* DH5α/pTB2011.

Example 4

Expression of the Extracellular Domain of the Human Fas Ligand-like Protein Using an Yeast (Pichia) Expression System and the Western Blot Analysis pPICZαA (Invitrogen) was used as an expression vector for the extracellular domain of the human Fas ligand-like protein of the present invention in *Pichia pastoris*. Since this vector contains, downstream of the promoter for the alcohol oxidase gene (AOX1) of said yeast, the α-factor signal sequence of the budding yeast, *Saccharomyces cerevisiae* which is functional even in said yeast as well and a multi-cloning site in that order, it can be used to express and secrete recombinant proteins in *Pichia pastoris*.

The DNA fragment coding for the extracellular domain of the human Fas ligand-like protein of the present invention was prepared by PCR technique as follows. The following two primers were synthesized by a DNA synthesizer (Oligo1000 M, BACKMAN).

(1) 5'-Primer (SEQ ID NO:21) ACGAATTCCAAGAGC-GAAGGTCTCACGAGGTC (This primer has an EcoRI recognition sequence and, at the 3'-end thereof, 24 bases coding for a sequence of 8 amino acid residues beginning with the N-terminal 85th Gln of the extracellular domain of the human Fas ligand-like protein of the present invention.)

(2) 3'-Primer (SEQ ID NO:22) AGTCTAGACTCCTTCCT-TCACACCATGAAAGCCCC (This primer comprises an XbaI recognition sequence and, at the 3'-end thereof, a sequence complementary to a termination codon (TGA) and 15 bases coding for the C-terminal 5 amino acid residues of the extracellular domain of the human Fas ligand-like protein of the present invention.)

A solution (final 50 μl) containing 50 pmol each of the above primers, 100 ng of the plasmid pTB1939 obtained in Example 1, 10 nmol each of dATP, dCTP, dGTP, and dTTP, 2.5 units of native Pfu DNA polymerase (Stratagene), and 5 μl of native Pfu buffer (Stratagene) was subjected to PCR on a thermal cycler (GeneAmp® PCR System 2400, Perkin-Elmer) with the following program:

1 cycle of: 94° C., 1 min
30 cycles of:
  98° C., 20 s
  55° C., 30 s
  68° C., 2 min
1 cycle of: 72° C., 5 min At completion of the reaction, the PCR product was recovered, digested with EcoRI and XbaI, and ligated to the EcoRI/XbaI-predigested, linearized pPICZαA to give the circulated plasmid. This plasmid DNA was relinearized by cutting at the unique SacI restriction site at AOX1 locus and introduced into *Pichia pastoris* KMX71 by the electroporation method. Among the Zeocin™-resistant transformants capable of growing on 100 μg/ml Zeocin™ (Invitrogen)-YPD agar medium (1% yeast extract (Difco), 2% Bactopeptone (Difco), 2% glucose (Wako Pure Chemical), 2% agar (Wako Pure Chemical)) thus obtained, several clones were selected and the respective chromosomal DNAs were prepared for use as templates. PCR was carried out to confirm integration of the introduced plasmid DNA with the yeast chromosome and clones for which integration was verified as expected were selected as the transformants for expression of the objective recombinant protein.

Expression of the recombinant protein was carried out by the following procedure. First, a single transformant colony was taken to inoculate 25 ml of BMGY medium (1% yeast extract, 2% peptone, 100 mM potassium phosphate (pH 6.0), 1.34% yeast nitrogen base with ammonium sulfate without amino acids (Difco), $4 \times 10^{-5}$% biotin, 1% glycerol) and cultured at 30° C. for 20 hours. Cells were then harvested by centrifugation, resuspended in BMMY medium (1% yeast extract, 2% peptone, 100 mM potassium phosphate (pH 6.0), 1.34% yeast nitrogen base with ammonium sulfate without amino acids (Difco), $4 \times 10^{-5}$% biotin, 0.5% methanol) at an $OD_{600}=1.0$ and grown at 30° C. Sampling of cultures was carried out after 1 and 2 days and each sample was centrifuged to provide a supernatant.

Western blot analysis with the culture supernatants was carried out as follows. First, a peptide comprising a part (166 to 180 amino acid residues of the amino acid sequence represented by SEQ ID NO:1 ) of the amino acid sequence of the extracellular domain of the human Fas ligand-like protein of the present invention was synthesized and a rabbit antiserum recognizing this synthetic peptide was prepared by the known method. Then, each 5 μl of the above culture supernatants was mixed with 5 μl of a sample buffer (0.25 M Tris-HCl, 2% SDS, 30% glycerol, 10% β-mercaptoethanol, 0.01% bromophenol blue, pH 6.8) and the mixture was treated at 95° C. for 5 minutes and electrophoresed on SDS-polyacrylamide gel (10–20% gradient gels). After completion of electrophoresis, proteins were transferred onto a nitrocellulose membrane (Pharmacia) using a protein blotting apparatus (SemiPhor™, Hoefer Pharmacia BioTech). The membrane was blocked with 3% gelatin-TBS (20 mM Tris, 500 mM NaCl, pH 7.5), washed with TTBS (0.05% Tween 20-TBS), and reacted with the above rabbit antiserum diluted 2000-fold with 1.0% gelatin-TTBS at room temperature for 2 hours. After completion of the reaction, the membrane was washed with TTBS twice and then reacted with the alkaline phosphatase (AP)-conjugated goat anti-rabbit IgG antibody diluted 3000-fold with 1.0% gelatin-TTBS at room temperature for 1 hour. The membrane was washed with TTBS twice and then with TBS once and detection was carried out by using an AP color development kit (BIORAD).

The Western blot analysis obtained are shown in FIG. 5. As for the culture supernatant of the strain transformed with the expression vector, a major band was detected in the vicinity of about 20 KDa and the intensity of the signal was increased in accordance with time. In contrast, the culture supernatant of the control strain transformed with intact pPICZαA yielded no band at all.

Example 5

Cloning of the cDNA Coding for a Rat Fas Ligand-like Protein

The cDNA coding for a rat Fas ligand-like protein was cloned by PCR method as follows.

*E coli* DH12S cells of SUPERSCRIPT™ rat liver cDNA library (GIBCO BRL) were cultured in Terrific Broth (12 g/l Bacto-tryptone (Difco), 24 g/l Bacto-yeast extract (Difco), 2.3 g/l monopotassium phosphate, 12.5 g/l dipotassium phosphate, 0.4% glycerol) containing 100 μg/ml ampicillin for 16 hours at 30° C. Plasmid DNAs from the amplified cDNA library were prepared by using GIAGEN Plasmid Kit (QIAGEN). The plasmid DNAS, two synthetic oligonucleotides (SEQ ID NO:23 and 24), and TaKaRa LA Taq (Takara) were used for PCR as template, primers, and DNA polymerase, respectively.

5'-CCTGACCCTGGGCTTCTGAGCCTC-3' (SEQ ID NO:23)

5'-TCCACAAAATCCATTGTCGTCATAGCC-3' (SEQ ID NO:24)

The PCR was carried out with the following program designed for a thermal cycler (GeneAmp® PCR system 2400, Perkin-Elmer):

1 cycle of: 94° C., 1 min
35 cycles of:
  98° C., 20 s
  55° C., 30 s
  72° C., 3 min
1 cycle of: 72° C., 2 min
4° C., Soak Following the amplification of the only PCR product checked by 1.0% agarose gel electrophresis, the amplified DNA fragment was recovered by GIAquick Gel Extraction Kit (QIAGEN) and was subcloned into the T-cloning site of pT7Blue T-vector (Novagen) by using DNA Ligation Kit Ver.2 (Takara). After transformation of *E. coli* DH5α using the ligation mixture, two clones were selected among ampicillin-resistant colonies viable on a LB plate containing 100 μg/ml ampicillin, followed by preparation of each plasmid DNA. To determine each nucleotide sequence of the insert DNAs, Thermo Sequenase™ dye terminator cycle sequencing pre-mix kit (Amersham) was used for cycle sequencing with two commercially available primer DNAs, (PRM-007 and PRM-008, TOYOBO) and primer DNAs synthesized by a DNA synthesizer (Oligo1000 M, BECKMAN). The reaction was performed according to the protocol designed for the kit by GeneAmp® PCR System 2400 and the obtained samples were loaded onto the sequencing gel for a DNA sequencer (373A, Perkin-Elmer). Nucleotide sequence data thus obtained were further analysed by using an analysis software (Lasergene, DNASTAR). The results showed that the identical DNA fragment was inserted in both clones and that the insert DNA consisted of 784 base pairs which contained an open reading frame comprising 717-base nucleotide sequence represented by SEQ ID NO:10, which encoded a rat Fas ligand-like protein comprising 239 amino acid residues represented by SEQ ID NO:3 (FIG. 6). This rat-derived protein was 75% and 96% homologous to the human Fas ligand-like protein and the murine Fas ligand-like protein, having the amino acid sequences represented by SEQ ID NO:1 and NO:2 as obtained in Example 1 and Example 2, respectively. The nucleotide sequence coding for the rat-derived protein was also 74% and 94% homologous to those for the human Fas ligand-like protein and the murine Fas ligand-like protein described in Example 1 and Example 2, respectively.

The resultant plasmid pTB2012 harboring the DNA coding for the rat Fas ligand-like protein was introduced into *E. coli* DH5α to provide the transformant *E. coli* DH5α/pTB2012.

INDUSTRIAL APPLICABILITY

The protein of the present invention, its partial peptide or a salt thereof has an apoptosis-inducing, cytotoxic activity, and so on. Therefore, the protein, its partial peptide or a salt thereof, as well as the DNA of the present invention, is useful for a therapeutic or prophylactic agent for various deseases such as cancer (e.g. breast cancer, prostate cancer, ovary cancer, follicular lymphoma, cancer associated with p53 mutation, brain tumor, urinary bladder cancer, uterocervical cancer, colon cancer (colorectal cancer), non-small cell carcinoma of lung, small cell carcinoma of lung, stomach cancer, etc.), viral or bacterial infection (e.g. incipient stage of AIDS virus infection, herpes virus infection, adenovirus infection, poxvirus infection, *Helicobacter pylori* infection, varicella-zoster virus infection, human papillomavirus infection, invasive staphylococcia, etc.), hepatitis (e.g. hepatitis A, hepatitis C, etc.), nephritis, autoimmune disease (e.g. systemic lupus erythematosus, immune complex glomerulonephritis, etc.), bone disease (e.g. rheumatoid arthritis (e.g. abnormal proliferation of synuvial cells in rheumatism)), atherosclerosis and pain.

The DNA of the present invention is also useful as a gene diagnostic agent for various diseases such as cancer, viral infections, hepatitis, nephritis, rheumatoid arthritis, and autoimmune diseases.

The antibody against the protein, its partial peptide or a salt thereof of the present invention specifically recognizes the protein, its partial peptide or a salt thereof and can, therefore, be used for the quantitative determination of the protein, etc. of the present invention. Moreover, the antibody of the present invention, which neutralizes the protein, etc. of the present invention is useful for, for example, a therapeutic or prophylactic agent for AIDS, joint tissue destruction in rheumatism, hepatitis, autoimmune disease, and so on.

The protein, its partial peptide or a salt thereof of the present invention is also useful as a reagent for the screening for compounds capable of changing the binding activity of the protein, etc. of the present invention to a receptor, compounds capable of promoting or inhibiting an activity of a proteinase, or compounds capable of promoting or suppressing an intracellular signal transduction following the binding of the protein, etc. of the invention to a receptor.

What is claimed is:

1. An isolated DNA comprising a DNA having a nucleotide sequence coding for a protein comprising amino acid sequence represented by SEQ ID NO: 1, SEQ ID NO: 2 or SEQ ID NO: 3.

2. The isolated DNA of claim 1 has not less than about 80% identity to the nucleotide sequence of SEQ ID NO: 4, 7, or 10.

3. The isolated DNA according to claim 1, which has a nucleotide sequence represented by any one of SEQ ID NO:4 to SEQ ID NO:10.

4. A recombinant vector comprising the isolated DNA according to claim 1.

5. A transformant which is transformed with the recombinant vector according to claim 4.

6. A method for producing a protein or salt thereof which protein comprises amino acid sequence represented by SEQ ID NO: 1, SEQ ID NO: 2 or SEQ ID NO: 3, the method comprising culturing the transformant according to claim 5 under conditions suitable to express and accumulate the protein and collecting the same.

7. A composition comprising the isolated DNA according to claim 1 with a physiologically acceptable carrier.

8. A recombinant vector containing the isolated DNA according to claim 1, wherein the vector is capable of being expressed in a mammal.

* * * * *